United States Patent
Jensen et al.

(10) Patent No.: US 10,919,950 B2
(45) Date of Patent: Feb. 16, 2021

(54) TUMOR-SPECIFIC IFNA SECRETION BY CAR T-CELLS TO REPROGRAM THE SOLID TUMOR MICROENVIRONMENT

(71) Applicant: Seattle Children's Hospital, Seattle, WA (US)

(72) Inventors: Michael C. Jensen, Bainbridge Island, WA (US); Adam Johnson, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 71 days.

(21) Appl. No.: 16/069,485

(22) PCT Filed: Jan. 10, 2017

(86) PCT No.: PCT/US2017/012858
§ 371 (c)(1),
(2) Date: Jul. 11, 2018

(87) PCT Pub. No.: WO2017/123548
PCT Pub. Date: Jul. 20, 2017

(65) Prior Publication Data
US 2019/0016776 A1 Jan. 17, 2019

Related U.S. Application Data

(60) Provisional application No. 62/278,648, filed on Jan. 14, 2016.

(51) Int. Cl.
*C07K 14/705* (2006.01)
*C07K 14/56* (2006.01)
*C07K 14/725* (2006.01)
*C07K 14/555* (2006.01)

(52) U.S. Cl.
CPC ...... *C07K 14/70503* (2013.01); *C07K 14/555* (2013.01); *C07K 14/56* (2013.01); *C07K 14/7051* (2013.01); *C07K 2319/00* (2013.01); *C07K 2319/03* (2013.01); *C12N 2740/16043* (2013.01)

(58) Field of Classification Search
None
See application file for complete search history.

(56) References Cited

U.S. PATENT DOCUMENTS

| 7,888,475 B2 | 2/2011 | Padgett et al. |
| 2003/0017550 A1 | 1/2003 | Pang |
| 2010/0172868 A1 | 7/2010 | Morrison et al. |
| 2011/0008283 A1 | 1/2011 | Artymiuk et al. |
| 2012/0301447 A1* | 11/2012 | Jensen ............... C07K 14/71 424/93.21 |
| 2014/0079668 A1* | 3/2014 | Morrison ............ A61K 38/212 424/85.7 |

FOREIGN PATENT DOCUMENTS

WO  WO 2004/074486 A2  9/2004

OTHER PUBLICATIONS

Xiao et al. 2007, Clin.Canc.Res., vol. 13, pp. 1823-1830 (Year: 2007).*
Kolchanov et al., J. Mol. Evol. (27)p. 154-162 (Year: 1988).*
Xuan et a l. "Targeted delivery of interfe ron-alpha via fusion to anti-C020 results in potent antitumor activity against B-cell lymphoma," Blood, Feb. 4, 201 O (Feb. 4, 2010), vol. 115, No. 14, pp. 2864-2871.
Search Report and Written Opinion in International application No. PC/US2017/012858, dated Apr. 7, 2017.
Crewe et al., "Metabolism of Tamoxifen by Recombinant Human Cytochrome P450 Enzymes: Formation of the 4-Hydroxy, 4'-Hydroxy and N-Desmethyl Metabolites and Isomerization of trans-4-Hydroxytamoxifen," Drug Metabolism and Disposition (Aug. 2002) 30(8):869-874.
Kreutzer et al., "Photodynamic therapy with methylaminooxopentanoate (Metvix) and a broad band light source (PhotoDyn 501): practical experiences in problem-patients with actinic keratosis and basal cell carcinomas," Journal der Deutschen Dermatologischen Gesellschaft = Journal of the German Society of Dermatology, (Jddg) (Nov. 30, 2004) 2(12):992-999—Language:ger.
Osborn et al., "Pharmacokinetic and Pharmacodynamic Studies of a Human Serum Albumin-Interferon-αα Fusion Protein in Cynomolgus Monkeys," J Pharmacol and Experimental Therapeutics (2002) 303(2):540-548.
Pan et al., "Synergistic effects of soluble PD-1 and IL-21 on antitumor immunity against H22 murine hepatocellular carcinoma," Oncology Letters (2013) 5:90-96.
Trinh et al., "Anti-CD20-interferon-β fusion protein therapy of murine B cell lymphomas," J Immunother (Jun. 2013) 36(5):305-318.

* cited by examiner

*Primary Examiner* — Gary B Nickol
*Assistant Examiner* — Jegatheesan Seharaseyon
(74) *Attorney, Agent, or Firm* — Knobbe, Martens, Olson & Bear LLP

(57) ABSTRACT

The present application relates to fusion proteins, chimeric antigen bearing cells expressing fusion proteins and compositions comprising chimeric antigen bearing cells expressing fusion proteins. The application further relates to methods of using the fusion proteins, cells and compositions for modulating an immune response.

19 Claims, 20 Drawing Sheets
Specification includes a Sequence Listing.

Result: PD1-IFNα is about 50% as potent as native IFNα

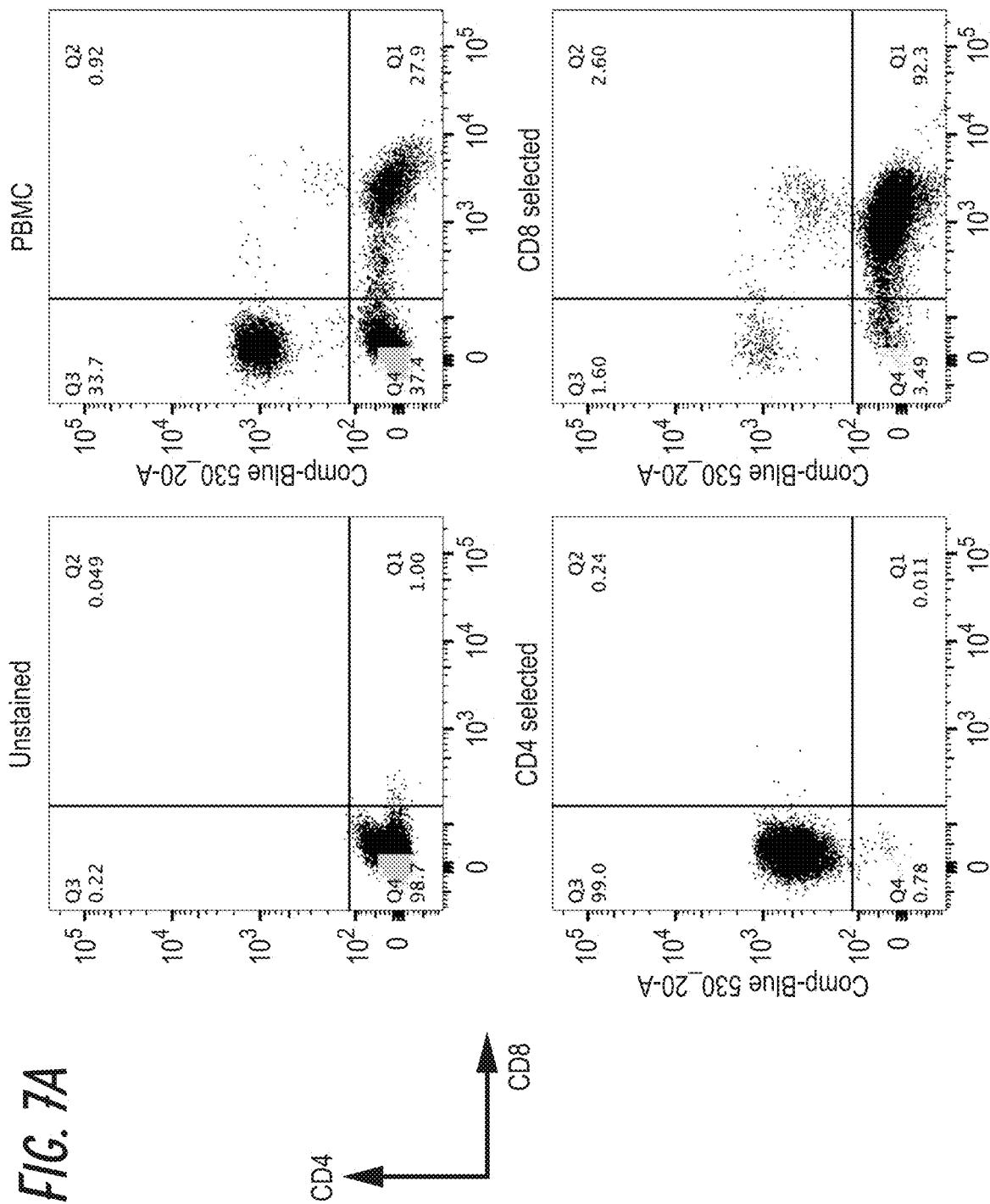

TUMOR-SPECIFIC IFNA SECRETION BY CAR T-CELLS TO REPROGRAM THE SOLID TUMOR MICROENVIRONMENT

RELATED APPLICATIONS

This application is a U.S. National Phase Application of PCT International Application PCT/US2017/012858, filed Jan. 10, 2017, designating the United States of America and published in the English language, which is an International Application of and claims the benefit of priority to U.S. Provisional Patent Application No. 62/278,648, filed on Jan. 14, 2016. The disclosures of the above-referenced applications are hereby expressly incorporated by reference in their entireties.

REFERENCE TO SEQUENCE LISTING, TABLE, OR COMPUTER PROGRAM LISTING

This incorporates by reference the Sequence Listing provided as an ASCII text file entitled SCRI-109NP.TXT, created Jul. 10, 2018, which is 25kb in size. The information is the electronic format of the Sequence Listing is incorporated herein by reference in its entirety.

FIELD OF THE INVENTION

Disclosed herein are compositions and methods relating to a dual-active, secretable fusion protein that can be used in chimeric antigen receptor (CAR) therapy for a subject. Additionally, methods for intrinsic production and secretion of a PD-1:IFNα2a fusion protein in CAR T-cells to support T-cell activity, promote inflammatory cytokine production and decrease immunosuppression within the solid tumor microenvironment, are also provided. These methods and compositions can improve the therapeutic efficacy of CAR T-cell therapy targeted against solid tumors by providing regulatory inputs for multiple immune cell subsets found in the tumor microenvironment.

BACKGROUND OF THE INVENTION

The tumor microenvironment (TME) is the cellular environment in which the tumor exists, and can include surrounding blood vessels, immune cells, fibroblasts, bone marrow-derived inflammatory cells, lymphocytes, signaling molecules and the extracellular matrix (ECM). The tumor and the surrounding microenvironment are closely related and interact constantly. Tumors influence the microenvironment by releasing extracellular signals, promoting tumor angiogenesis and inducing peripheral immune tolerance, while the immune cells in the microenvironment can affect the growth and evolution of cancerous cells.

Due to the TME, the solid tumors and the microenvironment created by the tumors impact infiltrating immune cells that are responsible for the elimination of the tumor and other cancerous type cells. Furthermore, the TME has been known to create a barrier that can also preclude CAR T-cell immunotherapies and other types of therapy for the treatment of cancerous tumors. As such, developments to decrease the effects of the TME and to improve the efficacy of immunotherapies are much needed.

The use of proteins, which illicit an immune response have been investigated for immunotherapy. Type I interferons (IFN) are a large subgroup of interferon proteins that have been known to regulate the activity of the immune system. The type I interferon IFNα2a, can confer dynamic roles against multiple immune cell subsets. More specifically, IFNα2a confers enhanced cytotoxicity in T and NK cells, promotes T-cell stimulatory cytokine production in macrophages and inhibits regulatory T cell function.

The protein, programmed cell death 1 protein (PD-1) and cluster of differentiation protein 279 (CD279) is encoded by the PDCD1 gene, and has been studied for its role in the immune system. PD-1 is a cell surface receptor belonging to the immunoglobulin superfamily and is expressed on T-cells and pro-B cells. PD-1 binds two ligands, PD-L1 and PD-L2.

PD-1 can function as an immune checkpoint, playing an important role in down regulating the immune system by preventing the activation of T-cells, which in turn reduces autoimmunity and promotes self-tolerance. The inhibitory effect of PD-1 is accomplished through a dual mechanism of promoting apoptosis (programmed cell death) in antigen specific T-cells in lymph nodes while simultaneously reducing apoptosis in regulatory T-cells (suppressor T-cells).

Studies that incorporated the soluble, extracellular domain of PD-1 during therapy demonstrate that soluble PD-1 blocks the PD-1 pathway and modulates the antitumor immune response (Pan et al., Oneal Lett (2013); hereby expressly incorporated by reference in its entirety). Alternatively, IFNα treatment has been used for clinical application (Kreutzer et al., Dtsch Dermatol Ges (2004); hereby expressly incorporated by reference in its entirety).

Fusion proteins, which incorporate separate moieties of different proteins, have also been previously described for therapy. For example, Trinh et al developed and described an anti-CD20-IFNα fusion protein used in a mouse model for treatment of lymphomas expressing CD20 (Trinh et al J Immunother (2013); incorporated by referenced in its entirety herein). Osborn et al describes pharmacokinetic studies, which were performed using a human serum albumin-IFNα fusion protein that was developed so as to improve the half-life of IFNα and decrease its dosing frequency (Osborn et al J Pharmacol Exp Ther (2002); incorporated by referenced in its entirety herein). Lee et al describes a cytoplasmic transduction peptide-IFNα fusion used to enhance conjugation capacity of cell membranes and antiviral activity (US20120134961 A1); hereby expressly incorporated by referenced in its entirety). Furthermore Morrison et al. describes the attachment of novel chimeric moieties to IFNα or IFNβ (U.S. Pat. No. 8,563,692 B2; hereby expressly incorporated by reference in its entirety).

As the tumor environment is known to preclude known treatments, such as immunotherapy, approaches are needed to overcome the influence of the TME and methods for modulating the immune response during immunotherapies, such as CAR T-therapy, are also manifest.

SUMMARY OF THE INVENTION

In a first aspect, a nucleic acid encoding a fusion protein is provided. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA- GATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11

(atgcttctcctggtgacaagccttctgctctgtgagttaccacacccagcat-tcctcctgatccca; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGC-TGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13).

In a second aspect, an expression vector comprising the nucleic acid of anyone of the alternatives described herein is provided. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO:1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACAG-CTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCA-GATCCCTCAGGCCCCTTGGCCTGTCGTGTGGGCT-GTGCTGCAGCTGG GATGGCGGCCTGGCTGGTTTCTGGACAGCCCCG-ACAGACCCTGGAACCCCCT ACAT-TTTCCCCTGCCCTGCTGGTCGTGACCGAGGGCG-ACAATGCCACCTTCAC CTGTAGCTTCAGCAACACCAGCGAGAGCTTCGT-GCTGAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACCC-AGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector is RNA or DNA.

In a third aspect, a cell for fusion protein secretion is provided, wherein the cell can comprise the nucleic acid of anyone of the alternatives described herein or the expression vector of anyone of the alternatives described herein. The expression vector can comprise the nucleic acid of anyone of the alternatives described herein. In some alternatives, the vector is RNA or DNA. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G WFLDSPDRPWNPPTFSPALLVVTEGD NATFTCSFSNTSESFVLNWYRMSPSN QTDKLAAFPEDRSQPGQDCRFRVTQ LPNGRDFHMSVVRARRNDSGTYLCG AISLAPKAQIKESLRAELRVTERRAEV PTAHPSPSPRPAGQFQTLV; SEQ ID NO: 4). In some alternatives, the PD-1 is a mutated form of PD-1 and comprises an amino acid sequence set forth in SEQ ID NO: 5 (MQIPQAPWPVVWAVLQLGWRPGW FLDSPDRPWNPPTFSPALLVVTEGDN ATFTCSFSNTSESFVLNWYRMSPSNQ TDKLAAFPEDRSQPGQDCRFRVTQL PNGRDFHMSVVRARRNDSGTYLCGA ISLAPKLQIKESLRAELRVTERRAEVP TAHPSPSPRPAGQFQTLV; SEQ ID NO: 5). In some alternatives, the PD-1 is a mutated form of PD-1 and comprises an amino acid sequence set forth in SEQ ID NO: 6 (MQIPQAPWPVVWAVLQLGWRPGW FLDSPDRPWNPPTFSPALLVVTEGDN ATFTCSFSNTSESFHVVWHRESPSGQ TDTLAAFPEDRSQPGQDCRFRVTQLP NGRDFHMSVVRARRNDSGTYVCGVI SLAPKIQIKESLRAELRVTERRAEVPT AHPSPSPRPAGQFQTLV; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector comprises the nucleic acid of any one of the alternatives herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a nucleic acid encoding a chimeric antigen receptor r. In some alternatives, the chimeric antigen receptor is specific for CD19.

In a fourth aspect, a method of making a chimeric antigen receptor bearing cell, wherein the chimeric antigen receptor bearing cell expresses a fusion protein. The method can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGAAGGTGGCGCGGGGTAAACTGGGAAAGTGATGTCGTGTACTGGCTCCGCCTTTTTCCCGAGGGTGGGGGAGAACCGTATATAAGTGCAGTAGTCGCCGTGAACGTT CTTTTTCGAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector comprises the nucleic acid of any one of the alternatives herein. In some alternatives, the vector is DNA or RNA. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all or a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. In some alternatives, the chimeric antigen receptor is specific for CD19.

In a fifth aspect, a composition comprising the cells of anyone of the alternatives described herein, or the cells manufactured by the methods of anyone of the alternatives described herein, is provided. The cell can comprise the nucleic acid of anyone of the alternatives described herein or the expression vector of anyone of the alternatives described herein. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector comprises the nucleic acid of any one of the alternatives herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the method of making the cell can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The expression vector can comprise the nucleic acid of anyone of the alternatives described herein. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. In some alternatives, the cell further comprises a nucleic acid encoding a chimeric antigen receptor. In some alternatives, the chimeric antigen receptor is specific for CD19.

In a sixth aspect, a fusion protein encoded by the nucleic acid of anyone of the alternatives provided herein, or the vector of anyone of the alternatives provided herein, is provided. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGA-
GACACTGCTGGACAAGTTCTACACCGAG
CTGTACCAGCAGCTGAATGACCTGGAAGCCTGCGT-
GATCCAGGGCGTGGGCG TGACAGAGACACCCCT-
GATGAAGGAAGATAG-
CATCCTGGCCGTGCGCAAGTA
CTTCCAGCGGATCACCCTGTACCT-
GAAAGAGAAGAAGTACAGCCCCTGCGCC TGG-
GAGGTCGTGCGCGCCGAGATCAT-
GAGAAGCTTCAGCCTGAGCACCAACC
TGCAGGAAAGCCTGCGGAGCAAAGAA; SEQ ID NO:
1). In some alternatives, the nucleic acid further comprises
a fourth sequence, wherein the fourth sequence encodes a
promoter. In some alternatives, the promoter is a mammalian
promoter for mammalian cell protein expression or a bacterial promoter for bacterial cell protein expression. In some
alternatives, the promoter is an inducible promoter or a
constitutive promoter. In some alternatives, the promoter is
EF1P. In some alternatives, the fourth sequence comprises a
nucleic acid sequence set forth in SEQ ID NO: 2
(GGATCTGC-
GATCGCTCCGGTGCCCGTCAGTGGGCAGAGCGCA-
CATCGCCCAC AGTCCCCGAGAAGTTGGGGG-
GAGGGGTCGGCAATTGAACCGGTGCCTAGAGA
AGGTGGCGCGGGGTAAACTGGGAAAGT-
GATGTCGTGTACTGGCTCCGCCTTTT
TCCCGAGGGTGGGG-
GAGAACCGTATATAAGTGCAGTAGTCGCCGT-
GAACGTT
CTTTTTCGCAACGGGTTTGCCGCCAGAACACA-
GCTG; SEQ ID NO: 2). In some alternatives, the promoter
is a T7 promoter, lac promoter, trc promoter, tac promoter,
tetA promoter, araBAD promoter or a rhaPBAD promoter.
In some alternatives, the promoter is inducible by IPTG,
anhydrotetracycline, L-arabinose or rhamnose. In some
alternatives, the promoter is regulated by a drug. In some
alternatives, the drug is tamoxifen. In some alternatives, the
promoter is a regulatable promoter, regulated by a CAR-
dependent signal. In some alternatives, the promoter is an
NFAT regulated promoter system. In some alternatives, the
first sequence encodes PD-1, antigen specific binding
domains, antigen specific scFvs, an extracellular domain,
DARPins, affinity peptides, extracellular proteins expressed
by tumor cells, peptides, tumor specific extracellular proteins, Her2, ROR1, embryonal fibronectin or an extracellular
matrix protein. In some alternatives, the extracellular protein
is fibronectin, laminin or collagen. In some alternatives,
PD-1 is a wild type PD-1 or a mutated form of PD-1. In
some alternatives, the first sequence comprises a nucleic
acid sequence set forth in SEQ ID NO: 3 (ATGCA-
GATCCCTCAGGCCCCTTGGCCTGTCGTGTGGGC-
TGTGCTGCAGCTGG
GATGGCGGCCTGGCTGGTTTCTGGACAGCCCCG-
ACAGACCCTGGAACCCCCT ACAT-
TTTCCCCTGCCCTGCTGGTCGTGACCGAGGGCG-
ACAATGCCACCTTCAC
CTGTAGCTTCAGCAACACCAGCGAGAGCTTCGT-
GCTGAACTGGTACAGAATG AGCCCCAGCAACCA-
GACCGACAAGCTGGCCGCCTTCCCCGAGGATA-
GATCTC
AGCCCGGCCAGGACTGCCGGTTCAGAGTGACCC-
AGCTGCCCAACGGCCGGGA CTTCCA-
CATGTCTGTCGTGCGGCCAGACG-
GAACGACAGCGGCACATATCTGT
GCGGCGCCATCAGCCTGGCCCCCAAGGCCCAGAT-
CAAAGAGAGCCTGAGAGC CGAGCT-
GAGAGTGACCGAGAGAAGGGCCGAAGTGCC-
TACCGCCCACCCTAGC
CCATCTCCAAGACCTGCCGGCCAGTTCCA-
GACACTCGTG; SEQ ID NO: 3). In some alternatives,
PD-1 comprises an amino acid sequence set forth in SEQ ID
NO: 4 (M Q I P Q A P W P V V W A V L Q L G W R P G
W F L D S P D R P W N P P T F S P A L L V V T E G D
N A T F T C S F S N T S E S F V L N W Y R M S P S N
Q T D K L A A F P E D R S Q P G Q D C R F R V T Q
L P N G R D F H M S V V R A R R N D S G T Y L C G
A I S L A P K A Q I K E S L R A E L R V T E R R A E V
P T A H P S P S P R P A G Q F Q T L V; SEQ ID NO: 4).
In some alternatives, the PD-1 is a mutated form of PD-1 and
comprises an amino acid sequence set forth in SEQ ID NO:
5 (M Q I P Q A P W P V V W A V L Q L G W R P G W
F L D S P D R P W N P P T F S P A L L V V T E G D N
A T F T C S F S N T S E S F V L N W Y R M S P S N Q
T D K L A A F P E D R S Q P G Q D C R F R V T Q L
P N G R D F H M S V V R A R R N D S G T Y L C G A
I S L A P K L Q I K E S L R A E L R V T E R R A E V P
T A H P S P S P R P A G Q F Q T L V; SEQ ID NO: 5). In
some alternatives, the PD-1 is a mutated form of PD-1 and
comprises an amino acid sequence set forth in SEQ ID NO:
6 (M Q I P Q A P W P V V W A V L Q L G W R P G W
F L D S P D R P W N P P T F S P A L L V V T E G D N
A T F T C S F S N T S E S F H V V W H R E S P S G Q
T D T L A A F P E D R S Q P G Q D C R F R V T Q L P
N G R D F H M S V V R A R R N D S G T Y V C G V I
S L A P K I Q I K E S L R A E L R V T E R R A E V P T
A H P S P S P R P A G Q F Q T L V; SEQ ID NO: 6). In
some alternatives, the nucleic acid is a DNA or an RNA. In
some alternatives, the amino acid spacer comprises 1, 2, 3,
4, 5, 6, 7, 8, 9 or 10 amino acids, such as glycines, or a
number of amino acids, such as glycines, within a range
defined by any two of the aforementioned numbers. In some
alternatives, the amino acid spacer comprises at least 3
glycines. In some alternatives, the amino acid spacer comprises a sequence set forth in SEQ ID NO: 7 (GGGS; SEQ
ID NO: 7), SEQ ID NO: 8 (GGGSGGG; SEQ ID NO: 8) or
SEQ ID NO: 9 (GGG; SEQ ID NO: 9). In some alternatives,
the nucleic acid further comprises a fifth sequence encoding
a 2A linker, wherein the 2A linker is between the fusion
protein and a protein for co-expression. In some alternatives,
the 2A linker is a T2A linker, a P2A linker or an E2A linker.
In some alternatives, the fifth sequence comprises a nucleic
acid sequence encoding a T2A linker and comprises a
nucleic acid sequence set forth in SEQ ID NO: 10
(GGCGGCGGAGAGGGCAGAGGAAGTCTTCTAA-
CATGCGGTGACGTGGAGGAG
AATCCCGGCCCTAGG; SEQ ID NO: 10) and further
comprises a sequence encoding a protein for co-expression.
In some alternatives, the nucleic acid further comprises a
sixth sequence encoding an IRES sequence. In some alternatives, the nucleic acid further comprises a seventh
sequence encoding a marker. In some alternatives, the
marker is Her2tG or EGFRt. In some alternatives, the
nucleic acid further comprises an eighth sequence, wherein
the eighth sequence encodes a signal for protein secretion. In
some alternatives, PD-1 further comprises a signaling
domain for secretion. In some alternatives, the signal for
protein secretion is a GMCSF signaling sequence, PD-1
signaling sequence or CD19 signaling sequence. In some
alternatives, the GMCSF signaling sequence is encoded by
a nucleic acid sequence set forth in SEQ ID NO: 11
(atgatctcctggtgacaagccttctgctctgtgagttaccacacccagcat-
tcctcctgatccca; SEQ ID NO: 11). In some alternatives, the
PD-1 signaling sequence is encoded by a nucleic acid
sequence set forth in SEQ ID NO: 12 (ATGCA- GATCCCTCAGGCCCCTTGGCCTGTCGTGTGGGC-TGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13). In some alternatives, the vector comprises the nucleic acid of any one of the alternatives herein. In some alternatives, the vector is RNA or DNA.

In a seventh aspect, a method of manufacturing a fusion protein is provided. The method can comprise delivering the nucleic acid of anyone of the alternatives described herein or the expression vector of anyone of the alternatives described herein to a bacterial cell, mammalian cell or insect cell, growing the cell up in a culture, inducing expression of the fusion protein and purifying the fusion protein. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACAG-CTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCA-GATCCCTCAGGCCCCTTGGCCTGTCGTGTGGGC-TGTGCTGCAGCTGG GATGGCGGCCTGGCTGGTTTCTGGACAGCCCCG-ACAGACCCTGGAACCCCCT ACAT-TTTCCCCTGCCCTGCTGGTCGTGACCGAGGGCG-ACAATGCCACCTTCAC CTGTAGCTTCAGCAACACCAGCGAGAGCTTCGT-GCTGAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACCC-AGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence comprises a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence comprises a nucleic acid sequence set forth in SEQ ID NO: 12 (ATGCA-GATCCCTCAGGCCCCTTGGCCTGTCGTGTGGGC-TGTGCTGCAGCTGG GATGGCGG; SEQ ID NO: 12). In some alternatives, the CD19 signaling sequence comprises a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13). In some alternatives, the vector comprises the nucleic acid of any one of the alternatives herein. In some alternatives, the vector is RNA or DNA. In some alternatives, the inducing comprises adding IPTG, anhydrotetracycline, L-arabinose or rhamnose to the culture. In some alternatives, the cell is E. coli. In some alternatives, the cell is an insect-cell.

In an eighth aspect, a method of secreting the fusion protein of anyone of the alternatives described herein is provided. The method can comprise delivering to a subject the cell of anyone of the alternatives described herein or the composition of anyone of the alternatives described herein. The cell can comprise the nucleic acid of anyone of the alternatives described herein or the expression vector of anyone of the alternatives described herein. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACA-GCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCA-GATCCCTCAGGCCCCTTGGCCTGTCGTGTGGGC-TGTGCTGCAGCTGG GATGGCGGCCTGGCTGGTTTCTGGACAGCCCCG-ACAGACCCTGGAACCCCCT ACAT-TTTCCCCTGCCCTGCTGGTCGTGACCGAGGGCGA-CAATGCCACCTTCAC CTGTAGCTTCAGCAACACCAGCGAGAGCTTCGT- GCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (atgatctcctggtgacaagccttctgctctgtgagttaccacacccagcattcctcctgatccca; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG ATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector comprises the nucleic acid of any one of the alternatives herein. In some alternatives, the vector is RNA or DNA. In some alternatives, the cell is a bacterial cell or a mammalian cell, such as a lymphocyte or NK cell. In some alternatives, the cell is a bacterial cell, such as *E. coli*. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. The composition can comprise the cells of anyone of the alternatives described herein, or the cells manufactured by the methods of anyone of the alternatives described herein. The cell can comprise the nucleic acid of anyone of the alternatives described herein or the expression vector of anyone of the alternatives described herein. In some alternatives, the cell is a bacterial cell or a mammalian cell, such as a lymphocyte or NK cell. In some alternatives, the cell is a bacterial cell, such as *E. coli*. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the method of making the cell can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The expression vector can comprise the nucleic acid of anyone of the alternatives described herein. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. In some alternatives, the method further comprises administering to the subject an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the chimeric antigen receptor is specific for CD19. In some alternatives, the cell further comprises a nucleic acid encoding a chimeric antigen receptor.

In a ninth aspect, a method of increasing T-cell activity comprising administering an effective amount of the cell of anyone of the alternatives described herein or the composition anyone of the alternatives described herein, wherein the cells of the composition express a chimeric antigen receptor that comprises an antigen binding domain that binds to a tumor antigen expressed on a cancer cell, or the fusion protein of anyone of the alternatives described herein to a subject in need. The cell can comprise the nucleic acid of anyone of the alternatives described herein or the expression vector of anyone of the alternatives described herein. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGC-TGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTCCTCCTCTTCCTGACGCCGATG-GAAGT AAGG; SEQ ID NO: 13). In some alternatives, the vector comprises the nucleic acid of any one of the alternatives herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the chimeric antigen receptor is specific for CD19. In some alternatives, the composition can comprise the cells of anyone of the alternatives described herein, or the cells manufactured by the methods of anyone of the alternatives described herein. The cell can comprise the nucleic acid of anyone of the alternatives described herein or the expression vector of anyone of the alternatives described herein. The expression vector can comprise the nucleic acid of anyone of the alternatives described herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the chimeric antigen receptor is specific for CD19. In some alternatives, the cell further comprises a nucleic acid encoding a chimeric antigen receptor. In some alternatives, the method of making the cell can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The expression vector can comprise the nucleic acid of anyone of the alternatives described herein. In some alternatives, the expression vector is RNA or DNA. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the chimeric antigen receptor is specific for CD19. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. The fusion protein can be encoded by the nucleic acid of anyone of the alternatives provided herein or the vector of anyone of the alternatives provided herein. In some alternatives, the administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day.

In a tenth aspect, a method of decreasing immunosuppression in a tumor microenvironment is provided. The method can comprise administering an effective amount of the cell of anyone of the alternatives provided herein or the composition of anyone of the alternatives provided herein, wherein the cells of the composition express a chimeric antigen receptor that comprises an antigen binding domain that binds to a tumor antigen expressed on a cancer cell, or the fusion protein of anyone of the alternatives provided herein to a subject in need. In some alternatives, the chimeric antigen receptor is specific for CD19. The cell can comprise the nucleic acid of anyone of the alternatives described herein or the expression vector of anyone of the alternatives described herein. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGC-ACGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACA-GCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCA-GATCCCTCAGGCCCCTTGGCCTGTCGTGTGGGC-TGTGCTGCAGCTGG GATGGCGGCCTGGCTGGTTTCTGGACAGCCCCG- ACAGACCCTGGAACCCCCT ACATTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector comprises the nucleic acid of any one of the alternatives herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the chimeric antigen receptor is specific for CD19. In some alternatives, the cell further comprises a nucleic acid encoding a chimeric antigen receptor. In some alternatives, the composition can comprise the cells of anyone of the alternatives described herein, or the cells manufactured by the methods of anyone of the alternatives described herein. The cell can comprise the nucleic acid of anyone of the alternatives described herein or the expression vector of anyone of the alternatives described herein. The expression vector can comprise the nucleic acid of anyone of the alternatives described herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the chimeric antigen receptor is specific for CD19. In some alternatives, the method of making the cell can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The expression vector can comprise the nucleic acid of anyone of the alternatives described herein. In some alternatives, the vector is RNA or DNA. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. The fusion protein can be encoded by the nucleic acid of anyone of the alternatives provided herein or the vector of anyone of the alternatives provided herein. In some alternatives, the administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day.

In an eleventh aspect, a method of inhibiting, ameliorating, or treating cancer in a subject such as a human, that expresses a tumor antigen, is provided. The method can comprise administering an effective amount of the cell of anyone of the alternatives provided herein or the composition anyone of the alternatives provided herein, wherein the cells of the composition express a chimeric antigen receptor that comprises an antigen binding domain that binds to a tumor antigen expressed on a cancer cell, or the fusion protein of anyone of the alternatives provided herein to the subject. In some alternatives, the chimeric antigen receptor is specific for CD19. The cell can comprise the nucleic acid of anyone of the alternatives described herein or the expression vector of anyone of the alternatives described herein. The expression vector can comprise the nucleic acid of anyone of the alternatives described herein. The nucleic acid can have a first sequence, wherein the first sequence encodes a protein that modulates an immune response, a second sequence, wherein the second sequence encodes a spacer, such as an amino acid spacer e.g., a plurality of glycines, and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACAG-CTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPINs, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (atgatctcctggtgacaagccttctgctctgtgagttaccacacccagcattcctcctgatccca; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGC TGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector comprises the nucleic acid of any one of the alternatives herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the chimeric antigen receptor is specific for CD19. In some alternatives, the cell further comprises a nucleic acid encoding a chimeric antigen receptor. In some alternatives, the composition can comprise the cells of anyone of the alternatives described herein, or the cells manufactured by the methods of anyone of the alternatives described herein. The cell can comprise the nucleic acid of anyone of the alternatives described herein or the expression vector of anyone of the alternatives described herein. The expression vector can comprise the nucleic acid of anyone of the alternatives described herein. In some alternatives, the vector is RNA or DNA. In some alternatives, the cell is a bacterial cell or a mammalian cell, such as a lymphocyte or NK cell. In some alternatives, the cell is a bacterial cell, such as E. coli. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. In some alternatives, the chimeric antigen receptor is specific for CD19. In some alternatives, the method of making the cell can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The expression vector can comprise the nucleic acid of anyone of the alternatives described herein. In some alternatives, the vector is RNA or DNA. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. The fusion protein can be encoded by the nucleic acid of anyone of the alternatives provided herein or the vector of anyone of the alternatives provided herein. In some alternatives, the administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day.

BRIEF DESCRIPTION OF THE DRAWINGS

FIGS. 7A and 7B show that primary CD4 and CD8 T-cells can co-express a CAR and PD1:IFNα. (7A) Primary CD4 and CD8 T-cells were isolated from PBMCs using CD4 or CD8 microbeads, respectively. The CD4 and CD8 T-cells were selected up to 99% and 92.3% purity, respectively. (7B) Purified CD4 or CD8 T-cells were stimulated with CD3/CD28 microbeads for three days and then transduced with lentivirus containing the following: CD19scFv-IgG4hinge-CD28tm/41BB-zeta-T2A-Her2tG ($2^{nd}$ generation short spacer CD19CAR) and/or EGFRt-T2A-PD1:IFNα2a. The transduced CD4 and CD8 T-cells were then expanded (10-12 days) and subjected to purification using biotinylated Herceptin or Erbitux to select for Her2tG or EGFRt positive populations, respectively. The dual transduced CD4 or CD8 T-cells were subjected to a second round of purification 4 days later for the second selection marker (Her2tG first selection, EGFRt second selection). Results demonstrate that the dual transduced T-cells were >95% dual positive following selections.

DEFINITIONS

Figure 1:
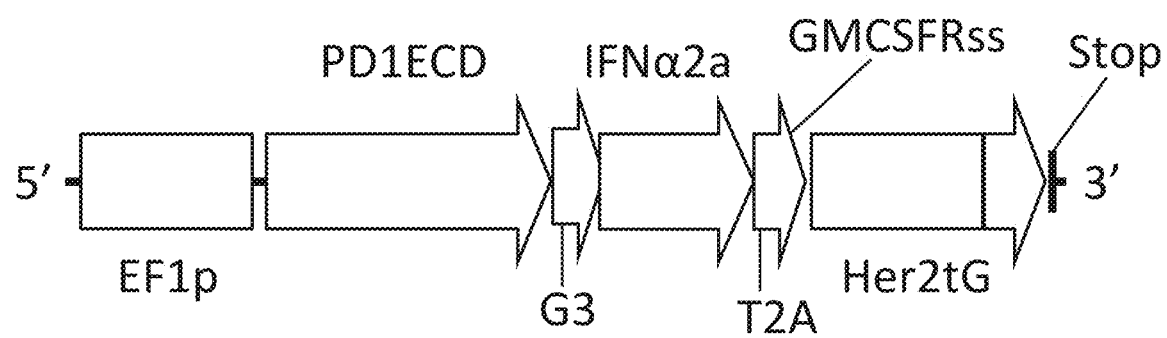
FIG. 1 shows a general schematic of PD-1:IFNα2a fusion protein.

Unless defined otherwise, all technical and scientific terms used herein have the same meaning as commonly understood by one of ordinary skill in the art to which the invention pertains.

As used herein, "a" or "an" may mean one or more than one.

"About" as used herein when referring to a measurable value is meant to encompass variations of ±20% or ±10%, more preferably ±5%, even more preferably ±1%, and still more preferably ±0.1% from the specified value.

"Nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives, a nucleic acid sequence encoding a fusion protein is provided. In some alternatives, the nucleic acid is RNA or DNA.

"Coding for" or "encoding" are used herein, and refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

A "nucleic acid sequence coding for a polypeptide" includes all nucleotide sequences that are degenerate versions of each other and that code for the same amino acid sequence. In some alternatives, a nucleic acid is provided, wherein the nucleic acid encodes a fusion protein. In the some alternatives described herein, the fusion protein comprises PD1 and IFNα2a. The PD1 component of the PD1:IFNα2a fusion protein can sequester the T-cell inhibitory interaction of PD1 with its ligand POL 1. These characteristics make the PD1:IFNα2a fusion protein a novel, molecular hub of antineoplastic function and an auspicious candidate to supplement solid tumor CAR therapy. The use of this protein can make CAR therapy more interactive against the immunosuppressive milieu found in solid tumors by eliciting stimulatory and suppressive functions to specific tumor-resident immune cell subsets. Secretion of the PD-1:IFNα2a fusion protein in CAR T-cells can be used to support T-cell activity, promote inflammatory cytokine production and decrease immunosuppression within the solid tumor microenvironment. The use of PD1-IFNα2a will have most use against solid tumors that express targets such as EGFRvIII, Her2, L1CAM, oaGD2, GD2, ROR1, B7H3, IL13Ra2 and EphA2, for example, where the tumor microenvironment plays a larger role in tumor progression.

"Vector," "Expression vector" or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as *E. coli*. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as *E. coli*.

As used herein, "fusion proteins" or "chimeric proteins" are proteins created through the joining of two or more genes that originally coded for separate proteins or portions of proteins. The fusion proteins can also be made up of specific protein domains from two or more separate proteins. Translation of this fusion gene can result in a single or multiple polypeptides with functional properties derived from each of the original proteins. Recombinant fusion proteins can be created artificially by recombinant DNA technology for use in biological research or therapeutics. Such methods for creating fusion proteins are known to those skilled in the art. Some fusion proteins combine whole peptides and therefore can contain all domains, especially functional domains, of the original proteins. However, other fusion proteins, especially those that are non-naturally occurring, combine only portions of coding sequences and therefore do not maintain the original functions of the parental genes that formed them. In some alternatives, a fusion protein is provided, wherein the fusion protein comprises an interferon and a PD-1 protein.

Alternative to the fusion of IFNα2a to PD1, IFNα2a can also be fused to other tumor resident antigens or secretable factors known to inhibit immunotherapeutic approaches. Without being limiting examples can include the soluble TGFbRII, antigen specific scFvs or homeostatic cytokines. The alternatives described herein can also test the ability to use T cells as a delivery vehicle for secreted, immunoregulatory proteins.

In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines.

Many whole gene fusions can be fully functional, and can be used, for example to replace an original peptide which can be missing in a biological system. Some, however, experience interactions between the two proteins that modify their functions. Beyond these effects, some gene fusions may cause regulatory changes that can alter when and where these genes can act. For partial gene fusions, the shuffling of different active sites and binding domains have potential to result in new proteins with novel functions. In some alternatives, a nucleic acid encoding a fusion protein is provided. In some alternatives, the fusion protein comprises a peptide that can modulate an immune response, an amino acid spacer or linker, such as a plurality of glycines, also referred to throughout as a glycine spacer, or flexible domains from the lambda phage, and an interferon or a portion thereof. In some alternatives, the interferon is IFN-α, IFNα2a, IFN-β, IFN-ε, IFN-κ or IFN-ω. In some alternatives, the interferon is IFNα2a. In some alternatives, the fusion protein comprises a protein or portion thereof that can modulate an immune response. In some alternatives, the protein is PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, the protein is PD-1, wherein PD-1 is a wild type PD-1 or a mutated or truncated form of PD-1A.

Alternative to the fusion of an interferon to PD1, an interferon can be fused to another tumor resident antigen or secretable factor that is known to inhibit immunotherapeutic approaches. In some alternatives herein, fusion protein is provided. In some alternatives, the fusion protein comprises an interferon. In some alternatives, the fusion protein further comprises TGFβRII or a portion thereof. In some alternatives, the fusion protein further comprises an antibody, or a portion thereof. In some alternatives, the fusion protein further comprises an scFv. In some alternatives, the fusion protein further comprises a homeostatic cytokine. Homeostatic cytokines control the cells of the immune system during immune surveillance processes.

In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines.

"Programmed cell death protein 1", also known as PD-1 and CD279 (cluster of differentiation 279), is a protein that in humans is encoded by the PDCD1 gene. PD-1 is a protein that functions as an immune checkpoint and plays a role in modulating the immune response, down regulating the immune system by preventing the activation of T cells to reduce autoimmunity and promote self-tolerance. PD-1 has an inhibitory effect of programming apoptosis in antigen specific T cells in the lymph nodes and simultaneously reducing apoptosis in regulatory T cells. PD-1 inhibitors can be used however to activate the immune system to attack tumors and can be used to treat some types of cancers. PD-1 has two ligands PD-L1 and PD-L2. Binding of PD-L1 to PD-1 allows the transmittal of an inhibitory signal, which reduces the proliferation of CD8+ T cells at lymph nodes. PD-L1 can also bind PD-1 on activated T cells, B cells and myeloid cells to modulate activation or inhibition. In some alternatives, a nucleic acid encoding a fusion protein is provided. The nucleic acid can have a first sequence, wherein the first sequence encodes a protein that modulates an immune response, a second sequence, wherein the second sequence encodes a spacer or linker, such as a glycine spacer also referred to as a plurality of glycines, and a third sequence, wherein the third sequence encodes an interferon. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, a 3' terminus of the first sequence is adjacent to a 5' terminus of the second sequence and a 3' terminus of the second sequence is adjacent to a 5' terminus of the third sequence. The first sequence, second sequence and third sequence can be in any order in the nucleic acid.

Mutated forms of PD-1 have also been described by Lazar-Molnar et al. (2008) and Maute et al. (2015) (Lázár-Molnár et al. Proc Natl Acad Sci USA. 2008 Feb. 19; 105(7):2658-63, Lázár-Molńar et al. Proc Natl Acad Sci USA. 2008 Jul. 29; 105(30):10483-8, and Proc Natl Acad Sci USA. 2015 Nov. 24; 112(47); all hereby incorporated by reference in their entireties). Lázár-Molńar et al. describes a PD-1 with one point mutation, which has the amino acid sequence amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). Maute et al. describes a PD-1 with 11 point mutations, in which the PD-1 mutant has the amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, a nucleic acid encoding a fusion protein is provided. In some alternatives, the nucleic acid comprises a first sequence, wherein the first sequence encodes a protein that modulates an immune response, a second sequence, wherein the second sequence encodes a spacer or linker, such as a glycine spacer, and a third sequence, wherein the third sequence encodes an interferon. In some alternatives, the first sequence encodes a PD-1 protein, a PD-1 mutant or a functional portion thereof. In some alternatives, the first sequence comprises a nucleic acid sequence set forth in SEQ ID NO: SEQ ID NO: 3 (ATGCA-GATCCCTCAGGCCCCTTGGCCTGTCGTGTGGGC-TGTGCTGCAGCTGG GATGGCGGCCTGGCTGGTTTCTGGACAGCCCCG-ACAGACCCTGGAACCCCCCT ACAT-TTTCCCCTGCCCTGCTGGTCGTGACCGAGGGCG-ACAATGCCACCTTCAC CTGTAGCTTCAGCAACACCAGCGAGAGCTTCGT-GCTGAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACCC-AGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence.

The PD1 mutants described herein are affinity matured mutants created either by site-directed mutagenesis (the A99L mutant) or by directed evolution (HAC-V mutant). Both mutants display a greater ability to bind their ligand PD-L1 and may therefore elicit a better ability to inhibit negative PD1 signals inside the tumor microenvironment that can occur on therapeutic T cells by acting as a decoy receptor separate to PD1 found on the T cells. The A99L mutant confers a 3-fold increase in affinity and the HAC-V mutant confers a ~35000-fold increase in affinity to PDL1 relative to wild-type PD1. Mutated forms of protein can be manufactured by standard site directed mutagenesis protocols for mutating nucleic acids to encode a protein with point mutations and can be appreciated by those skilled in the art.

A "single-chain variable fragment," (scFv) is a fusion protein that can have variable regions of the heavy (VH) and light chains (VL) of immunoglobulins, connected with a short linker peptide of ten to 25 amino acids. The short linker peptide can comprise 10, 11, 12, 13, 14, 15, 16, 17, 18, 19, 20, 21, 22, 23, 24, 25 amino acids or any number of amino acids in between a range defined by any two aforementioned values. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. The scFv can be specific for an antigen. "Antigen" or "Ag" as used herein refers to a molecule that provokes an immune response. This immune response can involve either antibody production, or the activation of specific immunologically-competent cells, or both. An antigen can be generated, synthesized, produced recombinantly or can be derived from a biological sample. Such a biological sample can include, but is not limited to a tissue sample, a tumor sample, a cell or a biological fluid such, for example, blood, plasma or ascites fluid. In some alternatives herein, a composition is provided, wherein the composition comprises cells manufactured by any one of the alternative methods herein. In some alternatives, the cells comprise a chimeric antigen receptor, wherein the chimeric antigen receptor comprises an scFv that is specific for an antigen.

"Antigen specific binding domains" can include protein or protein domains that can specifically bind to an epitope on a protein at a low or high binding affinity (μM to mM binding capacity). In some alternatives, the fusion protein comprises a protein or portion thereof that can modulate an immune response. In some alternatives, the protein comprises an antigen specific binding domain.

In some alternatives, the fusion protein comprises PD-1. In some alternatives, the fusion protein further comprises IFNα2a. Secretion of the PD-1:IFNα2a fusion protein in CAR T-cells can be used to support T-cell activity, promote inflammatory cytokine production and decrease immunosuppression within the solid tumor microenvironment. The use of PD1-IFNα2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression.

"Extracellular domains" are protein or receptor domains that protrude from the outer membrane of a cell organelle and a cell. Usually direct contacts between extracellular domains of membrane proteins with its specific ligand are required for receptor activation and cell signaling.

DARPins (designed Ankyrin repeat proteins) are genetically engineered antibody mimetic proteins typically exhibiting highly specific and high-affinity target protein binding. They are derived from natural ankyrin proteins and consist of at least three, usually four or five repeat motifs of these proteins. A DARPin can have several clinical benefits by overcoming the limitation of conventional therapeutic approaches by enabling the targeting many disease pathways. DARPin fusions are also beneficial because they can be made to resist aggregation. DARPins can also be designed to act as receptor agonists, antagonists, inverse agonists, enzyme inhibitors or a target protein binder.

In some alternatives, the fusion protein comprises a protein or portion thereof that can modulate an immune response. In some alternatives, the protein comprises a DARPin. In some alternatives, the fusion protein comprises an interferon fused to a DARPin. In some alternatives, the interferon is IFN-α, IFNα2a, IFN-0, IFN-ε, IFN-κ or IFN-ω. In some of the alternative fusion proteins herein, the DARPin is a receptor agonist, antagonist, inverse agonist, enzyme inhibitor or a target protein binder.

Secretion of a fusion protein in CAR T-cells can be used to support T-cell activity, promote inflammatory cytokine production and decrease immunosuppression within the solid tumor microenvironment. The use of a fusion protein such as PD1-IFNα2a, can be used against solid tumors that express targets where the tumor microenvironment plays a larger role in tumor progression. Without being limiting, examples of targets are EGFRvIII, Her2, L1CAM, oaGD2, GD2, ROR1, B7H3, IL13Ra2 and/or EphA2, for example.

"Her2" as described herein, is the receptor tyrosine-protein kinase erbB-2, also known as CD340 (cluster of differentiation 340), proto-oncogene Neu, Erbb2 (rodent), or ERBB2. It is a member of the human epidermal growth factor receptor (HER/EGFR/ERBB) family and has been known to play an important role in the development and progression of certain aggressive types of breast cancer. In some alternatives, the fusion protein comprises a protein or portion thereof that can modulate an immune response. In some alternatives, the fusion protein comprises a protein that binds Her2. In some alternatives, a cell is provided, wherein the cell comprises a chimeric antigen receptor. In some alternatives, the chimeric antigen receptor is specific for HER2.

"ROR1" or tyrosine-protein kinase transmembrane receptor ROR1, also known as neurotrophic tyrosine kinase, receptor-related 1 (NTRKR1), is an enzyme that in humans is encoded by the ROR1 gene. ROR1 is a member of the receptor tyrosine kinase-like orphan receptor (ROR) family and has been shown to be expressed on ovarian cancer stem cells. In some alternatives, the fusion protein comprises a protein or portion thereof that modulates an immune response. In some alternatives, the fusion protein comprises a protein that binds ROR1. In some alternatives, a cell is provided, wherein the cell comprises a chimeric antigen receptor. In some alternatives, the chimeric antigen receptor is specific for ROR1.

The "extracellular matrix," (ECM) as described herein, comprises a collection of extracellular molecules secreted by cells that provides structural and biochemical support to the surrounding cells. The composition of ECM varies between multicellular structures; however, cell adhesion, cell-to-cell communication and differentiation are common functions of the ECM. Without being limiting, proteins of the ECM can include embryonal fibronectin, fibronectin, laminin and collagen. In some alternatives, the fusion protein comprises a protein or portion thereof that modulates an immune response. In some alternatives, the protein comprises an extracellular matrix protein. In some alternatives, the extracellular matrix protein is embryonal fibronectin, fibronectin, laminin or collagen "Glycine spacer" or "glycine linker" can be used to separate one protein domain from another and can range in length from 2, 4, 6, 8, or 10 glycines or any number of glycines that are within a range between any two aforementioned values. A glycine spacer is an amino acid spacer and can be modified in order to increase the binding affinity of one or more binding portions in a fusion protein. Additionally, a glycine spacer may be modified in length in order to prevent interactions between different binding modalities of a fusion protein. In some alternatives described herein, the glycine spacer comprises 1, 2, 3, 4, 5, 6, 7, 8, 9 or 10 glycines or a number of glycines within a range defined by any two of the aforementioned numbers. In some alternatives, the glycine spacer comprises at least 3 glycines. In some alternatives, the glycine spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9).

In some alternatives, a glycine spacer is modified if during testing, there is reduced activity. The glycine spacer, for example, can be varied in length in order to facilitate proper protein folding and protein activity.

"Immune response" as described herein, are the processes of the immune system that are used to prevent or limit an infection or a disease upon recognition of a pathogen such as viruses or bacteria or the presence of abnormal cells such as cancer cells. Examples of an immune response can include but are not limited to inflammation, triggering of the innate immune system, activation of the complement system, triggering of cellular barriers, triggering of the natural killer cells and triggering of the adaptive immune system.

[0062] Inflammation is an immune response in which growth factors and cytotoxic factors are released. Cytokines and other chemicals recruit immune cells to the site of infection and promote healing of any damaged tissue following the removal of pathogens. In some alternatives, a fusion protein is provided, wherein the fusion protein comprises a peptide that modulates an immune response. In some alternatives, the fusion protein promotes an inflammatory response. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines.

"Interferons" are a group of signaling proteins that are produced and released by cells in response to pathogens, viruses, bacteria, parasites and signals from foreign cells and tumor cells in order to increase anti-viral defenses. In some alternatives described herein, a nucleic acid encoding a fusion protein is provided, wherein the fusion protein comprises an interferon or a portion thereof. In some alternatives, the interferon is IFN-α, IFNα2a, IFN-β, IFN-ε, IFN-κ or IFN-ω. In some alternatives, the interferon is IFNα2a. In some alternatives, the sequence encoding the interferon comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1).

The IFN-α proteins are produced by leukocytes and are mainly involved in innate immune response against viral infection. They are 13 subtypes: IFNA1, IFNA2, IFNA4, IFNA5, IFNA6, IFNA7, IFNA8, IFNA10, IFNA13, IFNA14, IFNA16, IFNA17, and IFNA21. In some alternatives described herein, a nucleic acid encoding a fusion protein is provided, wherein the fusion protein comprises an interferon or a functional portion thereof. In some alternatives, the interferon is IFNA1, IFNA2, IFNA4, IFNA5, IFNA6, IFNA7, IFNA8, IFNA10, IFNA13, IFNA14, IFNA16, IFNA17 or IFNA21 or a functional portion thereof.

The IFN-β proteins are produced by fibroblasts. They have antiviral activity that is involved mainly in innate immune response. Two types of IFN-β have been described, IFN-β1 (IFNB1) and IFN-β3 (IFNB3). In some alternatives described herein, a nucleic acid encoding a fusion protein is provided, wherein the fusion protein comprises an interferon or a functional portion thereof. In some alternatives, the interferon is IFN-β1 (IFNB1) or IFN-β3 (IFNB3) or a functional portion thereof.

A "promoter" is a region of DNA that initiates transcription of a specific gene. The promoters can be located near the transcription start site of a gene, on the same strand and upstream on the DNA (the 5'region of the sense strand). The promoter can be a conditional, inducible or a constitutive promoter. The promoter can be specific for bacterial, mammalian or insect cell protein expression. In some alternatives, wherein a nucleic acid encoding a fusion protein is provided, the nucleic acid further comprises a promoter sequence. In some alternatives, the promoter is specific for bacterial, mammalian or insect cell protein expression. In some alternatives, the promoter is a conditional, inducible or a constitutive promoter.

"Conditional" or "Inducible" as used herein refers to a nucleic acid construct that includes a promoter that provides for gene expression in the presence of an inducer and does not substantially provide for gene expression in the absence of the inducer. Without being limiting, examples of inducible promoters for mammalian expression constructs include tetracycline, ecdysone, streptogramins, macrolides or doxycycline inducible promoters. Without being limiting, examples of inducible promoters for bacterial expression constructs include but are not limited to a T7 promoter, lac promoter, trc promoter, tac promoter, tetA promoter, araBAD promoter or a rhaP$_{BAD}$ promoters. Without being limiting, insect-derived promoters include but are not limited to pB2 and polyhedrin promoters. In some alternatives, wherein a nucleic acid encoding a fusion protein is provided, the nucleic acid further comprises a promoter sequence. In some alternatives, the promoter is an inducible promoter. In some alternatives, the promoter is an inducible promoter for bacterial protein expression. In some alternatives, the inducible promoter for bacterial expression is a T7 promoter, lac promoter, trc promoter, tac promoter, tetA promoter, araBAD promoter or a rhaP$_{BAD}$ promoter. In some alternatives, the promoter is an inducible promoter for expression in a mammalian system. In some alternatives, wherein the promoter is an inducible promoter for mammalian expression, the inducible promoter is a tetracycline, ecdysone, streptogramins, macrolides or doxycycline inducible promoter. In some alternatives, the promoter is for protein expression in an insect cell. In some alternatives, the promoter is a pB2 or a polyhedrin type promoter. In some alternatives, the bacterial promoter is inducible by IPTG, anhydrotetracycline, L-arabinose or rhamnose. In some alternatives, wherein the promoter is for mammalian cell protein expression, the promoter is regulated by a drug. In some alternatives, the drug is tamoxifen. In some alternatives, wherein the promoter is for mammalian cell protein expression, the promoter is regulated by a CAR-dependent signal. In some alternatives, the promoter is an NFAT regulated promoter system.

Systemic administration of IFNα2a can cause adverse effects in normal tissue. In some alternatives, wherein the systemic administration of PD1:IFNα2a fusion can cause adverse effects in normal tissue. If the PD1:IFNα2a also causes off-target toxicities expression can be regulated by control under a promoter, such as a drug regulatable promoter or by CAR-dependent signaling (e.g. tamoxifen or NFAT regulated promoter systems).

"Constitutive" as used herein refer to the nucleic acid construct that includes a promoter that is constitutive, and thus provides for expression of a polypeptide that is continuously produced. In some alternatives, wherein a nucleic acid for expressing a fusion protein is provided, the nucleic acid further comprises a promoter for protein expression in a bacterial, mammalian or an insect cell. In some alternatives, the promoter is EF-1 Promoter (EF1P).

As described, the EF1P promoter is a constitutive promoter of human origin that can drive ectopic gene expression in vivo and in vitro. In some alternatives, an EF1P promoter drives the expression of the fusion protein. In some alternatives, the sequence encoding the promoter comprises the nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACAC-AGCTG; SEQ ID NO: 2).

Promoter systems can also be regulated by a drug. Without being limiting, a drug that can be used to regulate a promoter can include tamoxifen. "Tamoxifen," as described herein, is an estrogen antagonist/partial agonist that is an FDA-approved and commercially available drug. It is taken orally and can be administered on a daily basis over an extended period of time. Tamoxifen has a proven safety record, favorable pharmacokinetic profile, excellent tissue distribution and a low partition coefficient between the extracellular space and cytosol. Other drugs can be selected based on safety record, favorable pharmacokinetic profile, and excellent tissue distribution, a low partition coefficient between the extracellular space and cytosol, and/or low toxicities.

In some alternatives, the system employs a synthetic transcriptional regulator, which, in the presence of tamoxifen, binds a synthetic promoter upstream of a transgene to induce expression. The tamoxifen regulated transcription factor ("TamR-tf", also designated "HEA3") is a chimeric transcription factor composed of human subunits including the N-terminal DNA binding domain of Hepatocyte Nuclear Factor 1-alpha (HNF-1α) fused in frame to the mutant tamoxifen-specific ligand binding domain of the estrogen receptor ligand binding domain (ER-LBD), that is in turn fused to the p65 activation domain of NF-κB (p65). The mutant tamoxifen-specific ligand binding domain of the estrogen receptor ligand binding domain (ER-LBD) is found at amino acids 282-595 of the TamR-tf and has a mutation at position 521. Further changes can be made to the transcriptional activator to increase the properties of the transcription factor including, without limitation, altering one or more amino acids in the estrogen receptor ligand binding domain to increase the affinity of the factor for estrogen analogs and altering one or more amino acids in the p65 transactivating domain.

In the absence of tamoxifen, TamR-tf is excluded from the nucleus by binding of cytosolic heat-shock protein 90 (HSP90) to the tamoxifen binding active site and transgene expression is in the "OFF" state. Nanomolar concentrations of cytosolic tamoxifen actively out competes HSP90 for ER-LBD binding, resulting in TamR-tf translocation to the nucleus. Upon nuclear translocation, TamR-tf is readily available to bind its restricted synthetic promoter (e.g. 7×HBD/EF1αp). In the presence of tamoxifen, binding of TamR-tf to 7×HBD/EF lap promoter induces the "ON" state of transgene expression. In some alternatives, this transcriptional regulator can be modified to provide for a varying level of control of transgene expression. Amino acid substitutions in the LBD of TamR-tf permit selective responsiveness to tamoxifen and its metabolites, where 4-hydroxy tamoxifen (4-OHT) is the most pharmacologically active metabolite, in regards to TamR-tf activity, while lacking interaction with endogenous estrogen. In some alternatives, a nucleic acid encoding a fusion protein is provided, wherein the nucleic acid comprises a promoter regulated by a drug. In some alternatives, the drug includes tamoxifen, its metabolites, analogs, and pharmaceutically acceptable salts and/or hydrates or solvates thereof.

Tamoxifen, CAS RN: 10540-29-1, is also known as 2-(4-((1Z)-1,2-diphenyl-1-butenyl)phenoxy)-N,N-dimethyl-ethanamine, or (Z)-2-(para-(1,2-Diphenyl-1-butenyl)phenoxy)-N,N-dimethylamine (IUPAC), and has a molecular formula of $C_{26}H_{29}NO$, M.W. 371.52. Tamoxifen is a Selective Estrogen Receptor Modulator with tissue-specific activities. Tamoxifen acts as an anti-estrogen (inhibiting agent) agent in the mammary tissue, but as an estrogen (stimulating agent) in cholesterol metabolism, bone density, and cell proliferation in the endometrium. Tamoxifen is frequently administered orally as a pharmaceutically acceptable salt. For example, Tamoxifen citrate (RN 54965-24-1, M.W. 563.643) is indicated for treatment of metastatic breast cancer, and as an adjuvant for the treatment of breast cancer in women following mastectomy axillary dissection, and breast irradiation.

Metabolites of tamoxifen in rat, mouse and human breast cancer patients, including major metabolites N-desmethyl-tamoxifen (RN 31750-48-8, M.W. 357.494) and 4-hydroxytamoxifen (4-OHT) (RN 68392-35-8, M.W. 387.52, Afimoxifene), are disclosed in Robinson et al., Metabolites, pharmacodynamics, and pharmacokinetics of tamoxifen in rats and mice compared to the breast cancer patient. Drug Metab Dispos January 1991 19:36-43, which is incorporated by reference herein in its entirety. Additional cytochrome P-450 metabolites are disclosed in Crewe et al., 2002, including cis-4-hydroxytamoxifen (RN 174592, M.W. 387.52; Afimoxifene, E-isomer), and 4'-hydroxytamoxifen ((Z)-4-(1-(4-(2-(dimethylamino)ethoxy)phenyl)-1-phenyl-but-1-en-2-yl)phenol). See Crewe et al., 2002, Metabolism of Tamoxifen by recombinant human cytochrome P-450 enzymes: Formation of the 4-hydroxy, 4'-hydroxy and N-desmethyl metabolites and isomerization of trans-4-hydroxytamoxifen, Drug Metab Dispos, 30(8): 869-874, FIG. 1, which is incorporated herein by reference.

Compounds with structural similarity to tamoxifen include, but are not limited to, cis-tamoxifen (RN 13002-65-8, M.W. 371.521), 4-methyltamoxifen (RN 73717-95-5, M.W. 385.548), N-desmethyltamoxifen (RN 31750-48-8, M.W. 357.494), (Z)-desethyl methyl tamoxifen (RN 15917-50-7, M.W. 357.494), (E)-desethyl methyl tamoxifen (RN 31750-45-5, M.W. 357.494), trans-4-hydoxytamoxifen (RN 68047-06-3, M.W. 387.52), Afimoxifene (RN 68392-35-8, M.W. 387.52, 4-hydroxytamoxifen), Afimoxifene, E-isomer (RN 174592-47-3, M.W. 387.52), 4-chlorotamoxifen (RN 77588-46-6, M.W. 405.966), 4-fluorotamoxifen (RN 73617-96-6, M.W. 389.511), Toremifene (RN 89778-26-7, M.W. 405.966), desethyl tamoxifen (RN 19957-51-8, M.W. 343.47), (E)-desethyl tamoxifen (RN 97151-10-5, M.W. 343.47), (Z)-desethyl tamoxifen (RN 97151-11-6, M.W. 343.47), Miproxifene (RN 129612-87-9, M.W. 429.6), 2-(p-(beta-ethyl-alpha-phenylstyryl)phenoxy)triethylamine (RN 749-86-0, M.W. 399.575), Droloxifene (RN 82413-20-5, M.W. 387.52), 4-iodo-tamoxifen (RN 116057-68-2, M.W. 497.413), dihydrotamoxifen (RN 109640-20-2, M.W. 373.537), (E)-N,N-dimethyl-2-(4-(1-(2-methylphenyl)-2-phenyl-1-butenyl)phenoxy)ethanamine (RN 97150-96-4, M.W. 385.548), or 4-hydroxytoremifene (RN 110503-62-3, M.W. 421.965); and/or pharmaceutically acceptable salts and/or hydrates or solvates thereof.

For example, citrate salts of tamoxifen, or citrate salts of compounds with structural similarity to tamoxifen, include, but are not limited to tamoxifen citrate (RN 54965-24-1, M.W. 563.64), 2-(p-(1,2-diphenyl-1-butenyl)phenoxy)-N, N-dimethylethylamine citrate (RN 7244-97-5, 563.64), (E)-tamoxifen citrate (RN 76487-65-5, M.W. 563.64), Toremifene citrate (RN 89778-27-8, M.W. 598.088), Droloxifene citrate (RN 97752-20-0, M.W. 579.64), 2-(p-(1,2-bis(p-methoxyphenyl)-1-butenyl)phenoxy)triethylamine citrate (RN 42920-39-8, M.W. 651.748), 2-(4-(1,2-diphenylethenyl)phenoxy)-N,N-diethyl-ethanamine 2-hydroxy-1,2,3-propanetricarboxylate (RN 40297-42-5, M.W. 563.643), 2-(p-(alpha-phenylstyryl)phenoxy)triethylamine citrate (RN 102433-95-4, M.W. 563.64), 2-(p-(2-(p-methoxyphenyl)-1-phenyl-1-butenyl)phenoxy)triethylamine citrate (1:1) (RN 42824-34-0, M.W. 637.72), 2-(p-(1-(p-methoxyphenyl)-2-phenylpropenyl)phenoxy)triethylamine citrate (RN 13554-24-0, M.W. 607.696), 2-(p-(alpha-(p-methoxyphenyl)styryl)phenoxy)triethylamine citrate monohydrate (RN 13542-71-7, M.W. 593.669), 2-(p-(p-methoxy-alpha-phenylphenethyl) phenoxy)triethylamine citrate (RN 16421-72-0, M.W. 595.685), alpha-(p-(2-(diethylamino) ethoxy)phenyl)-beta-ethyl-p-methoxy-alpha-phenylphenethyl alcohol citrate (1:1) (RN 35263-93-5, M.W. 639.737), 1-(p-(2-(diethylamino)ethoxy)phenyl)-2-(p-methoxyphenyl)-1-phenylethanol citrate (M.W. 611.68), alpha-p-(2-(diethylamino)ethoxy)phenyl)-beta-ethyl-alpha-(p-hydroxyphenyl)-p-methoxyphenethyl alcohol citrate (RN 35263-96-8, M.W. 655.737), and/or 2-(p-(p-methoxy-alpha-methylphenethyl)phenoxy)-triethylamine citrate (RN 15624-34-7, M.W. 533.614).

In some alternatives, an affective amount of the drug for inducing expression is an amount that provides for an increase in transgene expression over uninduced and/or basal level of expression. In some alternatives, this amount can be readily determined by using known dosages and pharmacokinetic profile of the drug.

In some alternatives, the inducible promoter has a low level of basal activity. In some alternatives, wherein a lentiviral vector is used, the level of basal activity in uninduced cells is 20%, 15%, 10%, 5%, 4%, 3%, 2%, 1% or less, as compared to when cells are induced to express the gene. The level of basal activity can be determined by measuring the amount of the expression of the transgene (e.g. marker gene) in the absence of the inducer (e.g. drug) using flow cytometry. In some alternatives described herein a marker protein such as Her2tg or EGFRt is used for determination of expression.

In some alternatives, the inducible promoter provides for a high level of induced activity, as compared to uninduced or basal activity. In some alternatives, the level of activity in the induced state is 2, 4, 6, 8, or 10 fold or greater than the activity level in the uninduced state. In some alternatives, transgene expression under control of the inducible promoter is turned off in the absence of a transactivator in less than 10, 8, 6, 4, 2, or 1 days excluding 0 days.

In some alternatives, an inducible promoter is designed and/or modified to provide for a low level of basal activity, a high level of inducibility, and/or a short time for reversibility. In some alternatives, the inducible promoter is the 7×HBD/mE1b promoter. For example, in the 7×HBD/mE1b promoter, mutations can be made to enhance the binding of the transcriptional activator.

As described herein, the "NFAT regulated promoter system" is a promoter activated by NFAT. The NFAT family of transcription factors encompasses five proteins evolutionarily related to the Rel/NFκB family (Chytil and Verdine 1996; Graef et al. 2001b; incorporated by reference in its entirety herein). NFAT activates transcription of a large number of genes during an effective immune response (Rao et al. 1997; Kiani et al. 2000; Serfling et al. 2000; Macian et al. 2001; hereby expressly incorporated by reference in its entirety). In some alternatives, wherein a nucleic acid encoding a fusion protein is provided, the nucleic acid further comprises a promoter sequence. In some alternatives, the promoter is an inducible promoter. In some alternatives, the promoter is induced by a member of the NFAT protein family. The promoter can be used to induce the protein and to control expression if the fusion protein causes off-target toxicities.

"2A linker" as described herein, is a self-cleaving sequence that can be used to separate each element of the nucleic acid, such as sequences encoding one protein domain from another. In some alternatives, wherein a nucleic acid encoding a fusion protein is provided, the nucleic acid further comprises a sequence encoding a 2A linker. In some alternatives, the 2A linker is a T2A linker, an E2A linker or a P2A linker. In some alternatives, the T2A linker is between the fusion protein and a protein for co-expression.

The "IRES" sequence (internal ribosome entry site), as described herein, is a nucleotide sequence that can allow translation initiation in the middle of a messenger RNA (mRNA) sequence as part of the greater process of protein synthesis. In eukaryotes, translation can be initiated only at the 5' end of the mRNA molecule, since 5' cap recognition is required for the assembly of the initiation complex. The location for these sites is often in the 5'UTR, but can occur in many different places in an mRNA.

The "E2A" sequence, as described herein, encodes transcription factors known to play a critical role in the regulation of lymphocyte development. E2A proteins are highly expressed in developing lymphoid cells and are required for the initiation of B cell development in the bone marrow. In some alternatives, wherein a nucleic acid encoding a fusion protein is provided, the nucleic acid further comprises an E2A sequence.

The "P2A" sequence, as described herein, is a self-cleaving 2A peptide. In some alternatives, wherein a nucleic acid encoding a fusion protein is provided, the nucleic acid further comprises a P2A sequence.

A "marker sequence," as described herein, encodes a protein that is used for selecting or tracking a protein or cell that has a protein of interest. In the alternatives described herein, the fusion protein provided can comprise a marker sequence that can be selected in experiments, such as flow cytometry. In some alternatives, the marker is the protein Her2tG or EGFRt.

A "signal sequence" for secretion, can also be referred to as a "signal peptide." The signal peptide can be used for secretion efficiency and in some systems it is recognized by a signal recognition particle which halts translation and directs the signal sequence to a SRP receptor for secretion. In some alternatives of the fusion proteins provided herein, the fusion protein further comprises a signal sequence. In some alternatives, of the nucleic acid encoding a fusion protein, the nucleic acid comprises a sequence encoding a signal sequence. In some alternatives, the signaling sequence is a GMCSF signaling sequence, PD-1 signaling sequence or a CD19 signaling sequence. In some alternatives, the nucleic acid encoding the GMCSF signaling sequence comprises a nucleic acid sequence set forth in SEQ ID NO: 11 (atgatctcctggtgacaagccttctgctctgtgagttac-cacacccagcattcctcctgatccca; SEQ ID NO: 11). In some alternatives, the nucleic acid encoding the PD-1 signaling sequence comprises a nucleic acid sequence set forth in SEQ ID NO: 12 (ATGCA- GATCCCTCAGGCCCCTTGGCCTGTCGTGTGGGC-TGTGCTGCAGCTGG GATGGCGG; SEQ ID NO: 12). In some alternatives, the nucleic acid encoding the CD19 signaling sequence comprises a nucleic acid sequence set forth in SEQ ID NO: 13 (ATGCCCCTCCCA-GACTTCTCTTTTTCCTCCTCTTCCTGACGCCGATG-GAAGT AAGG; SEQ ID NO: 13).

As described herein, the "tumor microenvironment" (TME) is the surrounding microenvironment that constantly interacts with tumor cells, which is conducive to allow cross-talk between tumor cells and its environment. A tumor microenvironment plays a role in disrupting the cancer immunity cycle and plays a critical role in multiple aspects of cancer progression. For example, the TME can decrease drug penetration, confer proliferative and anti-apoptotic advantages to surviving cells, facilitate resistance without causing genetic mutations and epigenetic changes, and collectively modify disease modality and distort clinical indices. Without being limiting, the tumor microenvironment can include the cellular environment of the tumor, surrounding blood vessels, immune cells, fibroblasts, bone marrow derived inflammatory cells, lymphocytes, signaling molecules and the extracellular matrix. The tumor environment can include tumor cells or malignant cells that are aided and influenced by the tumor microenvironment to ensure growth and survival. The tumor microenvironment can also include tumor-infiltrating immune cells, such as lymphoid and myeloid cells, which can stimulate or inhibit the antitumor immune response and stromal cells such as tumor-associated fibroblasts and endothelial cells that contribute to the tumor's structural integrity. Without being limiting, stromal cells include cells that make up tumor-associated blood vessels, such as endothelial cells and pericytes, which are cells that contribute to structural integrity (fibroblasts), as well as tumor-associated macrophages (TAMs) and infiltrating immune cells including monocytes, neutrophils (PMN), dendritic cells (DCs), T and B cells, mast cells, and natural killer (NK) cells. The stromal cells make up the bulk of tumor cellularity while the dominating cell type in solid tumors is the macrophage. In some alternatives described herein, a fusion protein is provided wherein the fusion protein is used for administration into a tumor microenvironment.

"Chimeric receptor" or "chimeric antigen receptor," as used herein refers to a synthetically designed receptor comprising a ligand binding domain of an antibody or other protein sequence that binds to a molecule associated with the disease or disorder and is linked via a spacer domain to one or more intracellular signaling domains of a T-cell or other receptors, such as a costimulatory domain. In some alternatives, a cell is manufactured wherein the cell comprises a nucleic acid encoding a fusion protein and wherein the cell comprises a chimeric antigen receptor. In some alternatives, the chimeric antigen receptor comprises a ligand binding domain that is specific for a tumor surface molecule or protein. In some alternatives, the chimeric antigen receptor comprises an scFv that can recognize an epitope on a cancer cell. In some alternatives, the scFv is specific for CD19.

"CD19," as described herein, is a protein encoded by the CD19 gene and resides on the surfaces of B-cells. CD19 has been implicated in several autoimmune diseases and can be useful as a treatment target. In some alternatives herein, a cell is provided, wherein the cell comprises a chimeric antigen receptor. In some alternatives, the chimeric antigen receptor is specific for CD19.

"Macrophage inflammatory proteins," (MIP) as described herein is a family of proteins that belong to the family of chemotactic cytokines known as chemokines. Humans have two major forms, MIP-1α and MIP-1β that are now officially named CCL3 and CCL4, respectively. MIP-1α and MIP-1β are produced by macrophages after they are stimulated with toxins, such as bacterial endotoxins. MIPs are crucial for immune responses towards infection and inflammation. MIPs can activate human granulocytes (neutrophils, eosinophils and basophils) which can lead to acute neutrophilic inflammation. They also induce the synthesis and release of other pro-inflammatory cytokines such as interleukin 1 (IL-1), IL-6 and TNF-α from fibroblasts and macrophages. In some alternatives herein, the fusion protein PD1:IFnα2a stimulates the production of MIP-1a. In some alternatives herein, the fusion protein PD1:IFnα2a stimulates the production of MIP-1b.

"CXCL9," as described herein, is a small cytokine belonging to the CXC chemokine family that is also known as "Monokine induced by gamma interferon" (MIG). CXCL9 is a T-cell chemoattractant, and can be induced by IFN-γ. CXCL9 can elicit its chemotactic functions by interacting with the chemokine receptor CXCR3. In a recent study, CXCL9 was shown to induce chemotaxis and chemorepulsion through CXCR-3 mediated activation of melanoma cells (Amatschek et al.). In some alternatives herein, a fusion protein is provided, wherein the fusion protein stimulates the production of a cytokine. In some alternatives, the cytokine is CXCL9. In some alternatives, the fusion protein comprises PD1. In some alternatives, the fusion protein comprises IFnα2a.

"CXCL10," as described herein, is also known as "Interferon gamma-induced protein 10" (IP-10) or "small-inducible cytokine B10." CXCL10 can be secreted by several cell types in response to IFN-γ. Without being limiting, these cell types can include monocytes, endothelial cells and fibroblasts, for example. CXCL10 has been attributed to several roles, such as chemoattraction for many cells, such as monocytes/macrophages, T cells, NK cells, and dendritic cells for example. Without being limiting, functions of CXCL10 can include promotion of T cell adhesion to endothelial cells, antitumor activity, and inhibition of bone marrow colony formation and angiogenesis, for example. CXCL10 elicits its effects by binding to the cell surface chemokine receptor CXCR3. In a recent study, CXCL10 was shown to inhibit the proliferation and metastasis in many tumors (Jiang et al.) In some alternatives herein, a fusion protein is provided, wherein the fusion protein stimulates the production of a cytokine. In some alternatives, the cytokine is CXCL10. In some alternatives, the fusion protein comprises PD1. In some alternatives, the fusion protein comprises IFnα2a.

Co-stimulatory domain," or "intracellular signaling domain" as the term is used herein refers to a signaling moiety that provides to T-cells a signal which, in addition to the primary signal provided by for instance the CD3 zeta chain of the TCR/CD3 complex, mediates a T-cell response, including, but not limited to, activation, proliferation, differentiation, cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83. In some alternatives, a cell is manufactured, wherein the cell comprises a fusion protein for secretion and, wherein the cell further comprises a chimeric antigen receptor. In some alternatives, the chimeric antigen receptor further comprises a co-stimulatory domain. In some alternatives, the co-stimulatory domain is an intracellular signaling domain that interacts with other intracellular mediators to mediate a cell response including activation, proliferation, differentiation and cytokine secretion, and the like. In some alternatives, all or a portion of one or more domains of a molecule (here the chimeric receptor molecule) provides for activation of a lymphocyte through the co-stimulatory domain. Co-stimulatory domains of such molecules mediate a signal by interacting with cellular mediators to result in proliferation, differentiation, activation and other effector functions. In some alternatives, such molecules include all or portions of CD28, CD3, or 4-1BB, or combinations thereof.

"Cytotoxic T lymphocyte" (CTL), as used herein, refers to a T lymphocyte that expresses CD8 on the surface thereof (e.g., a CD8$^+$ T-cell). In some alternatives, such cells are preferably "memory" T-cells ($T_M$ cells) that are antigen-experienced. In some alternatives, a cell for fusion protein secretion is provided. In some alternatives, the cell is a cytotoxic T lymphocyte. "Central memory" T-cell (or "$T_{CM}$") as used herein, refers to an antigen experienced CTL that expresses CD62L, CCR-7 and/or CD45RO on the surface thereof, and does not express or has decreased expression of CD45RA, as compared to naïve cells. In some alternatives, a cell for fusion protein secretion is provided. In some alternatives, the cell is a central memory T-cell ($T_{CM}$). In some alternatives, the central memory cells are positive for expression of CD62L, CCR7, CD28, CD127, CD45RO, and/or CD95, and may have decreased expression of CD54RA, as compared to naïve cells. "Effector memory" T-cell (or "$T_{EM}$") as used herein refers to an antigen experienced T-cell that does not express or has decreased expression of CD62L on the surface thereof, as compared to central memory cells, and does not express or has a decreased expression of CD45RA, as compared to naïve cell. In some alternatives, a cell for fusion protein secretion is provided. In some alternatives, the cell is an effector memory T-cell. In some alternatives, effector memory cells are negative for expression of CD62L and/or CCR7, as compared to naïve cells or central memory cells, and may have variable expression of CD28 and/or CD45RA.

"Naïve" T-cells as used herein, refers to a non-antigen experienced T lymphocyte that expresses CD62L and/or CD45RA, and does not express CD45RO–, as compared to central or effector memory cells. In some alternatives, a cell for fusion protein secretion is provided. In some alternatives, the cell is a naïve T-cell. In some alternatives, naïve CD8+ T lymphocytes are characterized by the expression of phenotypic markers of naïve T-cells including CD62L, CCR7, CD28, CD127, and/or CD45RA.

"Effector" "$T_E$" T-cells as used herein, refers to antigen experienced cytotoxic T lymphocyte cells that do not express or have decreased expression of CD62L, CCR7, and/or CD28, and are positive for granzyme B and/or perforin, as compared to central memory or naïve T-cells. In some alternatives, a cell for fusion protein secretion is provided. In some alternatives, the cell is an effector T-cell. In some alternatives, the cell does not express or have decreased expression of CD62L, CCR7, and/or CD28, and are positive for granzyme B and/or perforin, as compared to central memory or naïve T-cells.

"Epitope" as used herein, refers to a part of an antigen or molecule that is recognized by the immune system including antibodies, T-cells, and/or B-cells. Epitopes usually have at least 7 amino acids and can be a linear or a conformational epitope. In some alternatives, a cell expressing a fusion protein is provided wherein the cell further comprises a chimeric antigen receptor. In some alternatives, the chimeric antigen receptor comprises an scFv that can recognize an epitope on a cancer cell. "Isolating," or "purifying" when used to describe the various polypeptides or nucleic acids disclosed herein, refers to a polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and can include enzymes, hormones, and other proteinaceous or non-proteinaceous solutes. In some alternatives, a method is provided wherein the method comprises delivering the nucleic acid of anyone of the alternatives described herein or the expression vector of anyone of the alternatives described herein to a bacterial cell, mammalian cell or insect cell, growing the cell up in a culture, inducing expression of the fusion protein and purifying the fusion protein for treatment.

"Ligand" as used herein refers to a substance that binds specifically to another substance to form a complex. Examples of ligands include epitopes on antigens, molecules that bind to receptors, substrates, inhibitors, hormones, and/or activators. "Ligand binding domain" as used herein refers to substance or portion of a substance that binds to a ligand. Examples of ligand binding domains include antigen binding portions of antibodies, extracellular domains of receptors, and/or active sites of enzymes. In some alternatives, a cell is provided wherein the cell comprises a fusion protein for secretion. In some alternatives, the cell further comprises a chimeric antigen receptor. In some alternatives, the chimeric antigen receptor comprises a ligand binding domain. In some alternatives, the ligand binding domain is specific for a tumor expressed protein, PDL1 or IFNAR.

Percent (%) amino acid sequence identity" with respect to the chimeric receptor polypeptide sequences identified herein is defined as the percentage of amino acid residues in a candidate sequence that are identical with the amino acid residues in the reference sequence for each of the ligand binding domain, spacer, transmembrane domain, and/or the lymphocyte activating domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program (Altschul et al., Methods in Enzymology, 266:460-480 (1996)) uses several search parameters, most of which are set to the default values. Those that are not set to default values (i.e., the adjustable parameters) are set with the following values: overlap span=1, overlap fraction=0.125, word threshold (T)=11 and scoring matrix=BLOSUM62. In some alternatives of the fusion protein, the fusion protein comprises a domain, wherein the domain comprises PD-1 or a mutated or truncated form of PD-1. In some alternatives, PD-1 or a mutated or truncated form of PD-1 comprises an amino acid sequence with 100%, 95%, 90%, 85%, or a percent sequence identity that is within a range defined by any two of the aforementioned percentages to a sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4).

"Chimeric receptor variant polynucleotide" or "chimeric receptor variant nucleic acid sequence" as used herein refers to a polypeptide-encoding nucleic acid molecule as defined below having at least 80%, 85%, 90%, or 95% nucleic acid sequence identity (or a percentage nucleic acid sequence identity within a range defined by any two of the aforementioned percentages) with the polynucleotide acid sequences provided herein, or a specifically derived fragment thereof, such as polynucleotide coding for an antigen binding domain, a polynucleotide encoding a spacer or linker domain, a polynucleotide coding for a transmembrane domain and/or a polynucleotide coding for a lymphocyte stimulatory domain. Ordinarily, a chimeric receptor variant of polynucleotide or fragment thereof will have at least 80% nucleic acid sequence identity, more preferably at least 81% nucleic acid sequence identity, more preferably at least 82% nucleic acid sequence identity, more preferably at least 83% nucleic acid sequence identity, more preferably at least 84% nucleic acid sequence identity, more preferably at least 85% nucleic acid sequence identity, more preferably at least 86% nucleic acid sequence identity, more preferably at least 87% nucleic acid sequence identity, more preferably at least 88% nucleic acid sequence identity, more preferably at least 89% nucleic acid sequence identity, more preferably at least 90% nucleic acid sequence identity, more preferably at least 91% nucleic acid sequence identity, more preferably at least 92% nucleic acid sequence identity, more preferably at least 93% nucleic acid sequence identity, more preferably at least 94% nucleic acid sequence identity, more preferably at least 95% nucleic acid sequence identity, more preferably at least 96% nucleic acid sequence identity, more preferably at least 97% nucleic acid sequence identity, more preferably at least 98% nucleic acid sequence identity and yet more preferably at least 99% nucleic acid sequence identity with the nucleic acid sequence or a derived fragment thereof. Variants do not encompass the native nucleotide sequence.

T-cells" or "T lymphocytes" as used herein can be from any mammalian, preferably primate, species, including monkeys, dogs, and humans. In some alternatives the T-cells are allogeneic (from the same species but different donor) as the recipient subject; in some alternatives the T-cells are autologous (the donor and the recipient are the same); in some alternatives the T-cells are syngeneic (the donor and the recipients are different but are identical twins).

In some alternatives, a nucleic acid encoding a fusion protein, wherein the nucleic acid comprises a first sequence, wherein the first sequence encodes a protein that modulates an immune response, a second sequence, wherein the second sequence encodes a glycine spacer and a third sequence, wherein the third sequence encodes an interferon. In some alternatives, the interferon is IFN-α, IFNα2a, IFN-β, IFN-ε, IFN-κ or IFN-ω. In some alternatives, the interferon is IFNα2a. the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA- GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the third sequence comprises a nucleic acid sequence that is 100%, 95%, 90% or 85% sequence identity to the sequence set forth in SEQ ID NO: 1 or is within a range defined by any two of the aforementioned percentages. In some alternatives, the nucleic acid further comprises a fourth sequence, wherein the fourth sequence encodes a promoter. In some alternatives, the fourth sequence comprises a nucleic acid sequence set forth in SEQ ID NO: 2. In some alternatives, the fourth sequence comprises a nucleic acid sequence that is about 100%, 95%, 90% or 85% sequence identity to the sequence set forth in SEQ ID NO: 2 or is within a range defined by any two of the aforementioned percentages. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence.

DETAILED DESCRIPTION

Provided herein are compositions comprising a secretable fusion protein for use in conjunction with chimeric antigen receptor (CAR) T-cell therapy, as well as, methods of using said compositions. Also provided are compositions comprising CAR bearing lymphocytes that can also express secretable fusion proteins. Uses of the alternatives described herein include the intrinsic production and secretion of a PD-1:IFNα2a fusion protein in CAR T-cells to support T-cell activity, promote inflammatory cytokine production and decrease immunosuppression within the solid tumor microenvironment. As such, the fusion protein and compositions provided herein improve the therapeutic efficacy of CAR therapy targeted against solid tumors by providing regulatory inputs for multiple immune cell subsets found in the tumor microenvironment. As shown in the alternatives described herein, the initial studies demonstrated that the PD-1:IFNα2a fusion proteins are efficiently secreted by T-cells and each component of the fusion protein functionally binds to specifically targeted antibodies. Furthermore, in vitro assays demonstrate that the secreted PD-1:IFNα2a protein leads to transcriptional activation of type I IFN elements in a reporter T cell line.

Alternative to the fusion of IFNα2a to PD-1, IFNα2a can also be fused to other tumor resident antigens or secretable factors known to limit and/or inhibit immunotherapeutic approaches. In the alternatives described herein, the cells provided were also tested for their ability to use T cells as a delivery vehicle for secreted, immunoregulatory proteins.

In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines.

Previously, studies that incorporated the soluble, extracellular domain of PD-1 during therapy demonstrated that soluble PD-1 blocks the PD-1 pathway and augments the antitumor immune response (Pan et al., Oneal Lett (2013)). Alternatively, IFNα treatment has been used for clinical application (Kreutzer et al., Dtsch Dermatol Ges (2004)). The fusion of both proteins and the secretion of the resultant protein by CAR T-cells have not been described.

Nucleic Acids Encoding the Fusion Protein

As described herein, a nucleic acid encoding a fusion protein is provided. The nucleic acid can have three sequences. The first sequence encodes a protein that modulates an immune response, the second sequence encodes a glycine spacer, and the third sequence encodes an interferon, wherein a 3' terminus of the first sequence is adjacent to a 5' terminus of the second sequence and a 3' terminus of the second sequence is adjacent to a 5' terminus of the third sequence. The nucleic acid can also be either DNA or RNA.

Interferons are signaling proteins that are released by host cells in a response to pathogen invasion (e.g. virus, bacteria, parasites) as well as in response to tumor cells. In the alternatives herein, the fusion protein comprises an interferon or a portion thereof, which can be used to modulate the functions of the immune system. Thus the fusion protein can be used with other therapies to control diseases such as an autoimmune disorder, cancer and leukemias for example.

In some alternatives of the fusion protein, the interferon is IFN-α, IFNα2a, IFN-β, IFN-ε, IFN-κ or IFN-ω. In some alternatives, the interferon is IFNα2a. In some alternatives, the third sequence encoding the interferon comprises a sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1).

The nucleic acid encoding a fusion protein can further comprise a fourth sequence, wherein the fourth sequence encodes a promoter. In some alternatives, the promoter is a mammalian promoter for mammalian cell protein expression or a bacterial promoter for bacterial cell protein expression. The promoter can be an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGG GAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. The promoter can thus be used to control the expression of the fusion protein, if there are off-target effects or toxicities from the fusion protein.

In some alternatives of the nucleic acid encoding the fusion protein, the nucleic acid comprises a first, second and a third sequence. The first sequence encodes a protein that modulates an immune response, the second sequence encodes an amino spacer or linker, such as a plurality of glycines or a glycine spacer, and the third sequence encodes an interferon, wherein a 3' terminus of the first sequence is adjacent to a 5' terminus of the second sequence and a 3' terminus of the second sequence is adjacent to a 5' terminus of the third sequence. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, CD19, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCAGATCCCTCAGGCCCCTTGGCCTGTCGTGTGGGC TGTGCTGCAGCTGG GATGGCGGCCTGGCTGGTTTCTGGACAGCCCCG ACAGACCCTGGAACCCCCCT ACATTTTCCCCTGCCCTGCTGGTCGTGACCGAGGGCG ACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, the PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6).

In some alternatives of the nucleic acid, the amino acid spacer or linker comprises 1, 2, 3, 4, 5, 6, 7, 8, 9 or 10 amino acids, such as glycines, or a number of amino acids, such as glycine, within a range defined by any two of the aforementioned numbers. In some alternatives, the glycine spacer comprises at least 3 glycines. In some alternatives, the glycine spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). The glycine linker can also be adjusted to improve protein folding dynamics of the fusion protein, to increase binding affinities of the fusion protein, and/or to prevent aggregation of the fusion protein.

In some alternatives, the nucleic acid further comprises a fifth sequence encoding a 2A linker, wherein the 2A linker is between the fusion protein and a protein for co-expression. In some alternatives, the fifth sequence comprises a nucleic acid sequence set forth in SEQ ID NO: 10 (GGCGGCGGAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the 2A linker is a T2A linker, a E2A linker or a P2A linker.

In some alternatives, the nucleic acid further comprises a sixth sequence encoding an IRES sequence, E2A sequence, or P2A sequence.

In some alternatives, the nucleic acid further comprises a seventh sequence encoding a marker. In some alternatives, the marker is Her2tG or EGFRt.

In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGCT-GTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13).

Vectors for Expressing the Fusion Protein

A variety of vector combinations can be constructed to provide for efficient transduction and transgene expression. The vector comprises any one of the alternative nucleic acids provided herein. In some alternatives, the vector is a viral vector. In other alternatives, the vectors can include a combination of viral vectors and plasmid vectors. Other viral vectors include foamy virus, adenoviral vectors, retroviral vectors, and lentiviral vectors. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli.

In some alternatives, a plasmid vector or a viral vector comprises the nucleic acid encoding a fusion protein. In some alternatives, the vector is RNA or DNA.

Cells and Compositions: T Lymphocyte Populations.

The compositions described herein provide for genetically modified cells with the vectors and/or constructs as described herein. In some alternatives, the cells are CD4+ and/or CD8+ T lymphocytes.

Provided herein are cells for fusion protein secretion, wherein the cell comprises the nucleic acid of anyone of the alternatives described herein or the expression vector anyone of the alternatives described herein. In some alternatives, the cell is a bacterial cell or a mammalian cell, such as a lymphocyte. In some alternatives, the cell is E. coli. In some alternatives, the cell is an insect cell capable of protein expression. In some alternatives, the cell is a lymphocyte.

In some alternatives, the cell is a CD4+ or CD8+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells.

In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells.

In some alternatives, the cell is a precursor T-cell.

In some alternatives, the cell is a stem cell.

In some alternatives, the cell is a hematopoietic stem cell or NK cell. In some alternatives, the cell is a NK cell.

In some alternatives, the cell is a B cell.

In some alternatives, the cell is a neuronal stem cell.

In some alternatives, the cell further comprises a chimeric antigen receptor.

The lymphocytes (T lymphocytes) can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some alternatives, the T cells are autologous T cells obtained from the patient.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some alternatives, the PBMC are irradiated with gamma rays in the range of 3000 to 3600 rads to prevent cell division. In some alternatives, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25 degrees Celsius, preferably at least 30 degrees, more preferably 37 degrees. In some alternatives, the temperature for the growth of human T lymphocytes is 22, 24, 26, 28, 30, 32, 34, 36, 37 degrees Celsius or any other temperature between any two endpoints of any of the listed values.

After isolation of T lymphocytes both cytotoxic and helper T lymphocytes can be sorted into naïve, memory, and effector T cell subpopulations either before or after expansion.

CD8+ cells can be obtained by using standard methods. In some alternatives, CD8+ cells are further sorted into naïve, central memory, and effector memory cells by identifying cell surface antigens that are associated with each of those types of CD8+ cells. In some alternatives, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some alternatives, the expression of phenotypic markers of central memory $T_{CM}$ include CD45RO, CD62L, CCR7, CD28, CD3, and/or CD127 and are negative or low for granzyme B. In some alternatives, central memory T cells are CD45RO+, CD62L+, and/or CD8+ T cells. In some alternatives, effector $T_E$ are negative for CD62L, CCR7, CD28, and/or CD127, and positive for granzyme B and/or perforin. In some alternatives, naïve CD8+ T lymphocytes are characterized by the expression of phenotypic markers of naïve T cells including CD62L, CCR7, CD28, CD3, CD127, and/or CD45RA.

CD4+ T helper cells are sorted into naïve, central memory, and effector cells by identifying cell populations that have cell surface antigens. CD4+ lymphocytes can be obtained by standard methods. In some alternatives, naïve CD4+ T lymphocytes are CD45RO−, CD45RA+, CD62L+, and/or CD4+ T cells. In some alternatives, central memory CD4+ cells are CD62L+ and/or CD45RO+. In some alternatives, effector CD4+ cells are CD62L− and/or CD45RO−.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% of the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells or any % between any two of the aforementioned percentages when compared to a reference cell population. In some alternatives, a cell population positive for one or markers refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % between any two of the aforementioned percentages when compared to a reference cell population.

Whether a cell or cell population is positive for a particular cell surface marker can be determined by flow cytometry using staining with a specific antibody for the surface marker and an isotype matched control antibody. A cell population negative for a marker refers to the absence of significant staining of the cell population with the specific antibody above the isotype control, positive refers to uniform staining of the cell population above the isotype control. In some alternatives, a decrease in expression of one or markers refers to loss of 1 log 10 in the mean fluorescence intensity and/or decrease of percentage of cells that exhibit the marker of at least 20% of the cells, 25% of-the cells, 30% of the cells, 35% of the cells, 40% of the cells, 45% of the cells, 50% of the cells, 55% of the cells, 60% of the cells, 65% of the cells, 70% of the cells, 75% of the cells, 80% of the cells, 85% of the cells, 90% of the cell, 95% of the cells, and 100% of the cells or any % between any two of the aforementioned percentages when compared to a reference cell population. In some alternatives, an increase refers to an increase in mean fluorescence intensity and/or to an increase in the number of cells in a cell population that are positive for one or a given marker, such as a population in which s refers to a percentage of cells that exhibit the marker of at least 50% of the cells, 55% of the cells, 60% of the cells, 65% of the cells, 70% of the cells, 75% of the cells, 80% of the cells, 85% of the cells, 90% of the cell, 95% of the cells, or 100% of the cells or any % between any two of the aforementioned percentages exhibit the marker, e.g., when compared to a reference cell population.

In some alternatives, populations of CD4+ and CD8+ that are antigen specific can be obtained by stimulating naïve or antigen specific T lymphocytes with antigen. Naïve T cells can also be used. Any number of antigens from tumor cells can be utilized as targets to modulate T cell responses. In some alternatives, the compositions comprising the cells are useful in the treatment of a disease or disorder including a solid tumor, hematologic malignancy, breast cancer or melanoma.

Method of Making a Chimeric Antigen Receptor Bearing Cell that Expresses a Fusion Protein In the alternatives described herein, it can be desired to introduce a nucleic acid or vector into a host cell such as a lymphocyte to be used in immunotherapy. The nucleic acid or vector of any one of the alternatives provided herein can be used for introduction into the host cell for immunotherapy. For example, the introduced gene or genes can improve the efficacy of therapy by enhancing the cytotoxicity in T and NK cells, promote T-cell stimulatory cytokine production in macrophages and inhibit regulatory T cell function. Furthermore, the fusion protein can also sequester the T-cell inhibitory interaction of PD-1 with the ligand PDL-1. The use of a fusion protein comprising a PD-1 and a IFNα2a component can make CAR T-cell therapy more interactive against the immunosuppressive milieu found in solid tumors by modulating stimulatory and suppressive functions to specific tumor resident immune cell subsets. Preparation of these cells can be carried out in accordance with known techniques that will be apparent to those skilled in the art based upon the present disclosure.

In some alternatives, a method of making a chimeric antigen receptor bearing cell is provided, wherein the chimeric antigen receptor bearing cell expresses a fusion protein. The method can comprise delivering to a cell, the nucleic acid of anyone of the alternatives described herein or the expression vector of the alternatives described herein and delivering to the cell, a second nucleic acid, wherein the second nucleic acid encodes a chimeric antigen receptor. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the ligand binding domain is specific for CD19. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. In some alternatives the cell is an NK cell.

Compositions

Provided herein are compositions that comprise a genetically modified cell preparation as set forth in this disclosure. In some alternatives, the cells comprise the nucleic acids encoding a fusion protein, as described in the alternatives herein. In some alternatives, the compositions comprises CD4+ T cells that have a chimeric antigen receptor comprising an extracellular antibody variable domain specific for a ligand associated with the disease or disorder, a spacer region, a transmembrane domain, and an intracellular signaling domain of a T cell receptor or other receptors. In other alternatives, the composition further comprises a chimeric receptor modified tumor-specific CD8+ cytotoxic T lymphocyte cell preparation that provides a cellular immune response, wherein the cytotoxic T lymphocyte cell preparation comprises CD8+ T cells that have a chimeric receptor comprising an extracellular single chain antibody specific for a ligand associated with the disease or disorder, a spacer region, a transmembrane domain, and an intracellular signaling domain of a T cell receptor. In some alternatives, the chimeric antigen receptor is under the control of a drug inducible promoter as described herein. In some alternatives, the chimeric receptor modified T cell population of the disclosure persist in vivo for at least 3 days or longer. In an alternative, each of these populations can be combined with one another or other cell types to provide a composition.

In some alternatives, the cells of the composition are CD4+ cells. The CD4+ cell can be T helper lymphocyte cells, naïve CD4+ T cells, central memory CD4+ T cells, effector memory CD4+ T cells, or bulk CD4+ T cells. In some alternatives, the CD4+ helper lymphocyte cell is a naïve CD4+ T cell, wherein the naïve CD4+ T cell comprises a CD45RO−, CD45RA+, and/or is a CD62L+CD4+ T cell.

In some alternatives, the cells of the composition are CD8+ cells. The CD8+ cell can be a T cytotoxic lymphocyte cell, a naïve CD8+ T cell, central memory CD8+ T cell, effector memory CD8+ T cell and/or bulk CD8+ T cell. In some alternatives, the CD8+ cytotoxic T lymphocyte cell is a central memory T cell, wherein the central memory T cell comprises a CD45RO+, CD62L+, and/or CD8+ T cell. In yet other alternatives, the CD8+ cytotoxic T lymphocyte cell is a central memory T cell and the CD4+ helper T lymphocyte cell is a naïve or central memory CD4+ T cell.

In some alternatives, the compositions comprise T cell precursors. In some alternatives, the compositions comprise hematopoietic stem cells. In some alternatives, the composition comprises a host cell wherein the host cell is a CD8+ T cytotoxic lymphocyte cell selected from the group consisting of naïve CD8+ T cells, central memory CD8+ T cells, effector memory CD8+ T cells and bulk CD8+ T cells or a CD4+ T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some alternatives, the precursor T cell is a hematopoietic stem cell.

In some compositions, the cells are NK cells.

In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor.

Fusion Proteins for Administration to a Subject

As provided herein, are fusion proteins for treatment that can be manufactured by the methods described herein. The fusion proteins can comprise a protein that can modulate an immune response, an amino acid spacer, preferably a plurality of glycines, and an interferon. In some alternatives of the fusion protein the protein domain of the interferon is from IFN-α, IFNα2a, IFN-β, IFN-ε, IFN-κ or IFN-ω. In some alternatives, the interferon is IFNα2a. In some alternatives of the fusion protein, the protein that can modulate an immune response is PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, the PD-1 is a mutated form of PD-1 and comprises an amino acid sequence set forth in SEQ ID NO: 5 (M Q I P Q A P W P V V W A V L Q L G W R P G W F L D S P D R P W NPPTFSPALLVVTEGDNATFTCSFSN
TSESFVLNWYRMSPSNQTDKLAAFPE
DRSQPGQDCRFRVTQLPNGRDFHMS
VVRARRNDSGTYLCGAISLAPKLQIK
ESLRAELRVTERRAEVPTAHPSPSPR
PAGQFQTLV; SEQ ID NO: 5). In some alternatives, the PD-1 is a mutated form of PD-1 and comprises an amino acid sequence set forth in SEQ ID NO: 6 (MQIPQAP
WPVVWAVLQLGWRPGWFLDSPDRPW
NPPTFSPALLVVTEGDNATFTCSFSN
TSESFHVVWHRESPSGQTDTLAAFPE
DRSQPGQDCRFRVTQLPNGRDFHMS
VVRARRNDSGTYVCGVISLAPKIQIK
ESLRAELRVTERRAEVPTAHPSPSPR
PAGQFQTLV; SEQ ID NO: 6). In some alternatives, the spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the glycine spacer comprises at least 3 glycines. In some alternatives, the glycine spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the fusion protein further comprises a marker. In some alternatives, the marker is Her2tG or EGFRt.

Methods for Manufacturing a Fusion Protein

As described herein are methods for manufacturing a fusion protein. The method can comprise delivering the nucleic acid of anyone of the alternatives described herein or the expression vector of anyone of the alternatives described herein to a bacterial cell, mammalian cell or insect cell, growing the cell up in a culture, inducing expression of the fusion protein and purifying the fusion protein for treatment.

In some alternatives, the inducing comprises adding IPTG, anhydrotetracycline, L-arabinose or rhamnose to the culture. In some alternatives, the cell is *E. coli*. In some alternatives, the cell is an insect-cell.

Purifying a protein from a mammalian cell, bacterial cell or insect cell is known to those skilled in the art. Without being limiting, purification can involve lysing the cell, and collecting the cell lysate. The lysate can then be subjected to precipitation protocols and differential solubilization to obtain the protein of interest. Proteins can then be separated out of the lysate by ion exchange chromatography, hydrophobic interaction chromatography and/or size exclusion chromatography. Such methods are known to those skilled in the art.

Methods of Secreting the Fusion Protein in a Subject

As described herein are methods of secreting the fusion protein in a subject in need. The method can comprise delivering to a subject the cell of anyone of the alternatives described herein or the composition of anyone of the alternatives described herein. In some alternatives, the method further comprises administering to the subject an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the subject has cancer. In some alternatives the cancer comprises adrenal cancer, bile duct cancer, bladder cancer, bone cancer, brain cancer, breast cancer, Castleman disease, cervical cancer, colon cancer, endometrial cancer, esophagus cancer, Ewing family of tumors, eye cancer, gallbladder cancer, gastrointestinal carcinoid tumors, Hodgkin disease, Kaposi Sarcoma, kidney cancer, Laryngeal and hypopharyngeal cancer, leukemia, liver cancer, lung cancer, lymphoma, multiple myeloma, malignant mesothelioma, myelodysplastic syndrome, nasopharyngeal cancer, osteosarcoma, ovarian cancer, pancreatic cancer, pituitary tumors, prostate cancer, retinoblastoma, skin cancer, small intestine cancer, stomach cancer, testicular cancer, thymus cancer, thyroid cancer or uterine sarcoma. In some alternatives, the subject is selected or identified for cancer treatment. Such selection or identification can be made by clinical or diagnostic evaluation and confirmation of the presence of a cancer.

Methods of Increasing T-Cell Activity

Described herein, are also methods of increasing T-cell activity. The method can comprise administering an effective amount of the cell of anyone of the alternatives described herein or the composition of anyone of the alternatives described herein, wherein the cells of the composition express a chimeric antigen receptor that comprises an antigen binding domain that binds to a tumor antigen expressed on a cancer cell, or the fusion protein of anyone of the alternatives described herein to a subject in need. In some alternatives, administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the subject has cancer. In some alternatives the cancer comprises adrenal cancer, bile duct cancer, bladder cancer, bone cancer, brain cancer, breast cancer, Castleman disease, cervical cancer, colon cancer, endometrial cancer, esophagus cancer, Ewing family of tumors, eye cancer, gallbladder cancer, gastrointestinal carcinoid tumors, Hodgkin disease, Kaposi Sarcoma, kidney cancer, Laryngeal and hypopharyngeal cancer, leukemia, liver cancer, lung cancer, lymphoma, multiple myeloma, malignant mesothelioma, myelodysplastic syndrome, nasopharyngeal cancer, osteosarcoma, ovarian cancer, pancreatic cancer, pituitary tumors, prostate cancer, retinoblastoma, skin cancer, small intestine cancer, stomach cancer, testicular cancer, thymus cancer, thyroid cancer or uterine sarcoma. In some alternatives, the subject is selected or identified for cancer treatment. Such selection or identification can be made by clinical or diagnostic evaluation and confirmation of the presence of a cancer.

Method of Decreasing Immunosuppression in a Tumor Microenvironment

In some alternatives, a method of decreasing immunosuppression in a tumor microenvironment is provided. The method can comprise administering an effective amount of the cell of anyone of the alternatives described herein or the composition of anyone of the alternatives described herein, wherein the cells of the composition express a chimeric antigen receptor that comprises an antigen binding domain that binds to a tumor antigen expressed on a cancer cell, or the fusion protein of anyone of the alternatives described herein to a subject in need. In some alternatives, administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the subject has cancer. In some alternatives the cancer comprises adrenal cancer, bile duct cancer, bladder cancer, bone cancer, brain cancer, breast cancer, Castleman disease, cervical cancer, colon cancer, endometrial cancer, esophagus cancer, Ewing family of tumors, eye cancer, gallbladder cancer, gastrointestinal carcinoid tumors, Hodgkin disease, Kaposi Sarcoma, kidney cancer, Laryngeal and hypopharyngeal cancer, leukemia, liver cancer, lung cancer, lymphoma, multiple myeloma, malignant mesothelioma, myelodysplastic syndrome, nasopharyngeal cancer, osteosarcoma, ovarian cancer, pancreatic cancer, pituitary tumors, prostate cancer, retinoblastoma, skin cancer, small intestine cancer, stomach cancer, testicular cancer, thymus cancer, thyroid cancer or uterine sarcoma. In some alternatives, the subject is selected or identified for cancer treatment. Such selection or identification can be made by clinical or diagnostic evaluation and confirmation of the presence of a cancer.

Methods of Treating, Inhibiting, Treating, or Ameliorating Cancer in a Subject, Such as a Human In some alternatives, a method of inhibiting, treating, or ameliorating cancer in a subject, such as a human expressing a tumor antigen is provided. The method can comprise administering an effective amount of the cell of anyone of the alternatives described herein or the composition of anyone of the alternatives described herein, wherein the cells of the composition express a chimeric antigen receptor that comprises an antigen binding domain that binds to a tumor antigen expressed on a cancer cell, or the fusion protein of anyone of the alternatives described herein to the patient. In some alternatives, administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives the cancer comprises adrenal cancer, bile duct cancer, bladder cancer, bone cancer, brain cancer, breast cancer, Castleman disease, cervical cancer, colon cancer, endometrial cancer, esophagus cancer, Ewing family of tumors, eye cancer, gallbladder cancer, gastrointestinal carcinoid tumors, Hodgkin disease, Kaposi Sarcoma, kidney cancer, Laryngeal and hypopharyngeal cancer, leukemia, liver cancer, lung cancer, lymphoma, multiple myeloma, malignant mesothelioma, myelodysplastic syndrome, nasopharyngeal cancer, osteosarcoma, ovarian cancer, pancreatic cancer, pituitary tumors, prostate cancer, retinoblastoma, skin cancer, small intestine cancer, stomach cancer, testicular cancer, thymus cancer, thyroid cancer or uterine sarcoma. In some alternatives, the cancer is breast cancer, skin cancer, lung cancer, colon cancer, prostate cancer or lymphoma. In some alternatives, the subject is selected or identified for cancer treatment. Such selection or identification can be made by clinical or diagnostic evaluation and confirmation of the presence of a cancer.

The PD-1:IFNα2a Fusion Protein

Figure 2:
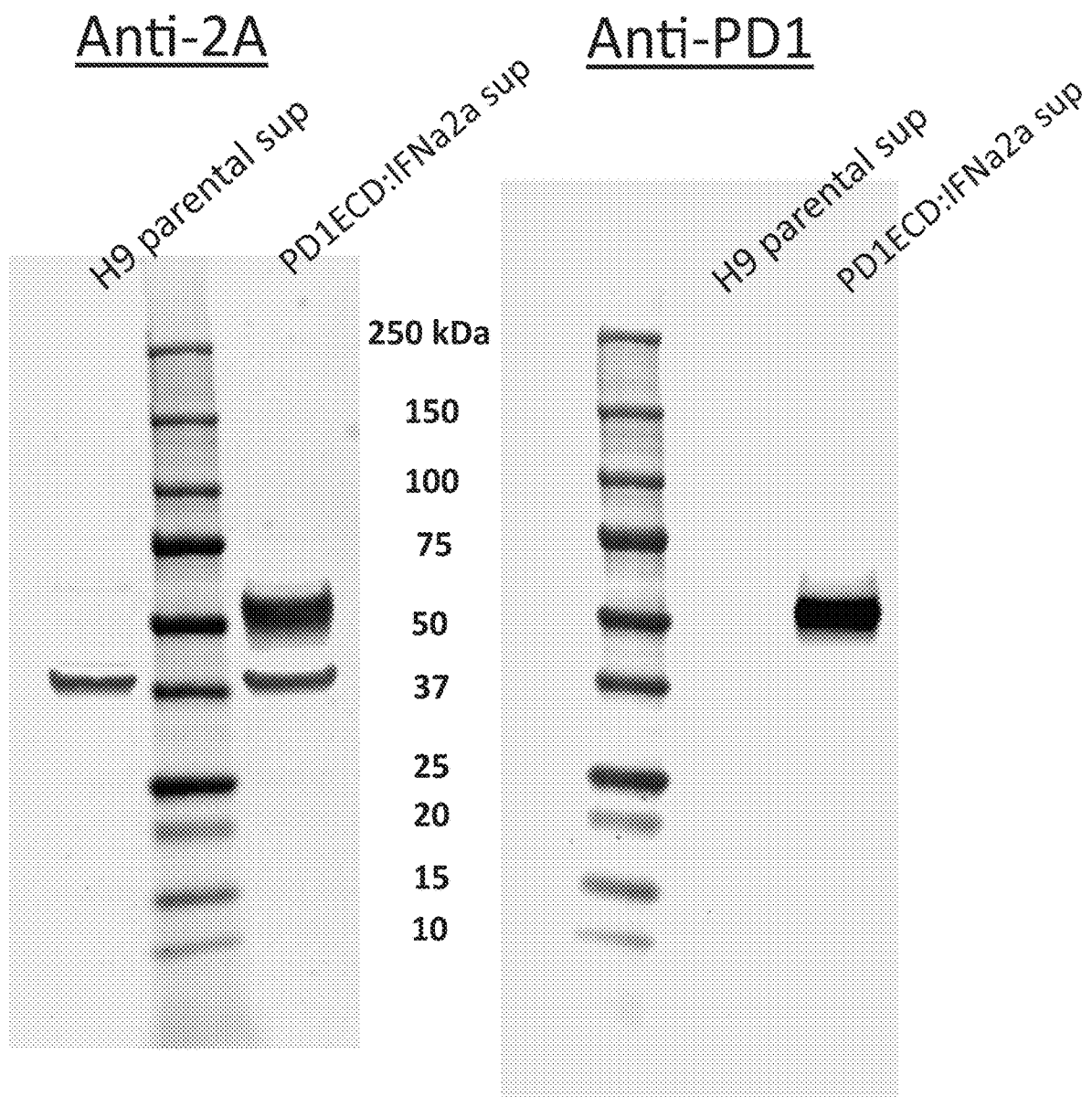
FIG. 2 shows a Western blot analysis of H9T-cell supernatant of cells transduced with a PD-1:IFNα2a-T2A-Her2tG vector and selected using Her2tG.

As described herein, the nucleic acid encoding the fusion protein comprises a EF1p sequence, a sequence for PD1ECD, a sequence encoding a G3 spacer, a sequence encoding IFNα2a, a T2A sequence, a GMCSFR signal sequence, and a sequence encoding a Her2tG marker as shown in FIG. 1. H9T cells transformed with the PD1:IFNα2a-T2AHer2tG vector and selected using Her2tG. The cell culture supernatant was concentrated and subjected to anti-2A and anti-PD1 western blot Results demonstrate that H9 T cells efficiently secrete the PD1:IFNα2a fusion and the secreted protein can be recognized by anti-PD1 antibodies (FIG. 2).

Figure 3A:
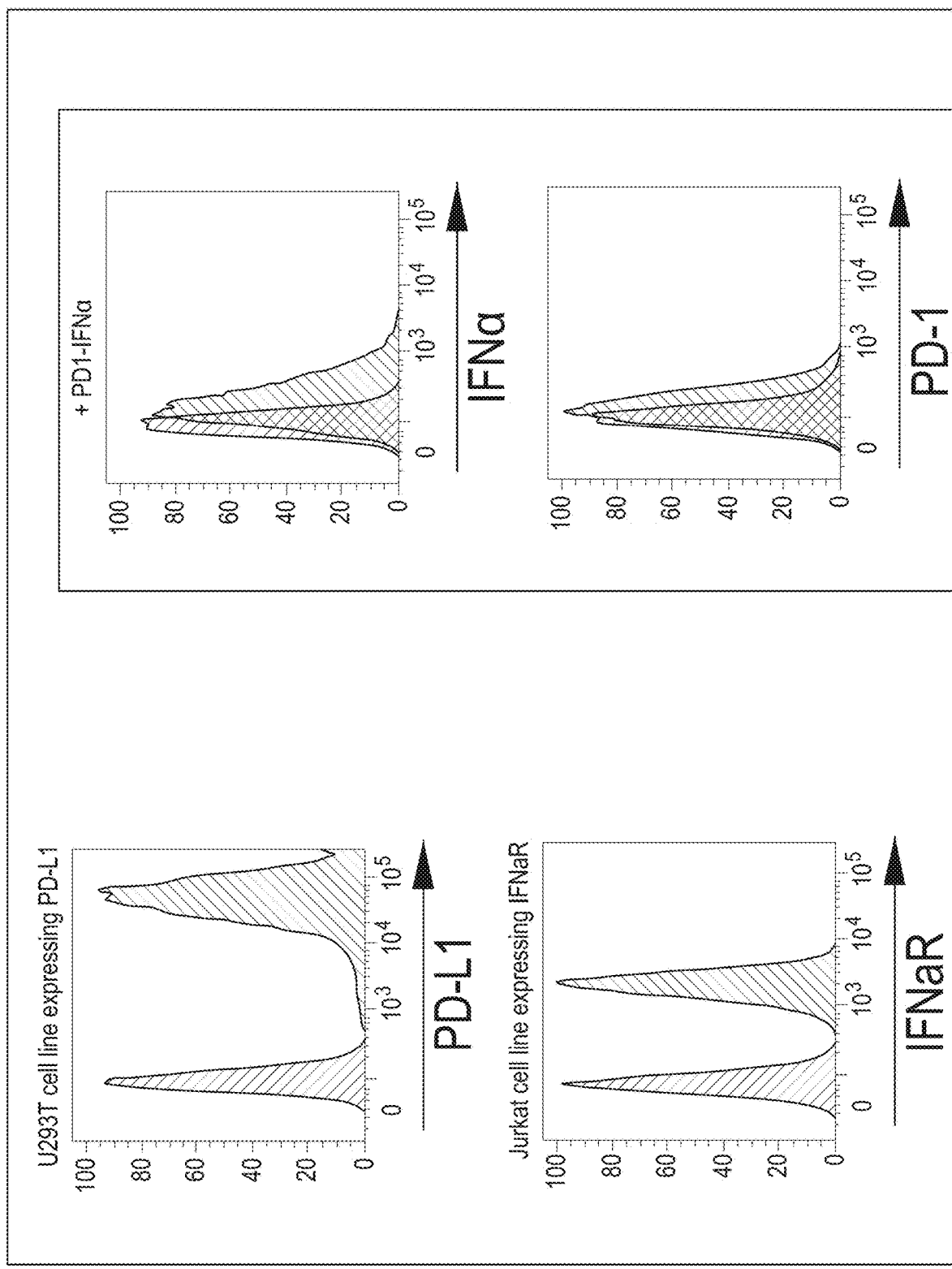
FIGS. 3A and 3B shows PD-1-IFNα2a binding to target receptors.
Figure 3B:
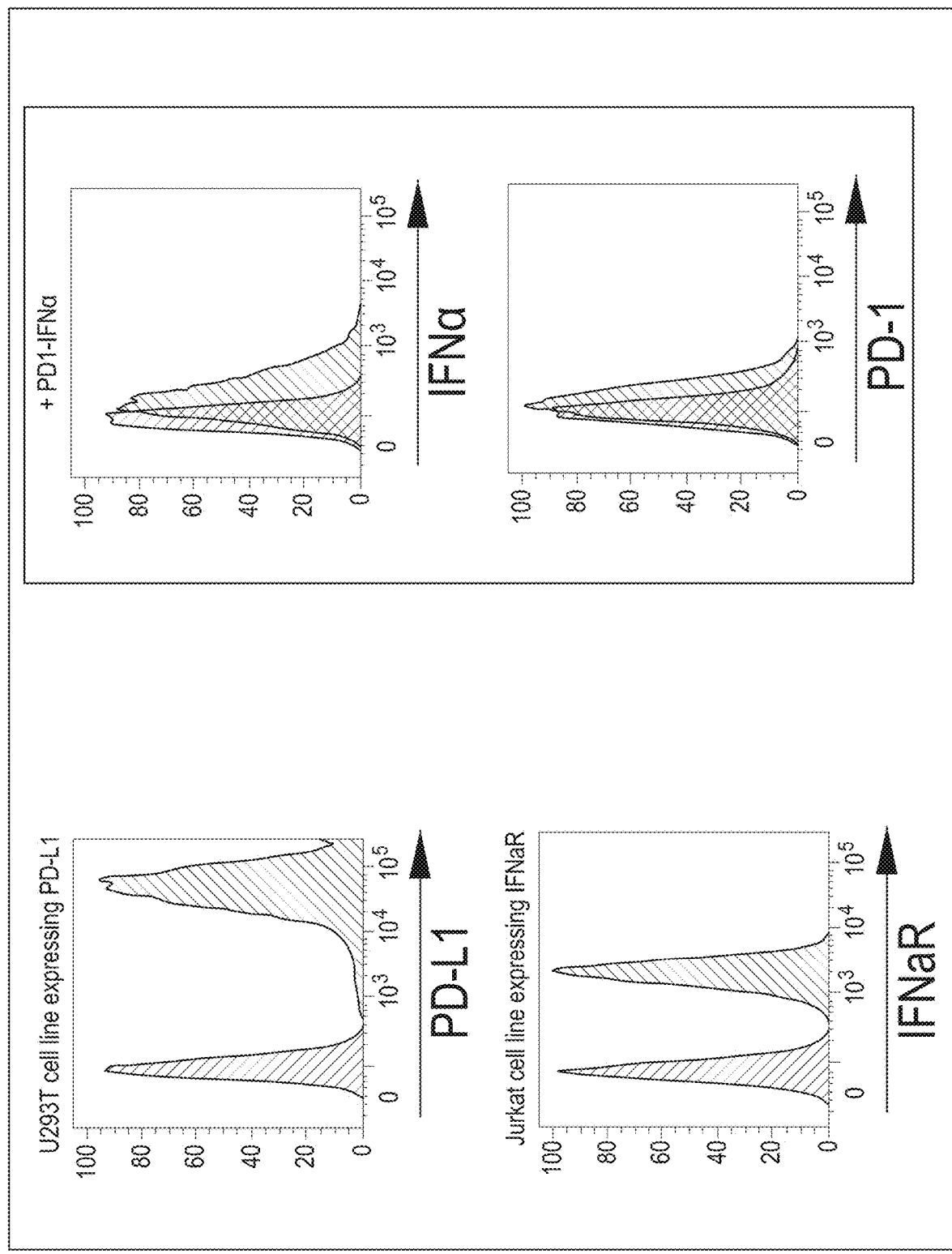

The fusion protein was then tested for binding onto target receptors. Concentrated supernatant from PD1-IFNα2a transduced H9 cells was added to target U293T cells that overexpress PD-L1, the ligand to PD1, or Jurkat cells that express IFNαR, the receptor to IFNα2a. Following incubation of supernatant with target cells, the cells were washed and then stained with an antibody specific to IFNα (U293T cells) or PD1 (Jurkat cells). U293T cells do not express IFNαR and Jurkat cells do not express PD-L1. Results demonstrate that the two components of PD1-IFNα2a can bind to its respective ligand (PD-L1 with the PD1 component) and receptor (IFNαR with the IFNα2a component) (FIGS. 3A and 3B).

In order to determine whether the fusion protein modulates immune signaling, concentrated supernatant from PD1-IFNα2a transduced H9 cells or parental H9s was added to the Jurkat reporter cell line that has a secreted embryonic alkaline phosphatase (SEAP) reporter gene under control of a interferon regulatory factor (IRF). The supernatant was incubated with the reporter cell line for 24 hr and the levels of IRF-induced SEAP was assessed from the culture supernatant using QUANTI-Blue. The schematic showing the test is shown in FIG. 5.

Figure 4:
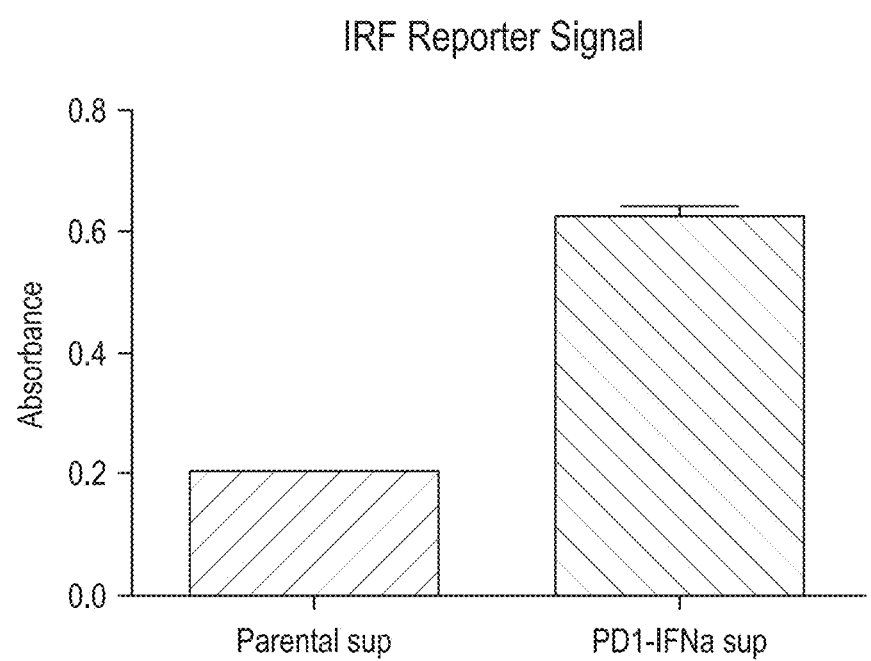
FIG. 4 shows PD-1-IFnα2a signals in a Jurkat reporter cell line.
Figure 5:
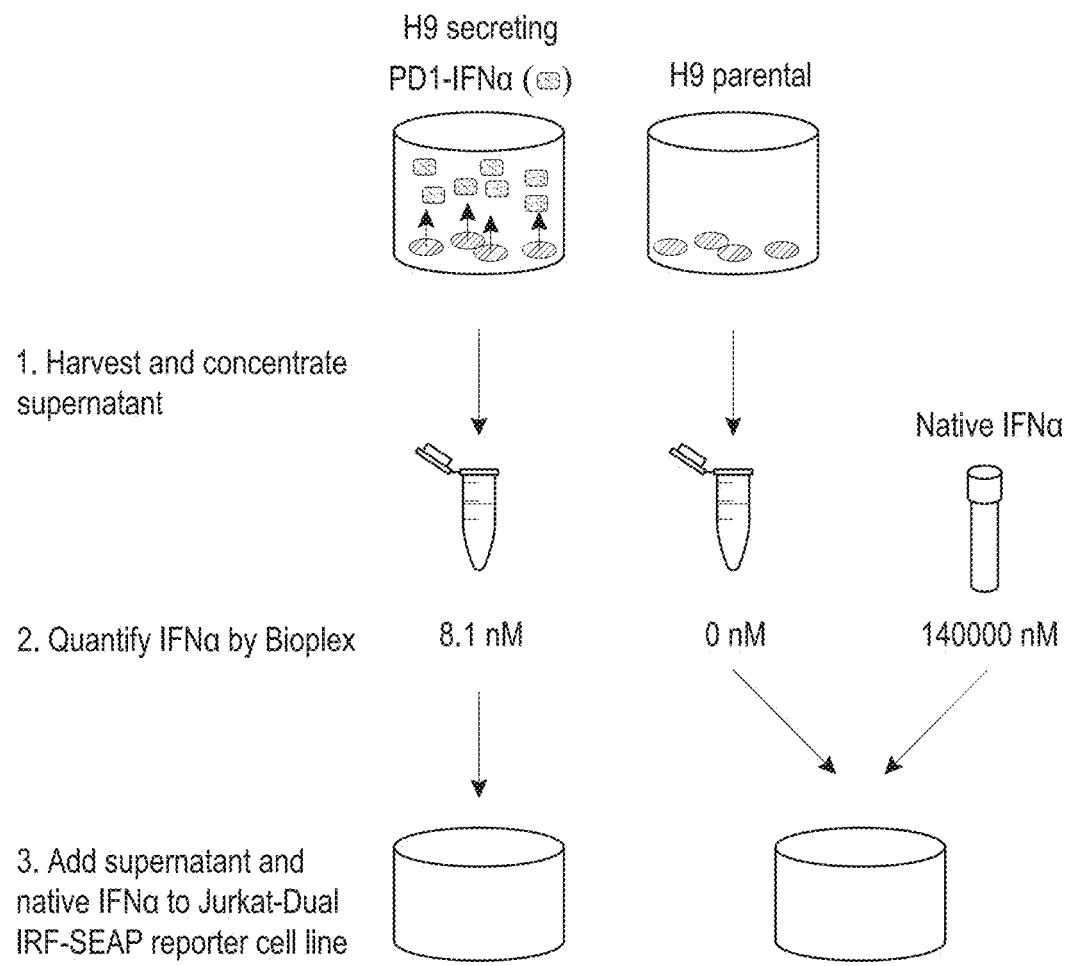
FIG. 5 shows a schematic of the assay setup to analyze potency of PD-1:IFNα2a in reference to native IFNα.

As shown in FIG. 5, an assay was set up to analyze potency of PD1:IFNα2a in reference to native IFNα. In the first step, H9 T cells were transduced with the PD1:IFNα2a and were then cultured for 24 hours and then the supernatant was harvested. Second, the harvested supernatant was concentrated using an Amicon Ultra-4 Centrifugal Filter Unit (Millipore) and subjected to an IFNα specific Bioplex Pro Inflammation Panel assay to quantify the presence of soluble PD1:IFNα2a in the supernatant (8.1 pmol/mL or 8.1 nM) in reference to an undiluted native IFNα (140000 pmol/mL or 140000 nM). As shown in the third step, based on the prior bioplex results, a known concentration range of native IFNα (0-140000 nM) and a 1:20 dilution of PD1: IFNα2a was added to an IFNα responsive Jurkat reporter cell line for 24-hr. Results demonstrate an increase in IRF-induced SEAP from PD1-IFNα2a supernatant relative to parental supernatant (FIGS. 4 and 6).

Figures 6A, 6B:
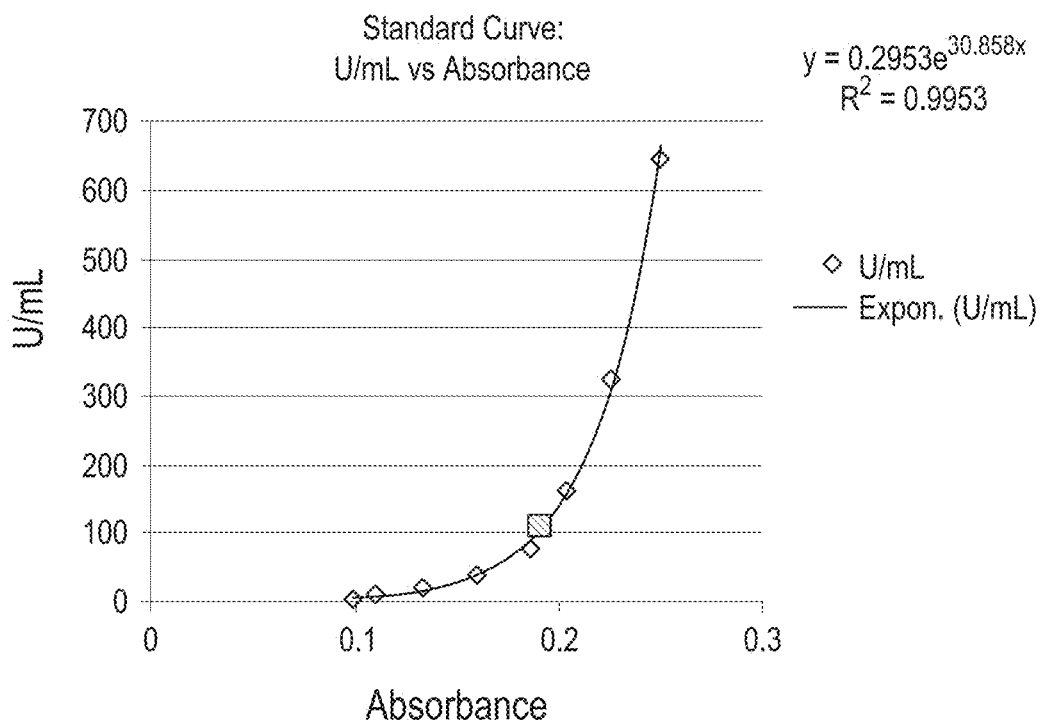
FIGS. 6A and 6B shows the analysis of the reporter cells, which are analyzed for the presence of secreted embryonic alkaline phosphatase (SEAP).

As shown in FIG. 6A, following a 24-hr incubation period, supernatant from the Jurkat reporter cells were analyzed for the presence of secreted embryonic alkaline phosphatase (SEAP) as demonstrated by absorbance (x-axis). According to the manufacturer, the native concentrated IFNα has an activity of 6.48e7U/ml and its dilutions are represented on the y-axis. In FIG. 6B, a table is shown representing relative concentrations and activity levels of native IFNα and the PD1:IFNα2a supernatant. The PD1: IFNα2a supernatant was diluted 1:20 in assay, resulting in an activity of 96.1 U/ml as represented by the large green square in FIG. 6 A (at 100 U/mL). Accounting for the 1:20 dilution, the stock PD1:IFNα2a has an activity of 1921 U/ml. The U/ml was divided by pmol/ml to calculate the U/pmol of both the native IFNα and the PD1:IFNα2a containing supernatant. Results demonstrate that the PD1: IFNα2a is around 50% as potent as native IFNα for inducing SEAP activity in the Jurkat reporter cell line.

Activity of the PD-1-IFNα2a Protein

While it is known that PD-1-IFNα2a is recognized by PD-1 and IFNα2a specific antibodies (flow cytometric and bead array analysis), studies to demonstrate complete activity relative to its individual counterparts can be tested. In some alternatives, if reduced activity is demonstrated, variable glycine-based spacer lengths between PD-1 and IFNα2a can be introduced to better facilitate proper protein folding and protein activity. Furthermore, the systemic administration of IFNα2a can cause adverse effects in normal tissue. If the PD-1:IFNα2a also causes off-target toxicities expression can be regulated by control under a drug regulatable promoter or by CAR-dependent signaling (e.g. tamoxifen or NFAT regulated promoter systems).

Examining the Effects of PD1:IFNα2a on Primed or Stimulated Monocytes

Figure 14:
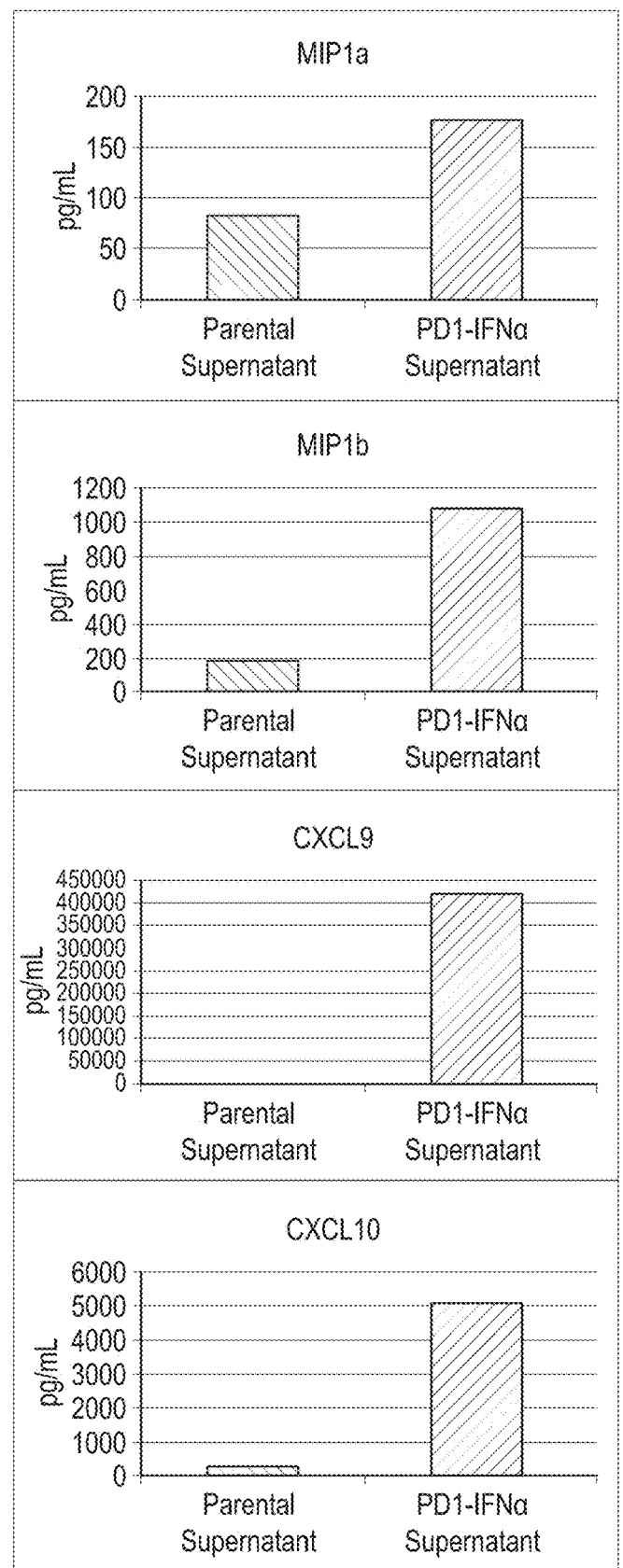
FIG. 14 shows that the fusion protein, PD1:IFNα2a, can stimulate the regulatory signaling molecules that are produced by macrophages.

PD1:IFnα2a containing H9 supernatant stimulates regulatory signaling molecules produced by macrophages, as shown in FIG. 14. Macrophages were M1-differentiated via treatment with IFNy and LPS. The M1-differentiated cells were then cultured for 24 hrs in the presence of varying concentrations of PD1:IFnα2a supernatant. Following the 24 hr culture, the supernatant was harvested and subjected to a luminex bead-based assay for multiple macrophage specific secretory proteins. Macrophage inflammatory proteins (MIPs) stimulate pro-inflammatory cytokine release from fibroblasts and other macrophages. Chemokine (CXC motif) ligands 9 and 10 are chemo-attractants of T-cells, NK cells, macrophages and dendritic cells. CXCL10 has been show to prevent angiogenesis and promote the generation of tumor-specific T-cells.

Examining the Effects of PD1:IFNα2a on Primed or Stimulated Monocytes

Secreted fusion proteins offer an attractive means of engineering cellular interplay with the advantage of reaching a diverse cell population. Type I IFN drives anti-tumor activity in virtually all immune cell subsets, including increased cytotoxicity in T and NK cells and increased inflammatory cytokine production in macrophages. To examine the cytokine response of macrophages to the PD1: IFNα2a fusion protein an assay is developed to culture primed (GMCSF cultured) or classically activated/stimulated (GMCSF, LPS and IFNy cultured) monocytes, driven towards an M1-polarized macrophage phenotype, in the presence or absence of PD1:IFNα2a. Following a 24-hr culture period, supernatant will be harvested and analyzed by Bioplex assay. Included in this assay is an antibody panel able to specifically identify and quantify levels of inflammatory cytokine (such as IL12, TNFα, IL4, etc.) located in the supernatant. Results will inform the role PD1:IFNα2a plays on the cytokine profile produced by M1-polarized macrophages and advise how these macrophages may positively affect other immune cell subsets such as T and NK cells.

CD4 and CD8 T-Cells can Co-Express a CAR and PD1: IFNα.

Figure 7B:
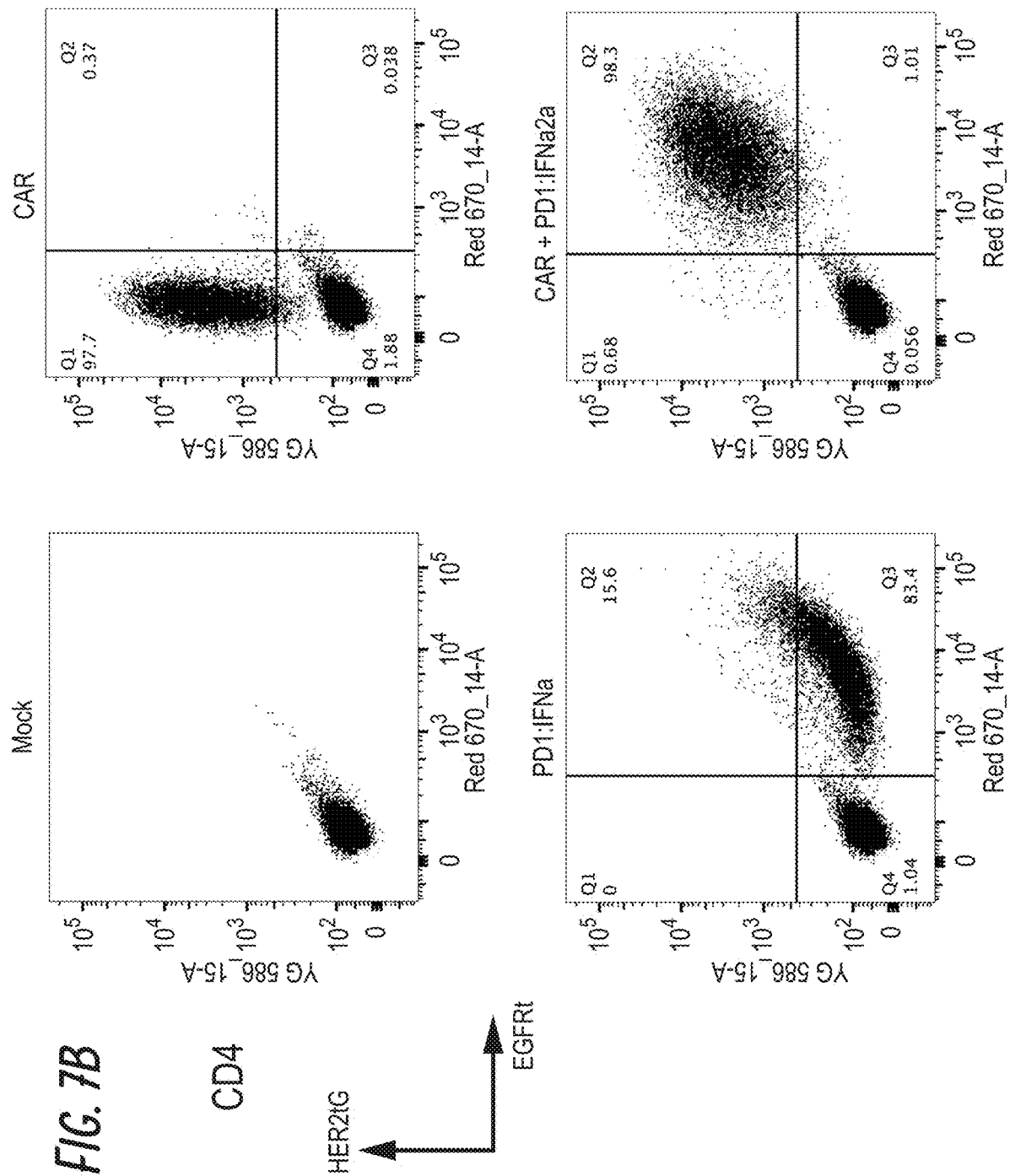

In order to test whether primary CD4 and CD8 T-cells can co-express a CAR and PD1:IFNα, Primary CD4 and CD8 T-cells were isolated from PBMCs using CD4 or CD8 microbeads, respectively. The CD4 and CD8 T-cells were selected up to 99% and 92.3% purity, respectively (FIG. 7A). The purified CD4 or CD8 T-cells were then stimulated with CD3/CD28 microbeads for three days and then transduced with lentivirus containing the following: CD19scFv-IgG4hinge-CD28tm/41BB-zeta-T2A-Her2tG ($2^{nd}$ generation short spacer CD19CAR) and/or EGFRt-T2A-PD1: IFNα2a. The transduced CD4 and CD8 T-cells were then expanded (10-12 days) and subjected to purification using biotinylated Herceptin or Erbitux to select for Her2tG or EGFRt positive populations, respectively. The dual transduced CD4 or CD8 T-cells were subjected to a second round of purification 4 days later for the second selection marker (Her2tG first selection, EGFRt second selection). Results as shown in FIG. 7B demonstrated that the dual transduced T-cells were >95% dual positive following the selection methods.

The EGFRt-T2A-PD1:IFNα2a fusion protein was encoded by the nucleic acid sequence set forth in SEQ ID NO: 14 (ATGCTT CTCCTGGTGA CAAGCCTTCT GCTCTGTGAG TTACCACACC CAGCATTCCT CCTGATCCCA CGCAAAGTGT GTAACGGAAT AGGTATTGGT GAATTTAAAG ACTCACTCTC CATAAATGCT ACGAATATTA AACACTTCAA AAACTGCACC TCCATCAGTG GCGATCTCCA CATCCTGCCG GTGGCATTTA GGGGTGACTC CTTCACACAT ACTCCTCCTC TGGATCCACA GGAACTGGAT ATTCTGAAAA CCGTAAAGGA AATCACAGGG TTTTTGCTGA TTCAGGCTTG GCCTGAAAAC AGGACGGACC TCCATGCCTT TGAGAACCTA GAAATCATAC GCGGCAGGAC CAAGCAACAT GGTCAGTTTT CTCTTGCAGT CGTCAGCCTG AACATAACAT CCTTGGGATT ACGCTCCCTC AAGGAGATAA GTGATGGAGA TGTGATAATT CAGGAAACA AAAATTTGTG CTATGCAAAT ACAATAAACT GGAAAAAACT GTTTGGGACC TCCGGTCAGA AAACCAAAAT TATAAGCAAC AGAGGTGAAA ACAGCTGCAA GGCCACAGGC CAGGTCTGCC ATGCCTTGTG CTCCCCCGAG GGCTGCTGGG GCCCGGAGCC CAGGGACTGC GTCTCTTGCC GGAATGTCAG CCGAGGCAGG GAATGCGTGG ACAAGTGCAA CCTTCTGGAG GGTGAGCCAA GGGAGTTTGT GGAGAACTCT GAGTGCATAC AGTGCCACCC AGAGTGCCTG CCTCAGGCCA TGAACATCAC CTGCACAGGA CGGGGACCAG ACAACTGTAT CCAGTGTGCC CACTACATTG ACGGCCCCCA CTGCGTCAAG ACCTGCCCGG CAGGAGTCAT GGGAGAAAAC AACACCCTGG TCTGGAAGTA CGCAGACGCC GGCCATGTGT GCCACCTGTG CCATCCAAAC TGCACCTACG GATGCACTGG GCCAGGTCTT GAAGGCTGTC CAACGAATGG GCCTAAGATC CCGTCCATCG CCACTGGGAT GGTGGGGGCC CTCCTCTTGC TGCTGGTGGT GGCCCTGGGG ATCGGCCTCT TCATGGGCGG CGGAGAGGGC AGAGGAAGTC TTCTAACATG CGGTGACGTG GAGGAGAATC CCGGCCCTAG GATGCAGATC CCTCAGGCCC CTTGGCCTGT CGTGTGGGCT GTGCTGCAGC TGGGATGGCG GCCTGGCTGG TTTCTGGACA GCCCCGACAG ACCCTGGAAC CCCCCTACAT TTTCCCCTGC CCTGCTGGTC GTGACCGAGG GCGACAATGC CACCTTCACC TGTAGCTTCA GCAACACCAG CGAGAGCTTC GTGCTGAACT
GGTACAGAAT GAGCCCCAGC AACCAGACCG
ACAAGCTGGC CGCCTTCCCC GAGGATAGAT
CTCAGCCCGG CCAGGACTGC CGGTTCAGAG
TGACCCAGCT GCCCAACGGC CGGGACTTCC
ACATGTCTGT CGTGCGGGCC AGACGGAACG
ACAGCGGCAC ATATCTGTGC GGCGCCATCA
GCCTGGCCCC CAAGCTCCAG ATCAAAGAGA GCCT-
GAGAGC CGAGCTGAGA GTGACCGAGA
GAAGGGCCGA AGTGCCTACC GCCCACCCTA GCC-
CATCTCC AAGACCTGCC GGCCAGTTCC
AGACACTCGT GGGCGGAGGA TGCGACCTGC
CTCAGACACA CAGCCTGGGC AGCAGACGGA
CCCTGATGCT GCTGGCCCAG ATGCGAAGA
TCAGCCTGTT CAGCTGCCTG AAGGACCGGC
ACGACTTCGG CTTCCCTCAG GAAGAGTTCG
GCAACCAGTT TCAGAAGGCC GAGACAATCC
CCGTGCTGCA CGAGATGATC CAGCAGATCT
TCAACCTGTT CTCCACCAAG GACAGCAGCG
CCGCCTGGGA CGAGACACTG CTGGACAAGT
TCTACACCGA GCTGTACCAG CAGCTGAATG
ACCTGGAAGC CTGCGTGATC CAGGGCGTGG
GCGTGACAGA GACACCCTG ATGAAGGAAG
ATAGCATCCT GGCCGTGCGC AAGTACTTCC AGCG-
GATCAC CCTGTACCTG AAAGAGAAGA AGTA-
CAGCCC CTGCGCCTGG GAGGTCGTGC
GCGCCGAGAT CATGAGAAGC TTCAGCCTGA
GCACCAACCT GCAGGAAAGC CTGCGGAGCA
AAGAATAA; SEQ ID NO: 14). EGFRt-T2A-PD1:IFNα2a fusion protein comprises an amino acid sequence as set forth in SEQ ID NO:15 (M L L L V T S L L L C E L P H P A F L L I P R K V C N G I G I G E F K D S L S I N A T N I K H F K N C T S I S G D L H I L P V A F R G D S F T H T P P L D P Q E L D I L K T V K E I T G F L L I Q A W P E N R T D L H A F E N L E I I R G R T K Q H G Q F S L A V V S L N I T S L G L R S L K E I S D G D V I I S G N K N L C Y A N T I N W K K L F G T S G Q K T K I I S N R G E N S C K A T G Q V C H A L C S P E G C W G P E P R D C V S C R N V S R G R E C V D K C N L L E G E P R E F V E N S E C I Q C H P E C L P Q A M N I T C T G R G P D N C I Q C A H Y I D G P H C V K T C P A G V M G E N N T L V W K Y A D A G H V C H L C H P N C T Y G C T G P G L E G C P T N G P K I P S I A T G M V G A L L L L L V V A L G I G L F M G G G E G R G S L L T C G D V E E N P G P R M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E P T A H P S P S P R P A G Q F Q T L V G G G C D L P Q T H S L G S R R T L M L L A Q M R K I S L F S C L K D R H D F G F P Q E E F G N Q F Q K A E T I P V L H E M I Q Q I F N L F S T K D S S A A W D E T L L D K F Y T E L Y Q Q L N D L E A C V I Q G V G V T E T P L M K E D S I L A V R K Y F Q R I T L Y L K E K K Y S P C A W E V V R A E I M R S F S L S T N L Q E S L R S K E; SEQ ID NO:15)

Figure 7B:
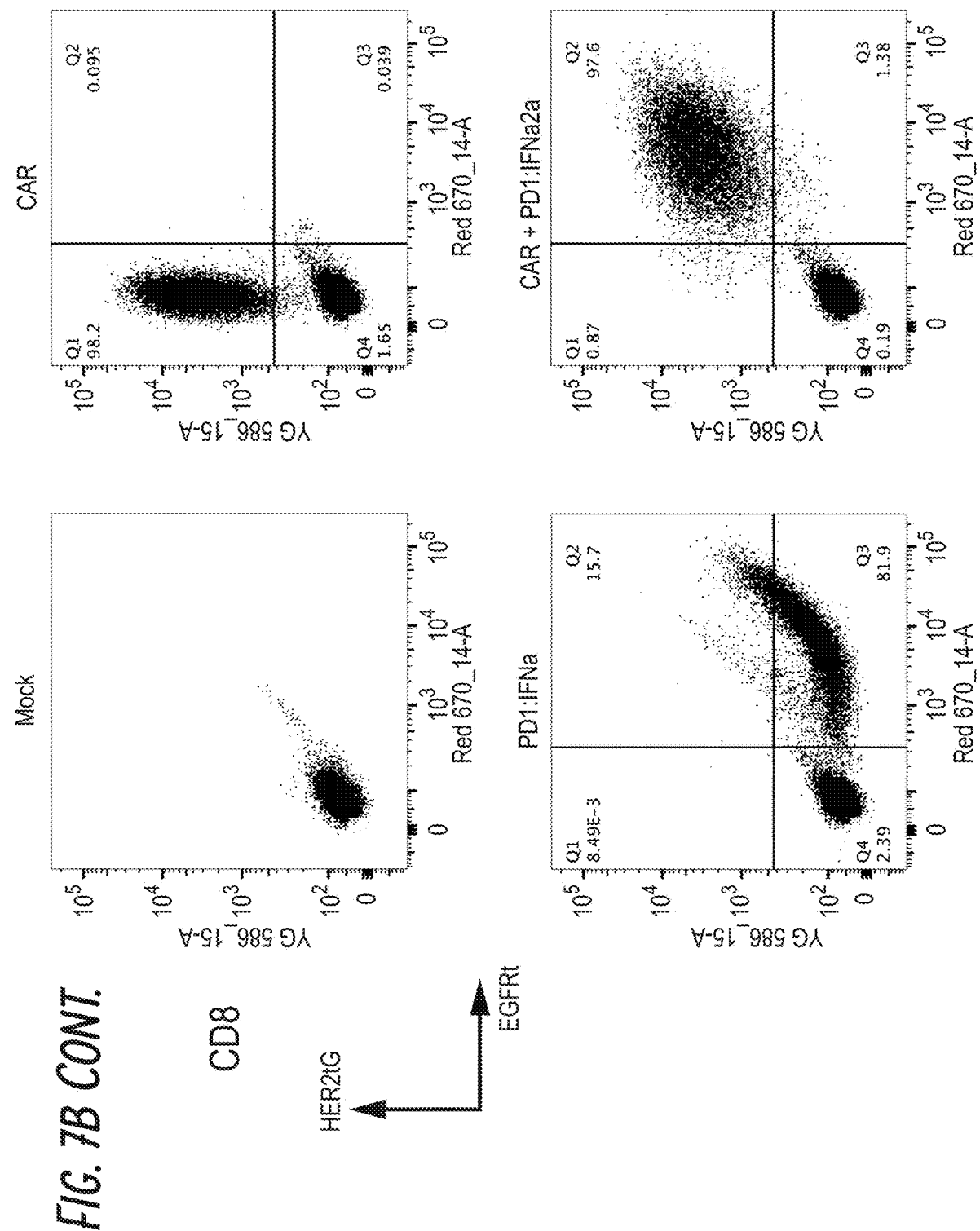
Figure 8:
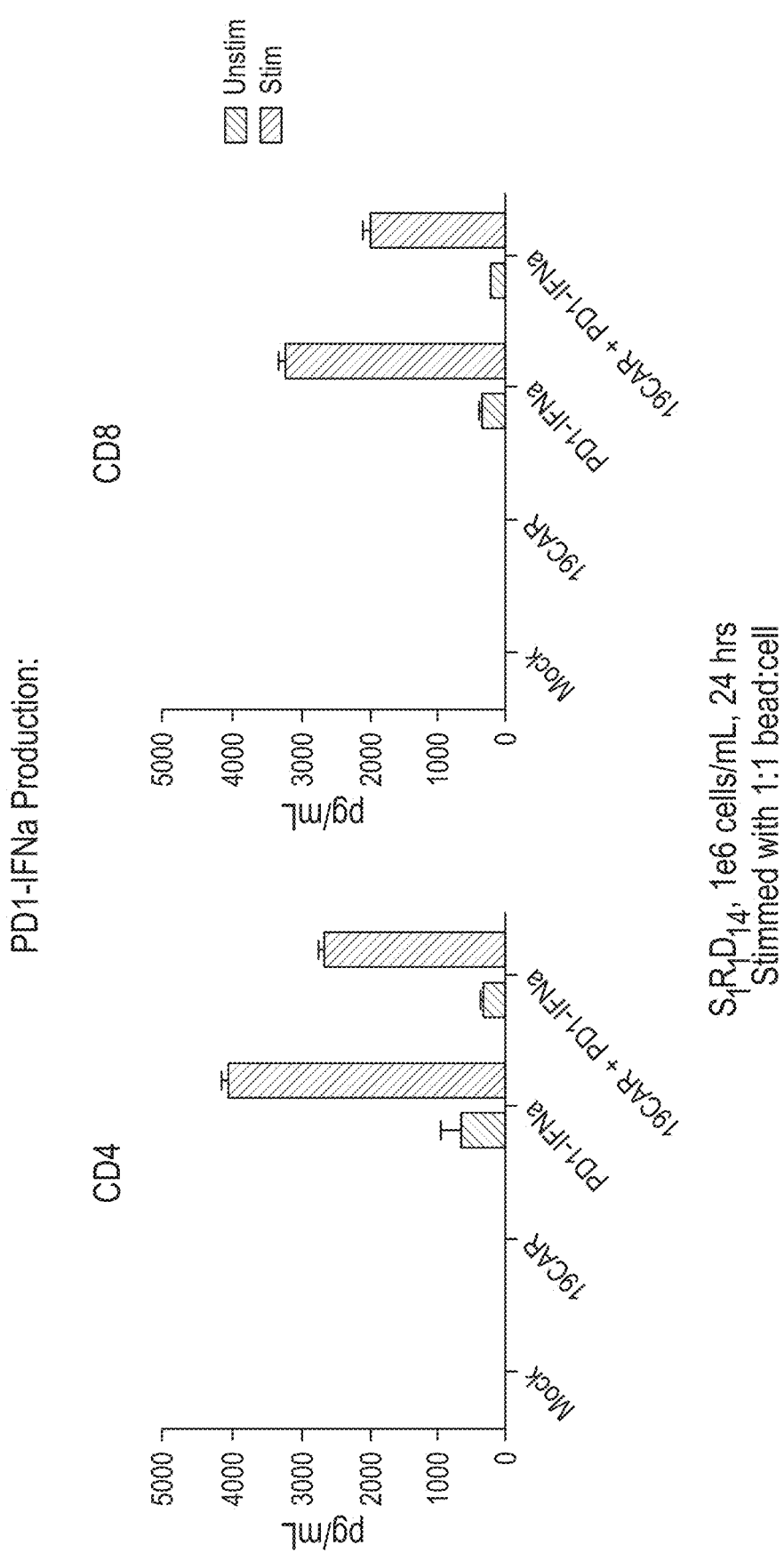
FIG. 8 demonstrates that primary T-cells produce PD1:IFNα2a. Selected T-cell populations from FIGS. 7A and 7B were subjected to either a standard rapid expansion protocol (REP) (REP-Mock or PD1:IFNα2a alone expressing) or a Seitaro REP (CD19CAR or dual CD19CAR and PD1:IFNα2a expressing). On the $14^{th}$ day of the REP, CD4 or CD8 T-cells were stimulated for 24 hours at a 1:1 ratio CD3/CD28 bead:T-cell. Following the 24 hour incubation period, supernatant was collected and then subjected to an IFNα2a specific Bioplex assay. Results demonstrate basal PD1:IFNα2a levels under normal conditions, but elevated PD1:IFNα2a levels are seen upon stimulation.

The CD4 and CD8 cells were then examined to determine whether the primary T-cells can produce the PD1: IFNα2a. The selected T-cell populations from FIG. 7 were subjected to either a standard rapid expansion protocol (REP) (REP-Mock or PD1:IFNα2a alone expressing) or a Seitaro REP (CD19CAR or dual CD19CAR and PD1:IFNα2a expressing). On the 14$^{th}$ day of REP, CD4 or CD8 T-cells were stimulated for 24 hours at a 1:1 ratio CD3/CD28 bead:T-cell. Following the 24 hour incubation period, the supernatant was collected and then subjected to an IFNα2a specific Bioplex assay. Results demonstrate basal PD1:IFNα2a levels under normal conditions, but elevated PD1:IFNα2a levels were seen upon stimulation (FIG. 8).

Figure 9:
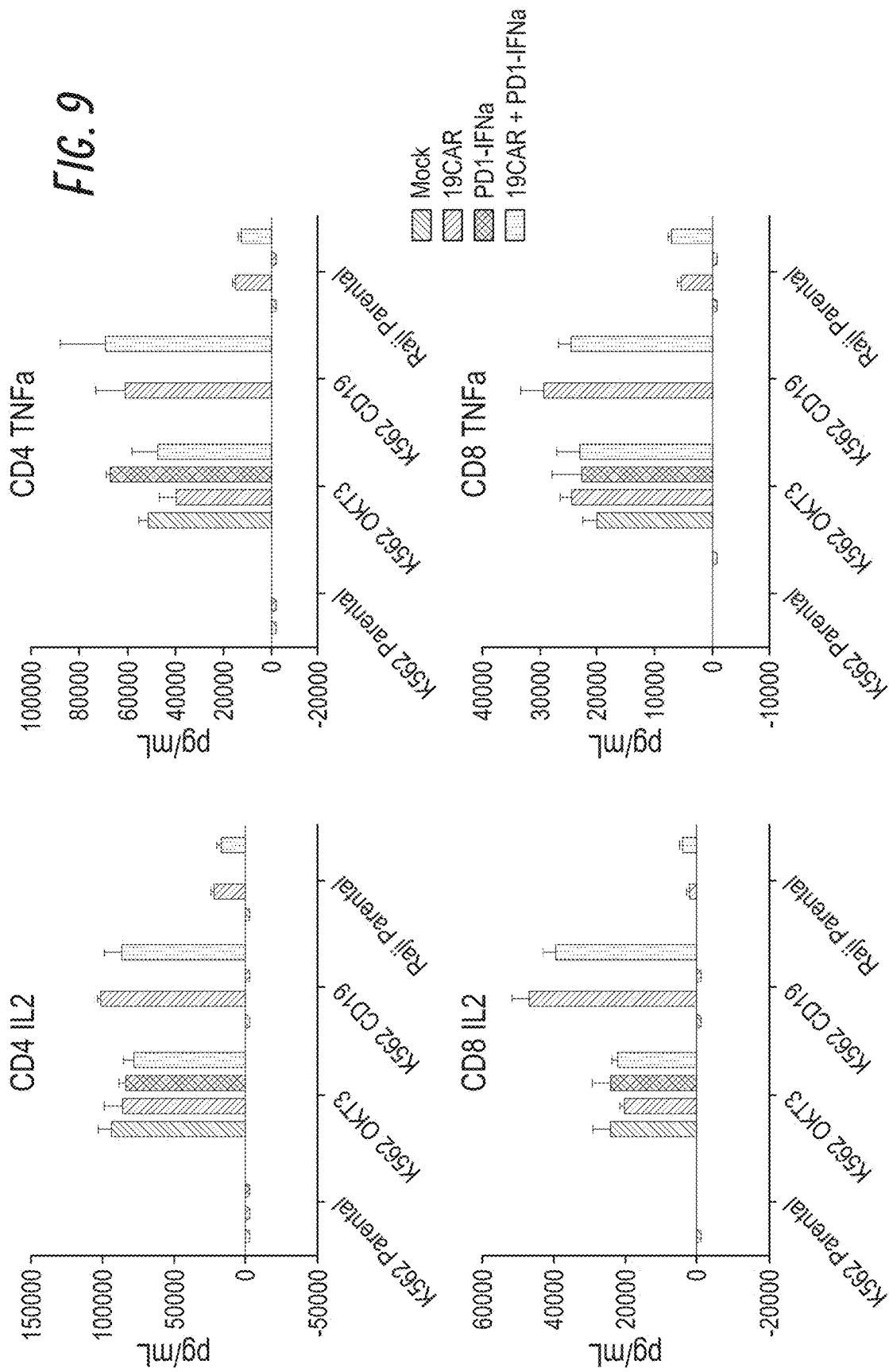
FIG. 9 shows that the expression and secretion of PD1:IFNα2a does not interfere with effector cytokine production. Selected T-cell populations from FIGS. 7A and 7B were subjected to either a standard rapid expansion protocol (REP) (REP-Mock or PD1:IFNα2a alone expressing) or a Seitaro REP (CD19CAR or dual CD19CAR and PD1:IFNα2a expressing). On the $14^{th}$ day of the REP, CD4 or CD8 T-cells were co-cultured with target cells at a 2:1 effector:target ratio. Following the 24 hour incubation period, supernatant was collected and then subjected to a Bioplex assay for IL2 and TNFα production. K562 parental and the negative control, had no active T-cell target so there is no cytokine production. K562 OKT3 and the positive control, demonstrated that all T-cells were able to produce similar levels of effector cytokine upon stimulation. K562 CD19 and Raji parental co-culture only induced T-cell cytokine production if the T-cells expressed the CD19CAR. The production of the PD1:IFNα2a did not interfere with IL2 and TNFα effector cytokine production.

The expression and secretion of PD1:IFNα2a was then evaluated to determine if the expression and secretion of PD1:IFNα2a would interfere with effector cytokine production. Selected T-cell populations from FIG. 7 were subjected to either a standard rapid expansion protocol (REP) (REP-Mock or PD1:IFNα2a alone expressing) or a Seitaro REP (CD19CAR or dual CD19CAR and PD1:IFNα2a expressing). On the 14$^{th}$ day of REP, CD4 or CD8 T-cells were co-cultured with target cells at a 2:1 effector:target ratio. Following the 24 hour incubation period, supernatant was collected and then subjected to a Bioplex assay for IL2 and TNFα production. The K562 parental and negative control had no active T-cell target so there is no cytokine production. The K562 OKT3, positive control, demonstrates that all T-cells were able to produce similar levels of effector cytokine upon stimulation. K562 CD19 and Raji parental co-culture only induced T-cell cytokine production if the T-cells expressed the CD19CAR. The production of the PD1:IFNα2a did not interfere with IL2 and TNFα effector cytokine production as shown in FIG. 9.

Figure 10:
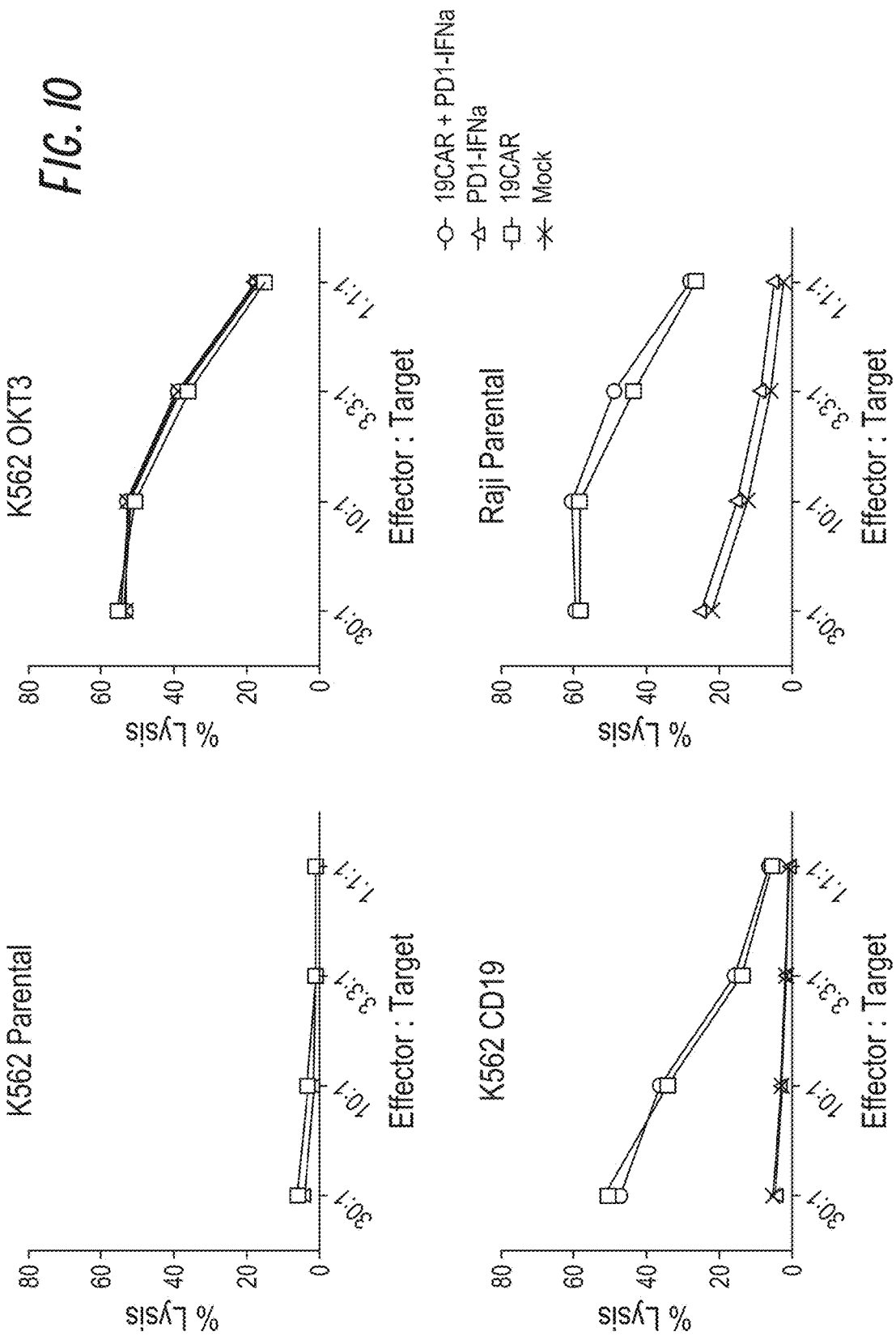
FIG. 10 shows that the expression and secretion of PD1:IFNα2a does not interfere with effector phenotype or target specificity. As shown is the in vitro cytotoxicity of CD8$^+$ T-cells by chromium release. The 4 hr chromium release assay showed CD19-CAR T-cell specificity against CD19+ (K562 CD19 and Raji parental) and control target cells (negative control=K562 parental; positive control=K562 OKT3). CD8+ T-cells were co-cultured with target cells at a 30:1, 10:1, 3.3:1 or 1.1:1 ratio.

The expression and secretion of PD1:IFNα2a was also examined to determine if expression and secretion of PD1:IFNα2a interferes with effector phenotype or target specificity. An in vitro cytotoxicity of CD8$^+$ T-cells by chromium release was performed. A 4 hour chromium release assay was performed that showed CD19-CAR T− cell specificity against CD19$^+$ (K562 CD19 and Raji parental) and control target cells (negative control=K562 parental; positive control=K562 OKT3). CD8$^+$ T-cells were co-cultured with target cells at a 30:1, 10:1, 3.3:1 or 1.1:1 ratio. As shown, in FIG. 10, the expression and secretion of PD1:IFNα2a does not interfere with effector phenotype or target specificity.

Figure 11:
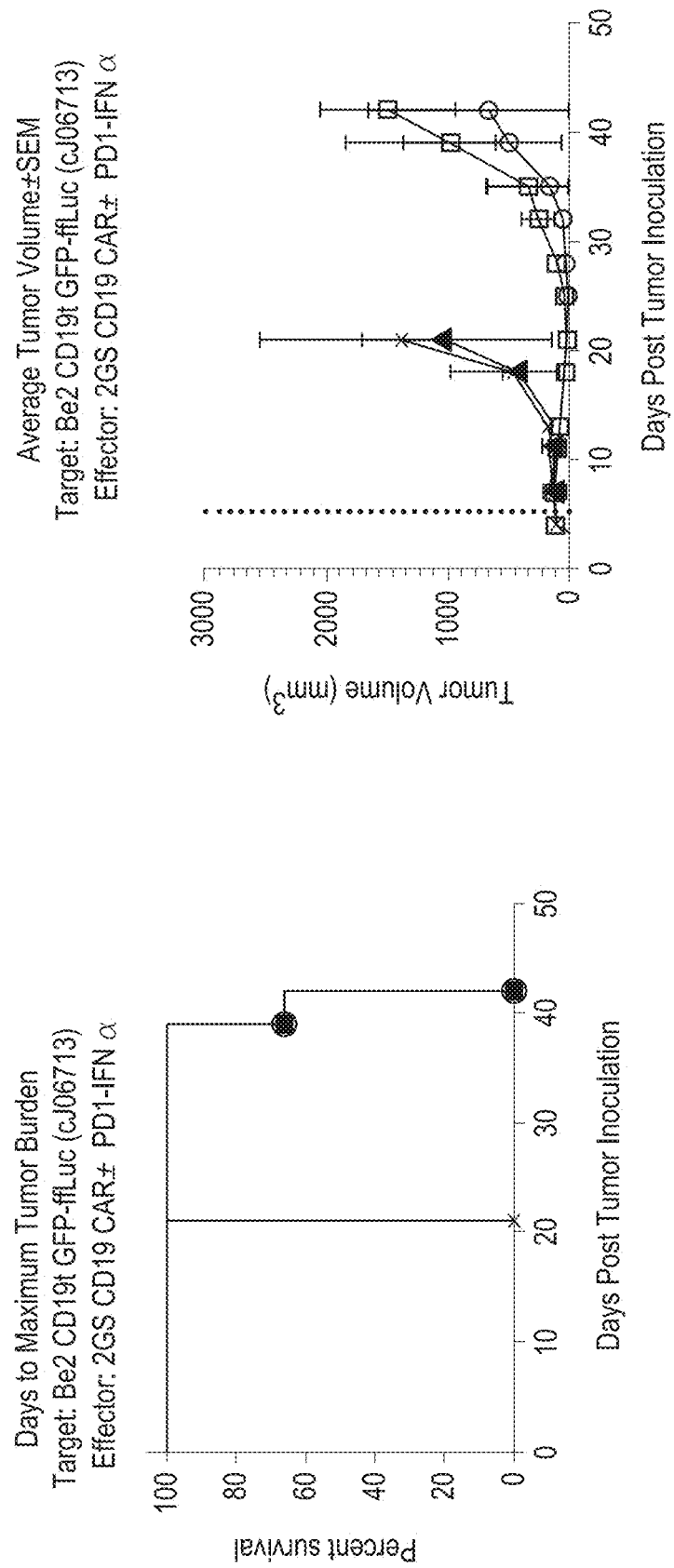
FIG. 11 shows the in vivo antitumor activity of CD19CAR– or CD19CAR and PD1-IFNα2a expressing T-cells. 5e$^6$ Be2 CD19t eGFP:ffluc neuroblastoma cells were subcutaneously injected into the left and right flanks of NOD-SCID IL-2Ry null mice. Five days later 30e$^6$ T-cells at a 1:1 CD4:CD8 ratio were injected intravenously (i.v.). Subsequent tumor volume measurements by caliper were performed as was imaging using D-luciferin and the IVIS imaging system. CD19CAR and PD1-IFNα2a expressing T-cells were able to inhibit tumor growth at a similar rate to CD19CAR-alone expressing T-cells.
Figure 11:
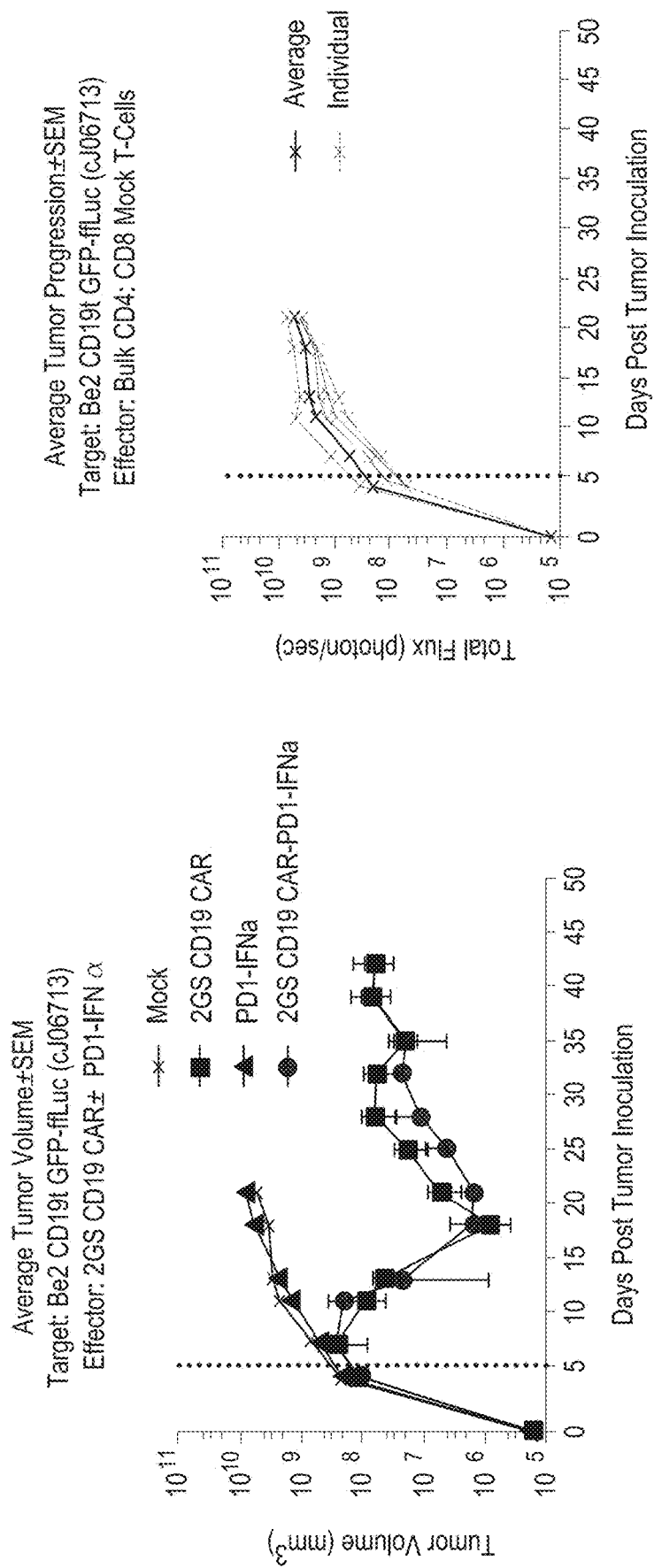
Figure 11:
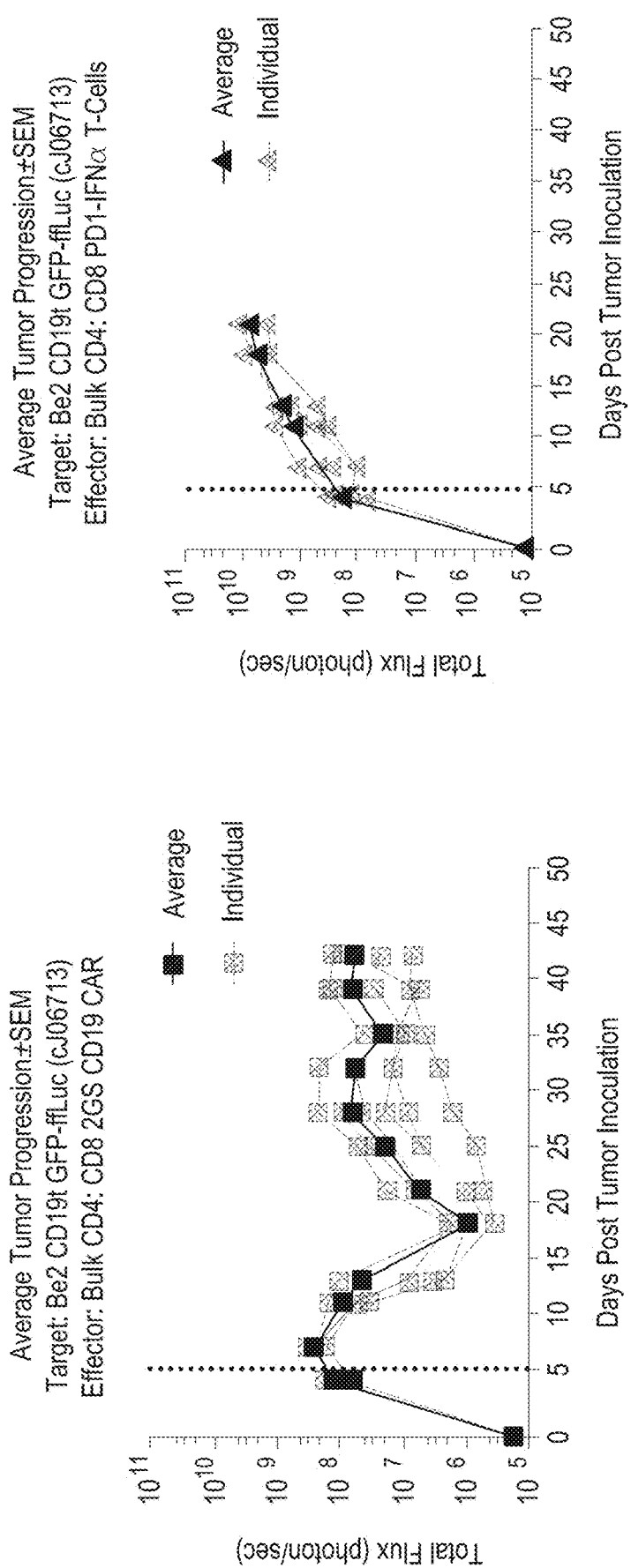
Figure 11:
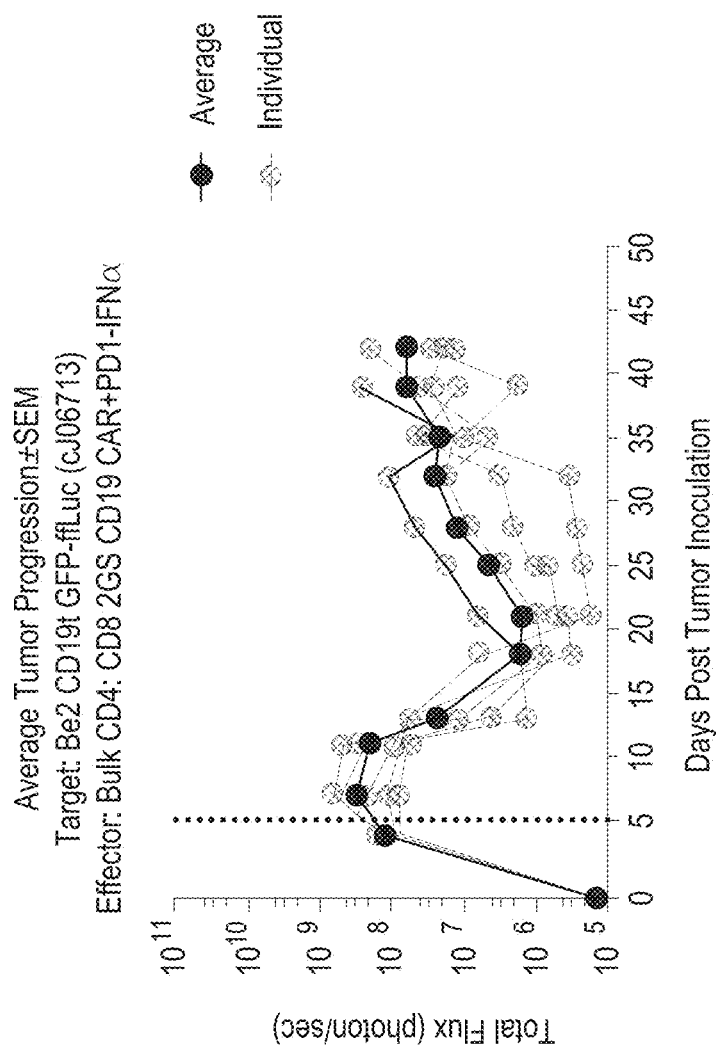

The In Vivo Antitumor Activity of CD19CAR− or CD19CAR and PD1-IFNα2a Expressing T-Cells 5e$^6$ Be2 CD19t eGFP:ffluc neuroblastoma cells were subcutaneously injected into the left and right flanks of NOD-SCID IL-2Ry null mice. Five days later 30e$^6$ T-cells at a 1:1 CD4:CD8 ratio were injected intravenously (i.v.) into the mice. Subsequent tumor volume measurements by caliper were performed as was imaged using D-luciferin and the IVIS imaging system. As shown in FIG. 11, CD19CAR and PD1-IFNα2a expressing T-cells were able to inhibit tumor growth at a similar rate to CD19CAR-alone expressing T-cells. As such, the alternatives as described herein can be used to inhibit tumor growth.

In some alternatives cells can be used in the treatment of subjects in need, wherein the subject has a cancer. In some alternatives, the cancer is a solid tumor. In some alternatives, the cells and compositions can be used to inhibit tumor growth.

Production and Secretion of PD1:IFNα2a Variants

Figure 12:
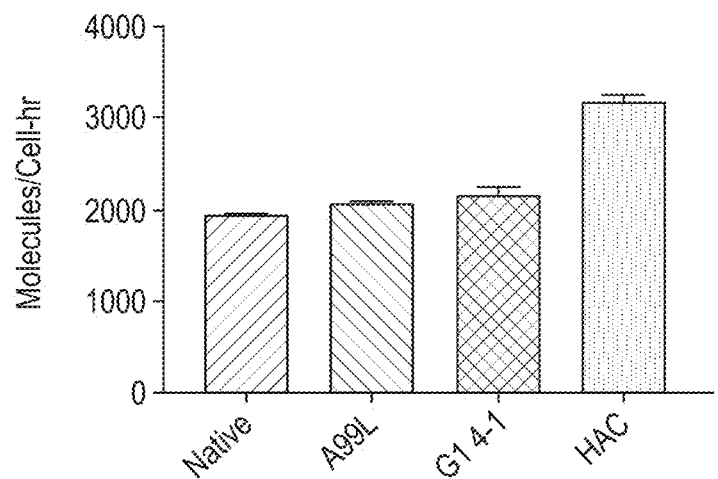
FIG. 12 shows that H9 T-cells are able to produce and secrete PD1:IFNα2a variants. H9 T-cells were transduced with EGFRt-T2A-PD1:IFNα2a vector or vector containing the A99L (Lazar-Molnar et al 2008 PNAS), G14-1 (Maute et al 2015 PNAS), or HAC-1 (Maute et al 2015 PNAS) mutant and then selected by EGFRt. Selected H9 cultures were washed in media to remove excess PD1:IFNα2a in supernatant. Supernatant from the H9 cultures was then harvested 24 hours later and concentrated using an Amicon Ultra-4 Centrifugal Filter Unit (Millipore) and subjected to an IFNα specific Bioplex Pro Inflammation Panel assay to quantify the presence of soluble PD1:IFNα2a in the supernatant in reference to an undiluted native IFNα (140000 pmol/mL or 140000 nM). Data is represented as molecules/cell-hr from 1e6 cells. Results demonstrate that all variants of the PD1:IFNα2a were produced at similar levels.

H9 T-cells were shown to be able to produce and secrete PD1:IFNα2a variants. H9 T-cells were transduced with EGFRt-T2A-PD1:IFNα2a vector or vector containing the A99L (Lazar-Molnar et al 2008 PNAS), G14-1 (Maute et al 2015 PNAS), or HAC-1(Maute et al 2015 PNAS) mutant and then selected by EGFRt. Selected H9 cultures were washed in media to remove excess PD1:IFNα2a in supernatant. Supernatant from the H9 cultures was then harvested 24 hours later and concentrated using an Amicon Ultra-4 Centrifugal Filter Unit (Millipore) and subjected to an IFNα specific Bioplex Pro Inflammation Panel assay to quantify the presence of soluble PD1:IFNα2a in the supernatant in reference to an undiluted native IFNα (140000 pmol/mL or 140000 nM). Data is represented as molecules/cell-hr from $1e^6$ cells. Results demonstrate that all variants of the PD1:IFNα2a were produced at similar levels (FIG. 12). As shown in the experiments, cells can be produced to have high levels or fusion protein expression.

As described in the alternatives herein, the EGFRt-T2A-PD1(G14-1):IFNα2a is encoded by the nucleic acid sequence set forth in SEQ ID NO: 17 (ATGCTTCTC CTGGTGACAA GCCTTCTGCT CTGTGAGTTA CCACACCCAG CATTCCTCCT GATCCCACGC AAAGTGTGTA ACGGAATAGG TATTGGTGAA TTTAAAGACT CACTCTCCAT AAATGCTACG AATATTAAAC ACTTCAAAAA CTGCACCTCC ATCAGTGGCG ATCTCCACAT CCTGCCGGTG GCATTTAGGG GTGACTCCTT CACACATACT CCTCCTCTGG ATCCACAGGA ACTGGATATT CTGAAAACCG TAAAGGAAAT CACAGGGTTT TTGCTGATTC AGGCTTGGCC TGAAAACAGG ACGGACCTCC ATGCCTTTGA GAACCTAGAA ATCATACGCG GCAGGACCAA GCAACATGGT CAGTTTTCTC TTGCAGTCGT CAGCCTGAAC ATAACATCCT TGGGATTACG CTCCCTCAAG GAGATAAGTG ATGGAGATGT GATAATTTCA GGAAACAAAA ATTTGTGCTA TGCAAATACA ATAAACTGGA AAAAACTGTT TGGGACCTCC GGTCAGAAAA CCAAAATTAT AAGCAACAGA GGTGAAAACA GCTGCAAGGC CACAGGCCAG GTCTGCCATG CCTTGTGCTC CCCCGAGGGC TGCTGGGGCC CGGAGCCCAG GGACTGCGTC TCTTGCCGGA ATGTCAGCCG AGGCAGGGAA TGCGTGGACA AGTGCAACCT TCTGGAGGGT GAGCCAAGGG AGTTTGTGGA GAACTCTGAG TGCATACAGT GCCACCCAGA GTGCCTGCCT CAGGCCATGA ACATCACCTG CACAGGACGG GGACCAGACA ACTGTATCCA GTGTGCCCAC TACATTGACG GCCCCCACTG CGTCAAGACC TGCCCGGCAG GAGTCATGGG AGAAAACAAC ACCCTGGTCT GGAAGTACGC AGACGCCGGC CATGTGTGCC ACCTGTGCCA TCCAAACTGC ACCTACGGAT GCACTGGGCC AGGTCTTGAA GGCTGTCCAA CGAATGGGCC TAAGATCCCG TCCATCGCCA CTGGGATGGT GGGGGCCCTC CTCTTGCTGC TGGTGGTGGC CCTGGGGATC GGCCTCTTCA TGGGCGGCGG AGAGGGCAGA GGAAGTCTTC TAACATGCGG TGACGTGGAG GAGAATCCCG GCCCTAGGAT GCAGATCCCT CAGGCCCCTT GGCCTGTCGT GTGGGCTGTG CTGCAGCTGG GATGGCGGCC TGGCTGGTTT CTGGACAGCC CCGACAGACC CTGGAACCCC CCTACATTTT CCCCTGCCCT GCTGGTCGTG ACCGAGGGCG ACAATGCCAC CTTCACCTGT AGCTTCAGCA ACACCAGCGA GAGCTTCAGA CTGGTGTGGC ATAGAGAAAG CCCCGGCTAC GAGACCGACA CTCTGGCCAG CTTCCCCGAG GATAGATCTA CCCCCCTGCC TGACTGCCGG TTCAGAGTGA CCCAGCTGCC CAACGGCCGG GACTTCCACA TGTCTGTCGT GCGGGCCAGA CGGAACGACA GCGGCACATA TGTTTGCGGC GCCATCGCCT TCCACCCCGT GATTCAGATC AAAGAGAGCC TGAGAGCCGA GCTGAGAGTG ACCGAGAGAA GGGCCGAAGT GCCTACCGCC CACCCTAGCC CATCTCCAAG ACCTGCCGGC CAGTTCCAGA CACTCGTGGG CGGAGGATGC GACCTGCCTC AGACACACAG CCTGGGCAGC AGACGGACCC TGATGCTGCT GGCCCAGATG CGGAAGATCA GCCTGTTCAG CTGCCTGAAG GACCGGCACG ACTTCGGCTT CCCTCAGGAA GAGTTCGGCA ACCAGTTTCA GAAGGCCGAG ACAATCCCCG TGCTGCACGA GATGATCCAG CAGATCTTCA ACCTGTTCTC CACCAAGGAC AGCAGCGCCG CCTGGGACGA GACACTGCTG GACAAGTTCT ACACCGAGCT GTACCAGCAG CTGAATGACC TGGAAGCCTG CGTGATCCAG GGCGTGGGCG TGACAGAGAC ACCCCTGATG AAGGAAGATA GCATCCTGGC CGTGCGCAAG TACTTCCAGC GGATCACCCT GTACCTGAAA GAGAAGAAGT ACAGCCCCTG CGCCTGGGAG GTCGTGCGCG CCGAGATCAT GAGAAGCTTC AGCCTGAGCA CCAACCTGCA GGAAAGCCTG CGGAGCAAAG AATAA; SEQ ID NO: 17).

Binding Affinity of PD1:IFNα2a Variants

Figure 13:
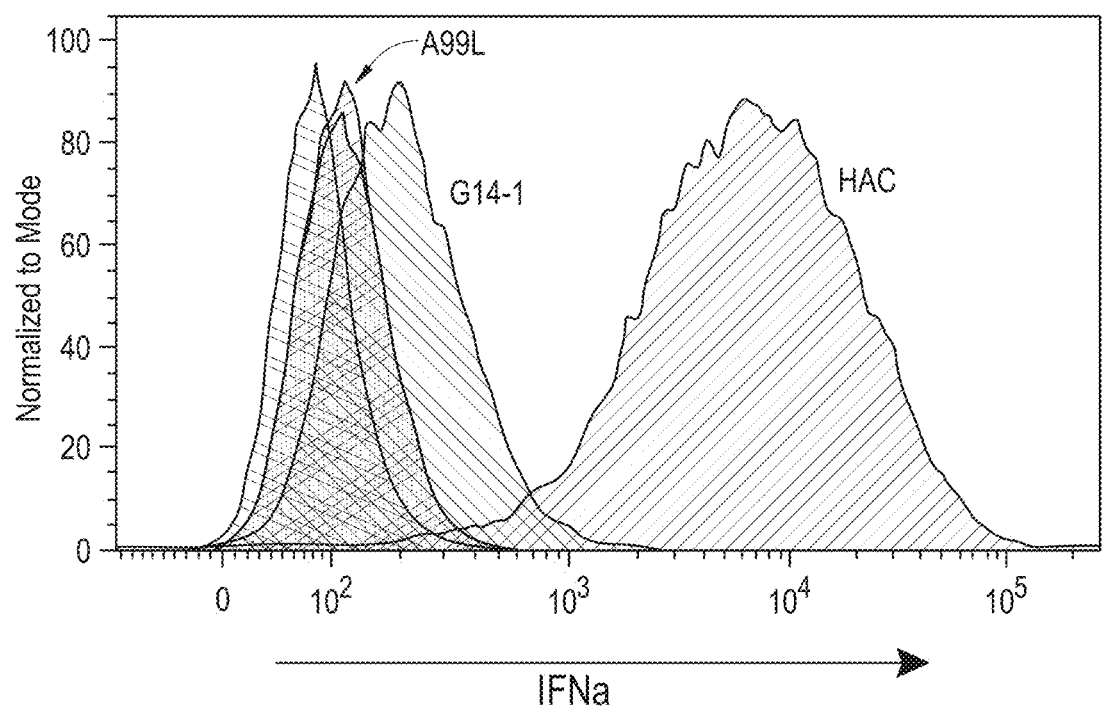
FIG. 13 shows that PD1:IFNα2a variants display higher binding affinity to PDL1 than wild-type PD1:IFNα2a. 1e6 PDL1-expressing U293T cells were harvested from culture and washed with PBS. Equal amounts of PD1:IFNα2a, PD1(A99L):IFNα2a, PD1(G14-1):IFNα2a, or PD1(HAC-1):IFNα2a as determined by Bioplex assay of culture supernatants was then added to the U293T cells for 20 min. Following incubation, cells were washed twice in PBS and then stained with PE-conjugated anti-IFNα antibody for 20 min. Cells were then washed twice in PBS and re-suspended in FACS fixative solution. Fixed cells were then run on the LSRFortessa for FACS analysis. Median fluorescence intensity differences between PD1:IFNα2a and variants demonstrate a higher level of PDL1 binding for some of the PD1 mutants.

PD1:IFNα2a variants were evaluated for their binding affinity in comparison to the wild-type PD1:IFNα2a. $1e^6$ PDL1-expressing U293T cells were harvested from culture and washed with PBS. Equal amounts of PD1:IFNα2a, PD1(A99L):IFNα2a, PD1(G14-1):IFNα2a, or PD1(HAC-1):IFNα2a as determined by Bioplex assay of culture supernatants were then added to the U293T cells for 20 minutes. Following incubation, cells were washed twice in PBS and then stained with PE-conjugated anti-IFNα antibody for 20 minutes. Cells were then washed twice in PBS and re-suspended in FACS fixative solution. Fixed cells were then run on the LSRFortessa for FACS (Fluorescence activated cell sorting) analysis. Median fluorescence intensity differences between PD1:IFNα2a and variants demonstrate a higher level of PDL1 binding for some of the PD1 mutants. As shown in FIG. 13, PD1:IFNα2a variants display higher binding affinity to PDL1 than wild-type PD1:IFNα2a.

In the alternatives herein, the PD1(HAC-1):IFNα2a is encoded by the nucleic acid sequence set forth in SEQ ID NO: 16 (ATGCTTC TCCTGGTGAC AAGCCTTCTG CTCTGTGAGT TACCACACCC AGCATTCCTC CTGATCCCAC GCAAAGTGTG TAACGGAATA GGTATTGGTG AATTTAAAGA CTCACTCTCC ATAAATGCTA CGAATATTAA ACACTTCAAA AACTGCACCT CCATCAGTGG CGATCTCCAC ATCCTGCCGG TGGCATTTAG GGGTGACTCC TTCACACATA CTCCTCCTCT GGATCCACAG GAACTGGATA TTCTGAAAAC CGTAAAGGAA ATCACAGGGT TTTGCTGAT TCAGGCTTGG CCTGAAAACA GGACGGACCT CCATGCCTTT GAGAACCTAG AAATCATACG CGGCAGGACC AAGCAACATG GTCAGTTTTC TCTTGCAGTC GTCAGCCTGA ACATAACATC CTTGGGATTA CGCTCCCTCA AGGAGATAAG TGATGGAGAT GTGATAATTT CAGGAAACAA AAATTTGTGC TATGCAAATA CAATAAACTG GAAAAAACTG TTTGGGACCT CCGGTCAGAA AACCAAAATT ATAAGCAACA GAGGTGAAAA CAGCTGCAAG GCCACAGGCC AGGTCTGCCA TGCCTTGTGC TCCCCCGAGG GCTGCTGGGG CCCGGAGCCC AGGGACTGCG TCTCTTGCCG GAATGTCAGC CGAGGCAGGG AATGCGTGGA CAAGTGCAAC CTTCTGGAGG GTGAGCCAAG GGAGTTTGTG GAGAACTCTG AGTGCATACA GTGCCACCCA GAGTGCCTGC CTCAGGCCAT GAACATCACC TGCACAGGAC GGGGACCAGA CAACTGTATC CAGTGTGCCC ACTACATTGA CGGCCCCCAC TGCGTCAAGA CCTGCCCGGC AGGAGTCATG GGAGAAAACA ACACCCTGGT CTGGAAGTAC GCAGACGCCG GCCATGTGTG CCACCTGTGC CATCCAAACT GCACCTACGG ATGCACTGGG CCAGGTCTTG AAGGCTGTCC AACGAATGGG CCTAAGATCC CGTCCATCGC CACTGGGATG GTGGGGGCCC TCCTCTTGCT GCTGGTGGTG GCCCTGGGGA TCGGCCTCTT CATGGGCGGC GGAGAGGGCA GAGGAAGTCT TCTAACATGC GGTGACGTGG AGGAGAATCC CGGCCCTAGG ATGCAGATCC CTCAGGCCCC TTGGCCTGTC GTGTGGGCTG TGCTGCAGCT GGGATGGCGG CCTGGCTGGT TTCTGGACAG CCCCGACAGA CCCTGGAACC CCCCTACATT TTCCCCTGCC CTGCTGGTCG TGACCGAGGG CGACAATGCC ACCTTCACCT GTAGCTTCAG CAACACCAGC GAGAGCTTCC ATGTTATTTG GCATAGAGAA AGCCCCAGCG GTCAGACCGA CACTCTGGCC GCCTTCCCCG AGGATAGATC TCAGCCCGGC CAGGACTGCC GGTTCAGAGT GACCCAGCTG CCCAACGGCC GGGACTTCCA CATGTCTGTC GTGCGGGCCA GACGGAACGA CAGCGGCACA TATGTTTGCG GCGTTATCAG CCTGGCCCCC AAGAT-TCAGA TCAAAGAGAG CCTGAGAGCC GAGCT-GAGAG TGACCGAGAG AAGGGCCGAA GTGCC-TACCG CCCACCCTAG CCCATCTCCA AGACCTGCCG GCCAGTTCCA GACACTCGTG GGCGGAGGAT GCGACCTGCC TCAGACACAC AGCCTGGGCA GCA-GACGGAC CCTGATGCTG CTGGCCCAGA TGCG-GAAGAT CAGCCTGTTC AGCTGCCTGA AGGACCGGCA CGACTTCGGC TTCCCTCAGG AAGAGTTCGG CAACCAGTTT CAGAAGGCCG AGACAATCCC CGTGCTGCAC GAGATGATCC AGCA-GATCTT CAACCTGTTC TCCACCAAGG ACAGCAGCGC CGCCTGGGAC GAGACACTGC TGGACAAGTT CTACACCGAG CTGTACCAGC AGCT-GAATGA CCTGGAAGCC TGCGTGATCC AGGGCGTGGG CGTGACAGAG ACACCCCTGA TGAAGGAAGA TAGCATCCTG GCCGTGCGCA AGTACTTCCA GCGGATCACC CTGTACCTGA AAGAGAAGAA GTACAGCCCC TGCGCCTGGG AGGTCGTGCG CGCCGAGATC ATGAGAAGCT TCAGCCTGAG CACCAACCTG CAGGAAAGCC TGCGGAGCAA AGAATAA; SEQ ID NO: 16).

More Alternatives

In some alternatives, a nucleic acid encoding a fusion protein is provided. The nucleic acid can comprise a first sequence, wherein the first sequence encodes a protein that modulates an immune response, a second sequence, wherein the second sequence encodes an amino acid spacer, such as a glycine spacer and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCA-GATCCCTCAGGCCCCTTGGCCTGTCGTGTGGGCT-GTGCTGCAGCTGG GATGGCGGCCTGGCTGGTTTCTGGACAGCCCCGA-CAGACCCTGGAACCCCCCT ACAT-TTTCCCCTGCCCTGCTGGTCGTGACCGAGGGCG-ACAATGCCACCTTCAC CTGTAGCTTCAGCAACACCAGCGAGAGCTTCGT-GCTGAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACCC-AGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (MQIPQAPWPVVWAVLQLGWRPGWFLDSPDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKAQIKESLRAELRVTERRAEVPTAHPSPSPRPAGQFQTLV; SEQ ID NO: 4). In some alternatives, PD-1 is a mutated form of PD-1 and comprises an amino acid sequence set forth in SEQ ID NO: 5 (MQIPQAPWPVVWAVLQLGWRPGWFLDSPDRPWNPPTFSPALLVVTEGDNATFTCSFSNTSESFVLNWYRMSPSNQTDKLAAFPEDRSQPGQDCRFRVTQLPNGRDFHMSVVRARRNDSGTYLCGAISLAPKLQIKESLRAELRVTERRAEVPTAHPSPSPRPAGQFQTLV; SEQ ID NO: 5). In some alternatives, PD-1 is a mutated form of PD-1 and comprises an amino acid sequence set forth in SEQ ID NO: 6 (MQIPQAPWPVVWAVLQLGWRPGWFLDSPDRPWNPPTFSPALLVVTEGDNATFTCSFSNTSESFHVVWHRESPSGQTDTLAAFPEDRSQPGQDCRFRVTQLPNGRDFHMSVVRARRNDSGTYVCGVISLAPKIQIKESLRAELRVTERRAEVPTAHPSPSPRPAGQFQTLV; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAGAATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGTAAGG; SEQ ID NO: 13). In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFNα2a. In some alternatives, the fusion protein stimulates the production of a cytokine. In some alternatives, the cytokine is CXCL10.

In some alternatives, a vector is provided. The vector can comprise the nucleic acid of anyone or more the alternatives described herein. The nucleic acid can comprise a first sequence, wherein the first sequence encodes a protein that modulates an immune response, a second sequence, wherein the second sequence encodes an amino acid spacer such as a glycine spacer and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGC-ACGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG- GAGAACCGTATATAAGTGCAGTAGTCGCCGT-GAACGTT CTTTTTCGCAACGGGTTTGCCGCCAGAACACAG-CTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCA-GATCCCTCAGGCCCCTTGGCCTGTCGTGTGGGC-TGTGCTGCAGCTGG GATGGCGGCCTGGCTGGTTTCTGGACAGCCCCGACA-GACCCTGGAACCCCCCT ACAT-TTTCCCCTGCCCTGCTGGTCGTGACCGAGGGC-GACAATGCCACCTTCAC CTGTAGCTTCAGCAACACCAGCGAGAGCTTCGTGCT-GAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACCC-AGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-GAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGCT-GTGCTGCAGCTGG GATGGCGG; SEQ ID NO: 12). In some alternatives, the CD19 signaling sequence is encoded by s a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as E. coli. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli. Secretion of the PD-1: IFNα2a fusion protein in CAR T-cells can be used to support T-cell activity, promote inflammatory cytokine production and decrease immunosuppression within the solid tumor microenvironment. The use of PD1-IFNa2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFNα2a. In some alternatives, the fusion protein stimulates the production of a cytokine. In some alternatives, the cytokine is CXCL10.

In some alternatives, a cell for fusion protein secretion is provided. The cell can comprise a nucleic acid of any one of the alternatives described herein or the expression vector of any one of the alternatives described herein. The nucleic acid can comprise a first sequence, wherein the first sequence encodes a protein that modulates an immune response, a second sequence, wherein the second sequence encodes an amino acid spacer such as a glycine spacer and a third sequence, wherein the third sequence encodes an interferon In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACA-GCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCA-GATCCCTCAGGCCCCTTGGCCTGTCGTGTGGGCT-GTGCTGCAGCTGG GATGGCGGCCTGGCTGGTTTCTGGACAGCCCC-GACAGACCCTGGAACCCCCCT ACAT-TTTCCCCTGCCCTGCTGGTCGTGACCGAGGGCGA-CAATGCCACCTTCAC CTGTAGCTTCAGCAACACCAGCGAGAGCTTCG-TGCTGAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACC-CAGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P NGRDFHMSVVRARRNDSGTYVCGVI SLAPKIQIKESLRAELRVTERRAEVPT AHPSPSPRPAGQFQTLV; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-GAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGC-TGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as *E. coli*. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as *E. coli*. In some alternatives, the cell is a bacterial cell or a mammalian cell, such as a lymphocyte or NK cell. In some alternatives, the cell is a bacterial cell, such as *E. coli*. In some alternatives, the cell is an insect cell for protein expression. In some alternatives, the cell is CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell or NK cell. In some alternatives, the cell is a B cell. In some alternatives, the cell is a neuronal stem cell. In some alternatives, the cell further comprises a chimeric antigen receptor. Secretion of the PD-1:IFNα2a fusion protein in CAR T-cells can be used to support T-cell activity, promote inflammatory cytokine production and decrease immunosuppression within the solid tumor microenvironment. The use of PD1-IFNα2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFnα2a. In some alternatives, the fusion protein stimulates the production of a cytokine. In some alternatives, the cytokine is CXCL10.

In some alternatives, method of making a chimeric antigen receptor bearing cell is provided. The method can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. In some alternatives, the chimeric antigen receptor is specific for CD19. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer, (e.g., glycine spacer), and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA- GACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGAT CAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (atgcttctcctggtgacaagccttctgctctgtgagttaccacacccagcattcctcctgatccca; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as E. coli. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. Secretion of the PD-1:IFNα2a fusion protein in CAR T-cells can be used to support T-cell activity, promote inflammatory cytokine production and decrease immunosuppression within the solid tumor microenvironment. The use of PD1-IFNa2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines.

In some alternatives, a composition is provided. In some alternatives, the composition comprises the cells of anyone of the alternatives described herein or the cells manufactured by the methods of anyone of the alternatives described herein. The method can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The vector can comprise the nucleic acid of anyone or more the alternatives described herein. The nucleic acid can comprise a first sequence, wherein the first sequence encodes a protein that modulates an immune response, a second sequence, wherein the second sequence encodes an amino acid spacer such as a glycine spacer and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as *E. coli*. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as *E. coli*. In some alternatives, the chimeric antigen receptor comprises a ligand binding domain, a polypeptide spacer of a length, wherein the length is optimized, a transmembrane domain, and a signaling domain. In some alternatives, the chimeric antigen receptor is specific for CD19. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+

T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. Secretion of the PD-1:IFNα2a fusion protein in CAR T-cells can be used to support T-cell activity, promote inflammatory cytokine production and decrease immunosuppression within the solid tumor microenvironment. The use of PD1-IFNa2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFnα2a. In some alternatives, the fusion protein stimulates the production of a cytokine. In some alternatives, the cytokine is CXCL10.

In some alternatives, a fusion protein is provided. The fusion protein can be encoded by the nucleic acid of anyone of the alternatives described herein or the vector of anyone of the alternatives described herein. The vector can comprise the nucleic acid of anyone or more the alternatives described herein. The nucleic acid can comprise a first sequence, wherein the first sequence encodes a protein that modulates an immune response, a second sequence, wherein the second sequence encodes an amino acid spacer such as a glycine spacer and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGG GAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-GAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGCT-GTGCTGCAGCTGG ATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13). In some alternatives, the vector is RNA or a DNA. In some alternatives, the vector is a viral vector. In some alternatives, the vector is for expres-sion of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as E. coli. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli. Secretion of the PD-1: IFNα2a fusion protein in CAR T-cells can be used to support T-cell activity, promote inflammatory cytokine production and decrease immunosuppression within the solid tumor microenvironment. The use of PD1-IFNa2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFnα2a. In some alternatives, the fusion protein stimulates the production of a cytokine. In some alternatives, the cytokine is CXCL10.

In some alternatives, a method of manufacturing a fusion protein for treatment is provided, wherein the method comprises delivering the nucleic acid of anyone of the alternatives described herein or the expression vector of anyone of the alternatives described herein to a bacterial cell, mammalian cell or insect cell, growing the cell up in a culture, inducing expression of the fusion protein and purifying the fusion protein for treatment. The vector can comprise the nucleic acid of anyone or more the alternatives described herein. The nucleic acid can comprise a first sequence, wherein the first sequence encodes a protein that modulates an immune response, a second sequence, wherein the second sequence encodes an amino acid spacer such as a glycine spacer and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGC-ACGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA- GACACTGCTGGACAAGTTCTACACCGAG CTGTACCAGCAGCTGAATGACCTGGAAGCCTGCGT-GATCCAGGGCGTGGGCG TGACAGAGACACCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACAG-CTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCA-GATCCCTCAGGCCCCTTGGCCTGTCGTGTGGGCT-GTGCTGCAGCTGG GATGGCGGCCTGGCTGGTTTCTGGACAGCCCCG-ACAGACCCTGGAACCCCCT ACAT-TTTCCCCTGCCCTGCTGGTCGTGACCGAGGGCGA-CAATGCCACCTTCAC CTGTAGCTTCAGCAACACCAGCGAGAGCTTCGT-GCTGAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACCC-AGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-GAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA- GATCCCTCAGGCCCCTTGGCCTGTCGTGTGGG-CTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCTCCCA-GACTTCTCTTTTTCCTCCTCTTCCTGACGCCGATG-GAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as E. coli. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli. In some alternatives, inducing comprises adding IPTG, anhydrotetracycline, L-arabinose or rhamnose to the culture. In some alternatives, the cell is E. coli. In some alternatives, the cell is an insect-cell. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFNα2a. In some alternatives, the fusion protein stimulates the production of a cytokine. In some alternatives, the cytokine is CXCL10.

In some alternatives, a method of secreting the fusion protein of anyone of the alternatives, is provided, wherein the method comprises delivering to a subject the cell of anyone of the alternatives described herein or the composition of anyone of the alternatives described herein. In some alternatives, the composition comprises the cells of anyone of the alternatives described herein or the cells manufactured by the methods of anyone of the alternatives described herein. The method can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer (e.g., a plurality of glycines) and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACAG-CTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCA-GATCCCTCAGGCCCCTTGGCCTGTCGTGTGGGC-TGTGCTGCAGCTGG GATGGCGGCCTGGCTGGTTTCTGGACAGCCCCG-ACAGACCCTGGAACCCCCCT ACAT-TTTCCCCTGCCCTGCTGGTCGTGACCGAGGGCG-ACAATGCCACCTTCAC CTGTAGCTTCAGCAACACCAGCGAGAGCTTCGTG-CTGAACTGGTACAGAATG AGCCCCAGCAACCA-GACCGACAAGCTGGCCGCCTTCCCCGAGGATA- GATCTC
AGCCCGGCCAGGACTGCCGGTTCAGAGTGACCCA-
GCTGCCCAACGGCCGGGA CTTCCA-
CATGTCTGTCGTGCGGGCCAGACG-
GAACGACAGCGGCACATATCTGT
GCGGCGCCATCAGCCTGGCCCCCAAGGCCCAGAT-
CAAAGAGAGCCTGAGAGC CGAGCT-
GAGAGTGACCGAGAGAAGGGCCGAAGTGCC-
TACCGCCCACCCTAGC
CCATCTCCAAGACCTGCCGGCCAGTTCCA-
GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-
GAGAGGGCAGAGGAAGTCTTCTAA-
CATGCGGTGACGTGGAGGAG
AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-
GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-
GATCCCTCAGGCCCCTTGGCCTGTCGTGTGGG-
CTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCTCCCA-
GACTTCTCTTTTTCCTCCTCTTCCTGACGCCGATG-
GAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as E. coli. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives the chimeric antigen receptor is specific for CD19. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. In some alternatives, the method further comprises administering to the subject an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. Secretion of the PD-1:IFNα2a fusion protein in CAR T-cells can be used to support T-cell activity, promote inflammatory cytokine production and decrease immunosuppression within the solid tumor microenvironment. The use of PD1-IFNα2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFnα2a. In some alternatives, the fusion protein stimulates the production of a cytokine. In some alternatives, the cytokine is CXCL10.

In some alternatives, a method of increasing T-cell activity is provided, wherein the method comprises administering an effective amount of the cell of anyone of the alternatives described herein or the composition of anyone of the alternatives described herein, wherein the cells of the composition express a chimeric antigen receptor that comprises an antigen binding domain that binds to a tumor antigen expressed on a cancer cell, or the fusion protein of anyone of the alternatives described herein to a subject in need. In some alternatives, the composition comprises the cells of anyone of the alternatives described herein or the cells manufactured by the methods of anyone of the alternatives described herein. The method can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. In some alternatives, the chimeric antigen receptor is specific for CD19. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer (e.g., a plurality of glycines) and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAG- CATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-GAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGCTG-TGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGTAAGG; SEQ ID NO: 13). In some alternatives, the vector is RNA or DNA. In some alternatives, the vector is a viral vector. In some alternatives, the vector is for expression of a protein in a bacterial, mammalian or insect system. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. The fusion protein can be encoded by the nucleic acid of anyone of the alternatives described herein or the vector of anyone of the alternatives described herein. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer (e.g., a plurality of glycines) and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACAG-CTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPINs, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCA-GATCCCTCAGGCCCCTTGGCCTGTCGTGTGGGC-TGTGCTGCAGCTGG GATGGCGGCCTGGCTGGTTTCTGGACAGCCCCG-ACAGACCCTGGAACCCCCT ACAT-TTTCCCCTGCCCTGCTGGTCGTGACCGAGGGCGA-CAATGCCACCTTCAC CTGTAGCTTCAGCAACACCAGCGAGAGCTTCGTG-CTGAACTGGTACAGAATG AGCCCCAGCAACCA-GACCGACAAGCTGGCCGCCTTCCCCGAGGATA-GATCTC AGCCCGGCCAGGACTGCCGGTTCAGAGTGACCC-AGCTGCCCAACGGCCGGGA CTTCCA-CATGTCTGTCGTGCGGGCCAGACG-GAACGACAGCGGCACATATCTGT GCGGCGCCATCAGCCTGGCCCCCAAGGCCCAGAT-CAAAGAGAGCCTGAGAGC CGAGCT-GAGAGTGACCGAGAGAAGGGCCGAAGTGCC-TACCGCCCACCCTAGC CCATCTCCAAGACCTGCCGGCCAGTTCCA-GACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-GAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGC-TGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG- GAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as *E. coli*. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as *E. coli*. In some alternatives, the administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. Secretion of the PD-1:IFNa2a fusion protein in CAR T-cells can be used to support T-cell activity, promote inflammatory cytokine production and decrease immunosuppression within the solid tumor microenvironment. The use of PD1-IFNa2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFnα2a. In some alternatives, the fusion protein stimulates the production of a cytokine. In some alternatives, the cytokine is CXCL10.

In some alternatives, a method of decreasing immunosuppression in a tumor microenvironment comprising administering an effective amount of the cell of anyone of the alternatives described herein or the composition of anyone of the alternatives described herein, wherein the cells of the composition express a chimeric antigen receptor that comprises an antigen binding domain that binds to a tumor antigen expressed on a cancer cell, or the fusion protein of anyone of the alternatives described herein to a subject in need. In some alternatives, the chimeric antigen receptor is specific for CD19. The method can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer (e.g., a plurality of glycines) and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGCA-CGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT-GAAAGAGAAGAAGTACAGCCCCTGCGCC TGG-GAGGTCGTGCGCGCCGAGATCAT-GAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGC-GATCGCTCCGGTGCCCGTCAGTGGGCAGAGCGCA-CATCGCCCAC AGTCCCCGAGAAGTTGGGGG-GAGGGGTCGGCAATTGAACCGGTGCCTAGAGA AGGTGGCGCGGGGTAAACTGGGAAAGT-GATGTCGTGTACTGGCTCCGCCTTTT TCCCGAGGGTGGGG-GAGAACCGTATATAAGTGCAGTAGTCGCCGT-GAACGTT CTTTTTCGCAACGGGTTTGCCGCCAGAACACA-GCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPINs, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids, such as glycines, or a number of amino acids, such as glycines, within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (atgatctcctggtgacaagccttctgctctgtgagttaccacacccagcat-tcctcctgatccca; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as *E. coli*. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as *E. coli*. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. The fusion protein can be encoded by the nucleic acid of anyone of the alternatives described herein or the vector of anyone of the alternatives described herein. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer (e.g., a plurality of glycines) and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGTGATCCAGGGCGTGGGCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGAGAACCGTATATAAGTGCAGTAGTCGCCGTGAACGTT CTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO:7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-GAGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence comprises a nucleic acid sequence set forth in SEQ ID NO: 12 (ATGCA-GATCCCTCAGGCCCCTTGGCCTGTCGTGTGGGCT-GTGCTGCAGCTGG GATGGCGG; SEQ ID NO: 12). In some alternatives, the CD19 signaling sequence comprises a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as E. coli. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as E. coli. In some alternatives, the administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. Secretion of the PD-1:IFNα2a fusion protein in CAR T-cells can be used to support T-cell activity, promote inflammatory cytokine production and decrease immunosuppression within the solid tumor microenvironment. The use of PD1-IFNa2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFNα2a. In some alternatives, the fusion protein stimulates the production of a cytokine. In some alternatives, the cytokine is CXCL10.

In some alternatives, a method of treating patient having a cancer expressing a tumor antigen is provided. The method can comprise administering an effective amount of the cell of anyone of the alternatives described herein or the composition of anyone of the alternatives described herein, wherein the cells of the composition express a chimeric antigen receptor that comprises an antigen binding domain that binds to a tumor antigen expressed on a cancer cell, or the fusion protein of anyone of the alternatives described herein to the patient. In some alternatives, the chimeric antigen receptor is specific for CD19. The method can comprise delivering to a cell, the nucleic acid of anyone of the alternatives described herein or the expression vector of anyone of the alternatives described herein and delivering to the cell, a second nucleic acid, wherein the second nucleic acid encodes a chimeric antigen receptor. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer (e.g., a plurality of glycines) and a third sequence, wherein the third sequence encodes an interferon. The first sequence, second sequence and third sequence can be in any order in the nucleic acid. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCA-GACACACAGCCTGGGCAGCAGACGGACCCT-GATGCTGC TGGCCCAGATGCGGAA-GATCAGCCTGTTCAGCTGCCTGAAGGACCGGC-ACGA CTTCGGCTTCCCTCAG-GAAGAGTTCGGCAACCAGTTTCAGAAGGCCGA-GACA ATCCCCGTGCTGCACGAGATGATCCAGCA-GATCTTCAACCTGTTCTCCACCAA GGACAGCAGCGCCGCCTGGGACGA-GACACTGCTGGACAAGTTCTACACCGAG CTGTACCAGCAGCTGAATGACCTGGAAGCCTGCGT-GATCCAGGGCGTGGGCG TGACAGAGACACCCCT-GATGAAGGAAGATAG-CATCCTGGCCGTGCGCAAGTA CTTCCAGCGGATCACCCTGTACCT- GAAAGAGAAGAAGTACAGCCCCTGCGCC TGGGAGGTCGTGCGCCGAGATCATGAGAAGCTTCAGCCTGAGCACCAACCTGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGAAGGTGGCGCGGGGTAAACTGGGAAAGTGATGTCGTGTACTGGCTCCGCCTTTTTCCCGAGGGTGGGGGAGAACCGTATATAAGTGCAGTAGTCGCCGTGAACGTTCTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATAGATCTC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGCCCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCGGAGAGGGCAGAGGAAGTCTTCTAACATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGTGAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCAGATCCCTCAGGCCCCTTGGCCTGTCGTGTGGGCTGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCAGACTTCTCTTTTTCCTCCTCTTCCTGACGCCGATGGAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as *E. coli*. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as *E. coli*. In some alternatives, the chimeric antigen receptor comprises a ligand binding domain, a polypeptide spacer of a length, wherein the length is optimized, a transmembrane domain, and a signaling domain. In some alternatives, the polypeptide spacer is 3, 4, 5, 6, 7, 8, 9, 10, 11, 12, 13, 14 or 15 amino acids in length or a length within a range defined by any two of the aforementioned lengths. In some alternatives, the signaling domain comprises all of a portion of CD3 zeta in combination with a costimulatory domain selected from the group consisting of CD27, CD28, 4-1BB, OX-40, CD30, CD40, PD-1, ICOS, LFA-1, CD2, CD7, NKG2C, and B7-H3 or combinations thereof. In some alternatives, the ligand binding domain is specific for tumor expressed protein, PDL1 or IFNAR. In some alternatives, the cell is a CD8+ or a CD4+ cell. In some alternatives, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some alternatives, the cell is a CD4+ T helper lymphocyte cell that is selected from the group consisting of naïve CD4+ T-cells, central memory CD4+ T-cells, effector memory CD4+ T-cells, and bulk CD4+ T-cells. In some alternatives, the cell is a precursor T-cell. In some alternatives, the cell is a stem cell. In some alternatives, the cell is a hematopoietic stem cell. In some alternatives, the cell is a B cell. In some alternatives, the cell is a neuronal stem cell. The fusion protein can be encoded by the nucleic acid of anyone of the alternatives described herein or the vector of anyone of the alternatives described herein. The vector can comprise the nucleic acid of anyone or more the alternatives described herein. The nucleic acid can comprise a first sequence, wherein the first sequence encodes a protein that modulates an immune response, a second sequence, wherein the second sequence encodes a spacer, such as an amino acid spacer (e.g., a plurality of glycines) and a third sequence, wherein the third sequence encodes an interferon. In some alternatives, a 3' terminus of the first sequence is adjacent to a 5' terminus of the second sequence and a 3' terminus of the second sequence is adjacent to a 5' terminus of the third sequence. In some alternatives, the interferon is IFN-α, IFNα2a, IFN-β, IFN-ε, IFN-κ or IFN-ω. In some alternatives, the interferon is IFNα2a. In some alternatives, the third sequence comprises a nucleic acid sequence set forth in SEQ ID NO: 1 (TGCGACCTGCCTCAGACACACAGCCTGGGCAGCAGACGGACCCTGATGCTGC TGGCCCAGATGCGGAAGATCAGCCTGTTCAGCTGCCTGAAGGACCGGCACGA CTTCGGCTTCCCTCAGGAAGAGTTCGGCAACCAGTTTCAGAAGGCCGAGACA ATCCCCGTGCTGCACGAGATGATCCAGCAGATCTTCAACCTGTTCTCCACCAA GGACAGCAGCGCCGCCTGGGACGAGACACTGCTGGACAAGTTCTACACCGAG CTGTACCAGCAGCTGAATGACCTGGAAGCCTGCGT- GATCCAGGGCGTGGGCCG TGACAGAGACACCCCTGATGAAGGAAGATAGCATCCTGGCCGTGCGCAAGTA CTTCCAGCGGATCACCCTGTACCTGAAAGAGAAGAAGTACAGCCCCTGCGCC TGGGAGGTCGTGCGCGCCGAGATCATGAGAAGCTTCAGCCTGAGCACCAACC TGCAGGAAAGCCTGCGGAGCAAAGAA; SEQ ID NO: 1). In some alternatives, the nucleic acid further comprises a fourth sequence, wherein the fourth sequence encodes a promoter. In some alternatives, the promoter is a mammalian promoter for mammalian cell protein expression or a bacterial promoter for bacterial cell protein expression. In some alternatives, the promoter is an inducible promoter or a constitutive promoter. In some alternatives, the promoter is EF1P. In some alternatives, the fourth sequence comprises a nucleic acid sequence set forth in SEQ ID NO: 2 (GGATCTGCGATCGCTCCGGTGCCCGTCAGTGGGCAGAGCGCACATCGCCCAC AGTCCCCGAGAAGTTGGGGGGAGGGGTCGGCAATTGAACCGGTGCCTAGAGA AGGTGGCGCGGGGTAAACTGGGAAAGTGATGTCGTGTACTGGCTCCGCCTTTT TCCCGAGGGTGGGGGAGAACCGTATATAAGTGCAGTAGTCGCCGTGAACGTT CTTTTTTCGCAACGGGTTTGCCGCCAGAACACAGCTG; SEQ ID NO: 2). In some alternatives, the promoter is a T7 promoter, lac promoter, trc promoter, tac promoter, tetA promoter, araBAD promoter or a rhaPBAD promoter. In some alternatives, the promoter is inducible by IPTG, anhydrotetracycline, L-arabinose or rhamnose. In some alternatives, the promoter is regulated by a drug. In some alternatives, the drug is tamoxifen. In some alternatives, the promoter is a regulatable promoter, regulated by a CAR-dependent signal. In some alternatives, the promoter is an NFAT regulated promoter system. In some alternatives, the first sequence encodes PD-1, antigen specific binding domains, antigen specific scFvs, an extracellular domain, DARPins, affinity peptides, extracellular proteins expressed by tumor cells, peptides, tumor specific extracellular proteins, Her2, ROR1, embryonal fibronectin or an extracellular matrix protein. In some alternatives, the extracellular protein is fibronectin, laminin or collagen. In some alternatives, PD-1 is a wild type PD-1 or a mutated or truncated form of PD-1. In some alternatives, the first sequence comprises a nucleic acid sequence set forth in SEQ ID NO: 3 (ATGCAGATCCCTCAGGCCCCTTGGCCTGTCGTGTGGGCTGTGCTGCAGCTGG GATGGCGGCCTGGCTGGTTTCTGGACAGCCCCGACAGACCCTGGAACCCCCCT ACATTTTCCCCTGCCCTGCTGGTCGTGACCGAGGGCGACAATGCCACCTTCAC CTGTAGCTTCAGCAACACCAGCGAGAGCTTCGTGCTGAACTGGTACAGAATG AGCCCCAGCAACCAGACCGACAAGCTGGCCGCCTTCCCCGAGGATATC AGCCCGGCCAGGACTGCCGGTTCAGAGTGACCCAGCTGCCCAACGGCCGGGA CTTCCACATGTCTGTCGTGCGGGCCAGACGGAACGACAGCGGCACATATCTGT GCGGCGCCATCAGCCTGGCCCCCAAGGCCCAGATCAAAGAGAGCCTGAGAGC CGAGCTGAGAGTGACCGAGAGAAGGGCCGAAGTGCCTACCGCCCACCCTAGC CCATCTCCAAGACCTGCCGGCCAGTTCCAGACACTCGTG; SEQ ID NO: 3). In some alternatives, PD-1 comprises an amino acid sequence set forth in SEQ ID NO: 4 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K A Q I K E S L R A E L R V T E R R A E V P T A H P S P S P R P A G Q F Q T L V; SEQ ID NO: 4). In some alternatives, PD-1 is a mutated form of PD-1 and comprises an amino acid sequence set forth in SEQ ID NO: 5 (M Q I P Q A P W P V V W A V L Q L G W R P G W F L D S P D R P W N P P T F S P A L L V V T E G D N A T F T C S F S N T S E S F V L N W Y R M S P S N Q T D K L A A F P E D R S Q P G Q D C R F R V T Q L P N G R D F H M S V V R A R R N D S G T Y L C G A I S L A P K L Q I K E S L R A E L R V T E R R A E V P T A H P S P S P R P A G Q F Q T L V; SEQ ID NO: 5). In some alternatives, PD-1 is a mutated form of PD-1 and comprises an amino acid sequence set forth in SEQ ID NO: 6 (M Q I P Q A P W P V V W A V L Q L G W R P G W F L D S P D R P W N P P T F S P A L L V V T E G D N A T F T C S F S N T S E S F H V V W H R E S P S G Q T D T L A A F P E D R S Q P G Q D C R F R V T Q L P N G R D F H M S V V R A R R N D S G T Y V C G V I S L A P K I Q I K E S L R A E L R V T E R R A E V P T A H P S P S P R P A G Q F Q T L V; SEQ ID NO: 6). In some alternatives, the nucleic acid is a DNA or an RNA. In some alternatives, the amino acid spacer comprises 1, 2, 3, 4, 5, 6, 7, 8, 9 or 10 amino acids (e.g., glycines) or a number of amino acids (e.g., glycines) within a range defined by any two of the aforementioned numbers. In some alternatives, the amino acid spacer comprises at least 3 glycines. In some alternatives, the amino acid spacer comprises a sequence set forth in SEQ ID NO: 7 (GGGS; SEQ ID NO: 7), SEQ ID NO: 8 (GGGSGGG; SEQ ID NO: 8) or SEQ ID NO: 9 (GGG; SEQ ID NO: 9). In some alternatives, the nucleic acid further comprises a fifth sequence encoding a 2A linker, wherein the 2A linker is between the fusion protein and a protein for co-expression. In some alternatives, the 2A linker is a T2A linker, a P2A linker or an E2A linker. In some alternatives, the fifth sequence comprises a nucleic acid sequence encoding a T2A linker and comprises a nucleic acid sequence set forth in SEQ ID NO: 10 (GGCGGCG-AGAGGGCAGAGGAAGTCTTCTAA-CATGCGGTGACGTGGAGGAG AATCCCGGCCCTAGG; SEQ ID NO: 10) and further comprises a sequence encoding a protein for co-expression. In some alternatives, the nucleic acid further comprises a sixth sequence encoding an IRES sequence. In some alternatives, the nucleic acid further comprises a seventh sequence encoding a marker. In some alternatives, the marker is Her2tG or EGFRt. In some alternatives, the nucleic acid further comprises an eighth sequence, wherein the eighth sequence encodes a signal for protein secretion. In some alternatives, PD-1 further comprises a signaling domain for secretion. In some alternatives, the signal for protein secretion is a GMCSF signaling sequence, PD-1 signaling sequence or CD19 signaling sequence. In some alternatives, the GMCSF signaling sequence is encoded by a nucleic acid sequence set forth in SEQ ID NO: 11 (ATGCTTCTCCTGGTGACAAGCCTTCTGCTCTGT-GAGTTACCACACCCAGCATT CCTCCTGATCCCA; SEQ ID NO: 11). In some alternatives, the PD-1 signaling sequence is encoded by a nucleic acid sequence set forth in SEQ ID NO: 12 (ATGCA-GATCCCTCAGGCCCCTTGGCCTGTCGTGTGGGC-TGTGCTGCAGCTGG GATGGCGG; SEQ ID NO: 12). In some alternatives, the CD19 signaling sequence is encoded by a nucleic acid sequence set forth in SEQ ID NO: 13 (ATGCCCCCTCCCA-GACTTCTCTTTTTCCTCCTCTTCCTGACGCCGATG-GAAGT AAGG; SEQ ID NO: 13). In some alternatives, the vector is RNA or DNA. In some alternatives, the vector is a viral vector. In some alternatives, the vector is for expression of a protein in a bacterial, mammalian or insect system. Vectors include but are not limited to plasmid, minicircles, yeast, and viral genomes. In some alternatives, the vectors are plasmid, minicircles, yeast, or viral genomes. In some alternatives, the vector is a viral vector. In some alternatives, the viral vector is a lentivirus. In some alternatives, the vector is for protein expression in a bacterial system such as *E. coli*. In some alternatives, the vector is a lentiviral vector. In some alternatives, the vector is a foamy viral vector, adenoviral vectors, retroviral vectors or lentiviral vectors. In some alternatives, the vector is for protein expression in a bacterial system, such as *E. coli*. In some alternatives, the administering is performed by delivering the composition to a tumor site. In some alternatives, the method further comprises monitoring the cells of the composition by detection of Her2tG or EGFRt markers. In some alternatives, the method further comprises administering an effective amount of tamoxifen, its metabolites, analogs, and pharmaceutically acceptable salts and/or hydrates or solvates thereof. In some alternatives, the effective amount is 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg or any amount within a range defined by any two of the aforementioned numbers. In some alternatives, the administering is performed 1, 2 or 3 times a day. In some alternatives, the fusion protein can be scFv based and be used to target cytokines. Without being limiting, the cytokines for targeting can be IL4, IL6 or IL10. Targeting these cytokines would help to limit the immunosuppressive effects of the cytokines. Secretion of the PD-1:IFNα2a fusion protein in CAR T-cells can be used to support T-cell activity, promote inflammatory cytokine production and decrease immunosuppression within the solid tumor microenvironment. The use of PD1-IFNα2a will have most use against solid tumors that express targets such as EGFRvIII, Her2, L1CAM, oaGD2, GD2, ROR1, B7H3, IL13Ra2 and/or EphA2, for example, where the tumor microenvironment plays a larger role in tumor progression. In some alternatives, the fusion protein stimulates the production of stimulates the production of MIP-1a. In some alternatives herein, the fusion protein stimulates the production of MIP-1b. In some alternatives, the fusion protein stimulates the production of a cytokine. In some alternatives, the cytokine is CXCL9. In some alternatives, the fusion protein comprises PD1. In some alternatives, the fusion protein comprises IFnα2a. In some alternatives, the fusion protein stimulates the production of a cytokine. In some alternatives, the cytokine is CXCL10.

What is claimed is:

1. A nucleic acid encoding a fusion protein, the nucleic acid comprising:
   a first polynucleotide encoding an extracellular domain of a mutant PD-1 protein selected from a PD-1 extracellular domain of a protein encoded by the nucleotide sequence of any one of SEQ ID NOs 14, 16 or 17;
   a second polynucleotide encoding a spacer; and
   a third polynucleotide encoding an interferon-α2 protein;
   wherein the fusion protein comprising the extracellular domain of a mutant PD-1 protein is capable of specifically binding to a PD-L1 protein with an increased affinity compared to a fusion protein comprising an extracellular domain of a wild-type PD-1 protein.

2. The nucleic acid of claim 1, wherein the extracellular domain of a mutant PD-1 protein comprises the amino acid sequence of SEQ ID NO:05, or SEQ ID NO:06.

3. The nucleic acid of claim 1, wherein the interferon-α2 protein is IFNα2a.

4. The nucleic acid of claim 3, wherein the IFNα2a is encoded by the nucleotide sequence of SEQ ID NO:01.

5. The nucleic acid of claim 1, wherein the spacer comprises at least 3 consecutive glycine residues.

6. The nucleic acid of claim 5, wherein the spacer comprises the amino acid sequence selected from the group consisting of SEQ ID NO:07, SEQ ID NO:08, and SEQ ID NO:09.

7. The nucleic acid of claim 1, further comprising an elongation factor-1 (EF-1) promoter.

8. The nucleic acid of claim 1, further comprising:
   a polynucleotide encoding a marker selected from a truncated HER2 polypeptide (Her2tG) or a truncated epidermal growth factor receptor polypeptide (EGFRt); and
   a polynucleotide encoding a T2A self-cleaving linker, wherein the polynucleotide encoding a T2A self-cleaving linker is located between the nucleic acid encoding the fusion protein and the polynucleotide encoding the marker.

9. A vector comprising the nucleic acid of claim 1.

10. The vector of claim 9, wherein the vector comprises a lentiviral vector.

11. A cell comprising the nucleic acid of claim 1.

12. The cell of claim 11, further comprising a nucleic acid encoding a chimeric antigen receptor (CAR).

13. The cell of claim 12, wherein the CAR comprises an anti-CD19 CAR.

14. The cell of claim 11, wherein the cell is selected from a lymphocyte, a NK cell, a precursor T-cell, a stem cell, a hematopoietic stem cell, a NK cell, a neuronal stem cell, or a B cell.

15. The cell of claim 11, wherein the cell is a CD8+ T cell or a CD4+ T cell.

16. The nucleic acid of claim 1, wherein the extracellular domain of a wild-type PD-1 protein comprises the amino acid sequence of SEQ ID NO:04.

17. The nucleic acid of claim 1, wherein the extracellular domain of a mutant PD-1 protein comprises the amino acid sequence of SEQ ID NO:05.

18. The nucleic acid of claim 1, wherein the extracellular domain of a mutant PD-1 protein is selected from a PD-1 extracellular domain of a protein encoded by the nucleotide sequence of SEQ ID NO:16, or SEQ ID NO:17.

19. A nucleic acid encoding a fusion protein, the nucleic acid comprising:
- a first polynucleotide encoding an extracellular domain of a PD-1 comprising the amino acid sequence of SEQ ID NO:05 or SEQ ID NO:06;
- a second polynucleotide encoding a spacer; and
- a third polynucleotide encoding an interferon, wherein the interferon is encoded by the nucleotide sequence of SEQ ID NO:01.

* * * * *

SEQUENCE LISTING

```
<160> NUMBER OF SEQ ID NOS: 17

<210> SEQ ID NO 1
<211> LENGTH: 495
<212> TYPE: DNA
<213> ORGANISM: Artificial Sequence
<220> FEATURE:
```

<223> OTHER INFORMATION: IFNa2a

<400> SEQUENCE: 1

| | | | | | |
|---|---|---|---|---|---|
| tgcgacctgc | ctcagacaca | cagcctgggc | agcagacgga | ccctgatgct | gctggcccag | 60 |
| atgcggaaga | tcagcctgtt | cagctgcctg | aaggaccggc | acgacttcgg | cttccctcag | 120 |
| gaagagttcg | gcaaccagtt | tcagaaggcc | gagacaatcc | ccgtgctgca | cgagatgatc | 180 |
| cagcagatct | tcaacctgtt | ctccaccaag | gacagcagcg | ccgcctggga | cgagacactg | 240 |
| ctggacaagt | tctacaccga | gctgtaccag | cagctgaatg | acctggaagc | tgcgtgatc | 300 |
| cagggcgtgg | gcgtgacaga | gacaccctg | atgaaggaag | atagcatcct | ggccgtgcgc | 360 |
| aagtacttcc | agcggatcac | cctgtacctg | aaagagaaga | agtacagccc | ctgcgcctgg | 420 |
| gaggtcgtgc | gcgccgagat | catgagaagc | ttcagcctga | gcaccaacct | gcaggaaagc | 480 |
| ctgcggagca | aagaa | | | | | 495 |

<210> SEQ ID NO 2
<211> LENGTH: 245
<212> TYPE: DNA
<213> ORGANISM: Artificial Sequence
<220> FEATURE:
<223> OTHER INFORMATION: EF1p domain

<400> SEQUENCE: 2

| | | | | | |
|---|---|---|---|---|---|
| ggatctgcga | tcgctccggt | gcccgtcagt | gggcagagcg | cacatcgccc | acagtccccg | 60 |
| agaagttggg | gggaggggtc | ggcaattgaa | ccggtgccta | gagaaggtgg | cgcggggtaa | 120 |
| actgggaaag | tgatgtcgtg | tactggctcc | gcctttttcc | cgagggtggg | ggagaaccgt | 180 |
| atataagtgc | agtagtcgcc | gtgaacgttc | tttttcgcaa | cgggtttgcc | gccagaacac | 240 |
| agctg | | | | | | 245 |

<210> SEQ ID NO 3
<211> LENGTH: 510
<212> TYPE: DNA
<213> ORGANISM: Artificial Sequence
<220> FEATURE:
<223> OTHER INFORMATION: PD1ECD

<400> SEQUENCE: 3

| | | | | | |
|---|---|---|---|---|---|
| atgcagatcc | ctcaggcccc | ttggcctgtc | gtgtgggctg | tgctgcagct | gggatggcgg | 60 |
| cctggctggt | ttctggacag | ccccgacaga | ccctggaacc | ccctacatt | tccccctgcc | 120 |
| ctgctggtcg | tgaccgaggg | cgacaatgcc | accttcacct | gtagcttcag | caacaccagc | 180 |
| gagagcttcg | tgctgaactg | gtacagaatg | agccccagca | accagaccga | caagctggcc | 240 |
| gccttccccg | aggatagatc | tcagcccggc | caggactgcc | ggttcagagt | gacccagctg | 300 |
| cccaacggcc | gggacttcca | catgtctgtc | gtgcgggcca | gacggaacga | cagcggcaca | 360 |
| tatctgtgcg | gcgccatcag | cctggccccc | aaggcccaga | tcaaagagag | cctgagagcc | 420 |
| gagctgagag | tgaccgagag | aagggccgaa | gtgcctaccg | cccacccctag | cccatctcca | 480 |
| agacctgccg | gccagttcca | gacactcgtg | | | | 510 |

<210> SEQ ID NO 4
<211> LENGTH: 170
<212> TYPE: PRT
<213> ORGANISM: Artificial Sequence
<220> FEATURE:
<223> OTHER INFORMATION: PD1ECD

<400> SEQUENCE: 4

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170

<210> SEQ ID NO 5
<211> LENGTH: 170
<212> TYPE: PRT
<213> ORGANISM: Artificial Sequence
<220> FEATURE:
<223> OTHER INFORMATION: PD1ECD variant 1 A99L mutant

<400> SEQUENCE: 5

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Leu Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170

<210> SEQ ID NO 6
```

```
<211> LENGTH: 170
<212> TYPE: PRT
<213> ORGANISM: Artificial Sequence
<220> FEATURE:
<223> OTHER INFORMATION: PD1ECD variant 2 mutant

<400> SEQUENCE: 6

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe His
    50                  55                  60

Val Val Trp His Arg Glu Ser Pro Ser Gly Gln Thr Asp Thr Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Val Cys Gly Val Ile Ser Leu
        115                 120                 125

Ala Pro Lys Ile Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170

<210> SEQ ID NO 7
<211> LENGTH: 4
<212> TYPE: PRT
<213> ORGANISM: Artificial Sequence
<220> FEATURE:
<223> OTHER INFORMATION: Glycine linker 1

<400> SEQUENCE: 7

Gly Gly Gly Ser
1

<210> SEQ ID NO 8
<211> LENGTH: 7
<212> TYPE: PRT
<213> ORGANISM: Artificial Sequence
<220> FEATURE:
<223> OTHER INFORMATION: Glycine linker 2

<400> SEQUENCE: 8

Gly Gly Gly Ser Gly Gly Gly
1               5

<210> SEQ ID NO 9
<211> LENGTH: 3
<212> TYPE: PRT
<213> ORGANISM: Artificial Sequence
<220> FEATURE:
<223> OTHER INFORMATION: Glycine linker 3

<400> SEQUENCE: 9

Gly Gly Gly
1
```

<210> SEQ ID NO 10
<211> LENGTH: 66
<212> TYPE: DNA
<213> ORGANISM: Artificial Sequence
<220> FEATURE:
<223> OTHER INFORMATION: T2A nucleotide sequence

<400> SEQUENCE: 10

```
ggcggcggag agggcagagg aagtcttcta acatgcggtg acgtggagga gaatcccggc    60
cctagg                                                              66
```

<210> SEQ ID NO 11
<211> LENGTH: 66
<212> TYPE: DNA
<213> ORGANISM: Artificial Sequence
<220> FEATURE:
<223> OTHER INFORMATION: GMCSF signal sequence

<400> SEQUENCE: 11

```
atgcttctcc tggtgacaag ccttctgctc tgtgagttac cacacccagc attcctcctg    60
atccca                                                              66
```

<210> SEQ ID NO 12
<211> LENGTH: 60
<212> TYPE: DNA
<213> ORGANISM: Artificial Sequence
<220> FEATURE:
<223> OTHER INFORMATION: PD1 signal sequence

<400> SEQUENCE: 12

```
atgcagatcc ctcaggcccc ttggcctgtc gtgtgggctg tgctgcagct gggatggcgg    60
```

<210> SEQ ID NO 13
<211> LENGTH: 57
<212> TYPE: DNA
<213> ORGANISM: Artificial Sequence
<220> FEATURE:
<223> OTHER INFORMATION: CD19 signal sequence

<400> SEQUENCE: 13

```
atgcccccte ccagacttct cttttteete etcttcctga cgccgatgga agtaagg       57
```

<210> SEQ ID NO 14
<211> LENGTH: 2154
<212> TYPE: DNA
<213> ORGANISM: Artificial Sequence
<220> FEATURE:
<223> OTHER INFORMATION: EGFRt-T2A-PD1(A99L):IFNa2a

<400> SEQUENCE: 14

```
atgcttctcc tggtgacaag ccttctgctc tgtgagttac cacacccagc attcctcctg    60
atcccacgca aagtgtgtaa cggaataggt attggtgaat ttaaagactc actctccata   120
aatgctacga atattaaaca cttcaaaaac tgcacctcca tcagtggcga tctccacatc   180
ctgccggtgg catttagggg tgactccttc acacatactc ctcctctgga tccacaggaa   240
ctggatattc tgaaaaccgt aaaggaaatc acagggtttt tgctgattca ggcttggcct   300
gaaaacagga cggacctcca tgcctttgag aacctagaaa tcatacgcgg caggaccaag   360
caacatggtc agttttctct tgcagtcgtc agcctgaaca taacatcctt gggattacgc   420
tccctcaagg agataagtga tggagatgtg ataaatttcag gaaacaaaaa tttgtgctat   480
```

| | |
|---|---|
| gcaaatacaa taaactggaa aaaactgttt gggacctccg gtcagaaaac caaaattata | 540 |
| agcaacagag gtgaaaacag ctgcaaggcc acaggccagg tctgccatgc cttgtgctcc | 600 |
| cccgagggct gctggggccc ggagcccagg gactgcgtct cttgccggaa tgtcagccga | 660 |
| ggcagggaat gcgtggacaa gtgcaacctt ctggagggtg agccaaggga gtttgtggag | 720 |
| aactctgagt gcatacagtg ccacccagag tgcctgcctc aggccatgaa catcacctgc | 780 |
| acaggacggg gaccagacaa ctgtatccag tgtgcccact acattgacgg cccccactgc | 840 |
| gtcaagacct gcccggcagg agtcatggga gaaaacaaca ccctggtctg aagtacgca | 900 |
| gacgccggcc atgtgtgcca cctgtgccat ccaaactgca cctacggatg cactgggcca | 960 |
| ggtcttgaag gctgtccaac gaatgggcct aagatcccgt ccatcgccac tgggatggtg | 1020 |
| ggggccctcc tcttgctgct ggtggtggcc ctggggatcg gcctcttcat gggcggcgga | 1080 |
| gagggcagag gaagtcttct aacatgcggt gacgtggagg agaatcccgg ccctaggatg | 1140 |
| cagatccctc aggcccctg gcctgtcgtg tgggctgtgc tgcagctggg atggcggcct | 1200 |
| ggctggtttc tggacagccc cgacagaccc tggaaccccc ctacattttc ccctgccctg | 1260 |
| ctggtcgtga ccgagggcga caatgccacc ttcacctgta gcttcagcaa caccagcgag | 1320 |
| agcttcgtgc tgaactggta cagaatgagc cccagcaacc agaccgacaa gctggccgcc | 1380 |
| ttccccgagg atagatctca gcccggccag gactgccggt tcagagtgac ccagctgccc | 1440 |
| aacggccggg acttccacat gtctgtcgtg cgggccagac ggaacgacag cggcacatat | 1500 |
| ctgtgcggcg ccatcagcct ggccccaag ctccagatca agagagcct gagagccgag | 1560 |
| ctgagagtga ccgagagaag ggccgaagtg cctaccgccc accctagccc atctccaaga | 1620 |
| cctgccggcc agttccagac actcgtgggc ggaggatgcg acctgcctca gacacacagc | 1680 |
| ctgggcagca gacggaccct gatgctgctg gcccagatgc ggaagatcag cctgttcagc | 1740 |
| tgcctgaagg accggcacga cttcggcttc cctcaggaag agttcggcaa ccagtttcag | 1800 |
| aaggccgaga caatccccgt gctgcacgag atgatccagc agatcttcaa cctgttctcc | 1860 |
| accaaggaca gcagcgccgc ctgggacgag acactgctgg acaagttcta caccgagctg | 1920 |
| taccagcagc tgaatgacct ggaagccctg gtgatccagg gcgtgggcgt gacagagaca | 1980 |
| cccctgatga aggaagatag catcctggcc gtgcgcaagt acttccagcg gatcaccctg | 2040 |
| tacctgaaag agaagaagta cagccccgc gcctgggagg tcgtgcgcgc cgagatcatg | 2100 |
| agaagcttca gcctgagcac caacctgcag gaaagcctgc ggagcaaaga ataa | 2154 |

<210> SEQ ID NO 15
<211> LENGTH: 717
<212> TYPE: PRT
<213> ORGANISM: Artificial Sequence
<220> FEATURE:
<223> OTHER INFORMATION: EGFRt-T2A-PD1(A99L):IFNa2a

<400> SEQUENCE: 15

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
        50                  55                  60

Phe Arg Gly Asp Ser Phe Thr His Thr Pro Pro Leu Asp Pro Gln Glu
```

-continued

```
              65                  70                  75                  80
Leu Asp Ile Leu Lys Thr Val Lys Glu Ile Thr Gly Phe Leu Leu Ile
                    85                  90                  95
Gln Ala Trp Pro Glu Asn Arg Thr Asp Leu His Ala Phe Glu Asn Leu
                100                 105                 110
Glu Ile Ile Arg Gly Arg Thr Lys Gln His Gly Gln Phe Ser Leu Ala
                115                 120                 125
Val Val Ser Leu Asn Ile Thr Ser Leu Gly Leu Arg Ser Leu Lys Glu
            130                 135                 140
Ile Ser Asp Gly Asp Val Ile Ile Ser Gly Asn Lys Asn Leu Cys Tyr
145                 150                 155                 160
Ala Asn Thr Ile Asn Trp Lys Lys Leu Phe Gly Thr Ser Gly Gln Lys
                    165                 170                 175
Thr Lys Ile Ile Ser Asn Arg Gly Glu Asn Ser Cys Lys Ala Thr Gly
                180                 185                 190
Gln Val Cys His Ala Leu Cys Ser Pro Glu Gly Cys Trp Gly Pro Glu
                195                 200                 205
Pro Arg Asp Cys Val Ser Cys Arg Asn Val Ser Arg Gly Arg Glu Cys
            210                 215                 220
Val Asp Lys Cys Asn Leu Leu Glu Gly Glu Pro Arg Glu Phe Val Glu
225                 230                 235                 240
Asn Ser Glu Cys Ile Gln Cys His Pro Glu Cys Leu Pro Gln Ala Met
                    245                 250                 255
Asn Ile Thr Cys Thr Gly Arg Gly Pro Asp Asn Cys Ile Gln Cys Ala
                260                 265                 270
His Tyr Ile Asp Gly Pro His Cys Val Lys Thr Cys Pro Ala Gly Val
            275                 280                 285
Met Gly Glu Asn Asn Thr Leu Val Trp Lys Tyr Ala Asp Ala Gly His
            290                 295                 300
Val Cys His Leu Cys His Pro Asn Cys Thr Tyr Gly Cys Thr Gly Pro
305                 310                 315                 320
Gly Leu Glu Gly Cys Pro Thr Asn Gly Pro Lys Ile Pro Ser Ile Ala
                325                 330                 335
Thr Gly Met Val Gly Ala Leu Leu Leu Leu Leu Val Val Ala Leu Gly
                340                 345                 350
Ile Gly Leu Phe Met Gly Gly Glu Gly Arg Gly Ser Leu Leu Thr
                355                 360                 365
Cys Gly Asp Val Glu Glu Asn Pro Gly Pro Arg Met Gln Ile Pro Gln
            370                 375                 380
Ala Pro Trp Pro Val Val Trp Ala Val Leu Gln Leu Gly Trp Arg Pro
385                 390                 395                 400
Gly Trp Phe Leu Asp Ser Pro Asp Arg Pro Trp Asn Pro Pro Thr Phe
                    405                 410                 415
Ser Pro Ala Leu Leu Val Val Thr Glu Gly Asp Asn Ala Thr Phe Thr
                420                 425                 430
Cys Ser Phe Ser Asn Thr Ser Glu Ser Phe Val Leu Asn Trp Tyr Arg
            435                 440                 445
Met Ser Pro Ser Asn Gln Thr Asp Lys Leu Ala Ala Phe Pro Glu Asp
            450                 455                 460
Arg Ser Gln Pro Gly Gln Asp Cys Arg Phe Arg Val Thr Gln Leu Pro
465                 470                 475                 480
Asn Gly Arg Asp Phe His Met Ser Val Val Arg Ala Arg Arg Asn Asp
                    485                 490                 495
```

```
Ser Gly Thr Tyr Leu Cys Gly Ala Ile Ser Leu Ala Pro Lys Leu Gln
            500                 505                 510

Ile Lys Glu Ser Leu Arg Ala Glu Leu Arg Val Thr Glu Arg Arg Ala
            515                 520                 525

Glu Val Pro Thr Ala His Pro Ser Pro Ser Pro Arg Pro Ala Gly Gln
        530                 535                 540

Phe Gln Thr Leu Val Gly Gly Cys Asp Leu Pro Gln Thr His Ser
545                 550                 555                 560

Leu Gly Ser Arg Arg Thr Leu Met Leu Leu Ala Gln Met Arg Lys Ile
                565                 570                 575

Ser Leu Phe Ser Cys Leu Lys Asp Arg His Asp Phe Gly Phe Pro Gln
            580                 585                 590

Glu Glu Phe Gly Asn Gln Phe Gln Lys Ala Glu Thr Ile Pro Val Leu
            595                 600                 605

His Glu Met Ile Gln Gln Ile Phe Asn Leu Phe Ser Thr Lys Asp Ser
            610                 615                 620

Ser Ala Ala Trp Asp Glu Thr Leu Leu Asp Lys Phe Tyr Thr Glu Leu
625                 630                 635                 640

Tyr Gln Gln Leu Asn Asp Leu Glu Ala Cys Val Ile Gln Gly Val Gly
                645                 650                 655

Val Thr Glu Thr Pro Leu Met Lys Glu Asp Ser Ile Leu Ala Val Arg
            660                 665                 670

Lys Tyr Phe Gln Arg Ile Thr Leu Tyr Leu Lys Glu Lys Lys Tyr Ser
            675                 680                 685

Pro Cys Ala Trp Glu Val Val Arg Ala Glu Ile Met Arg Ser Phe Ser
            690                 695                 700

Leu Ser Thr Asn Leu Gln Glu Ser Leu Arg Ser Lys Glu
705                 710                 715

<210> SEQ ID NO 16
<211> LENGTH: 2154
<212> TYPE: DNA
<213> ORGANISM: Artificial Sequence
<220> FEATURE:
<223> OTHER INFORMATION: EGFRt-T2A-PD1(HAC-1):IFNa2a

<400> SEQUENCE: 16
atgcttctcc tggtgacaag ccttctgctc tgtgagttac cacacccagc attcctcctg      60
atcccacgca aagtgtgtaa cggaataggt attggtgaat taaagactc actctccata     120 aatgctacga atattaaaca cttcaaaaac tgcacctcca tcagtggcga tctccacatc     180
ctgccggtgg catttagggg tgactccttc acacatactc ctcctctgga tccacaggaa     240
ctggatattc tgaaaaccgt aaaggaaatc acagggtttt gctgattca ggcttggcct      300 gaaaacagga cggacctcca tgcctttgag aacctagaaa tcatacgcgg caggaccaag     360
caacatggtc agttttctct tgcagtcgtc agcctgaaca acatccctt gggattacgc      420 tccctcaagg agataagtga tggagatgtg ataatttcag aaacaaaaa tttgtgctat      480 gcaaatacaa taaactggaa aaactgtttt gggacctccg gtcagaaaac caaaattata     540
agcaacagag gtgaaaacag ctgcaaggcc acaggccagg tctgccatgc cttgtgctcc     600
cccgagggct gctgggggccc ggagcccagg gactgcgtct cttgccggaa tgtcagccga     660
ggcagggaat gcgtggacaa gtgcaacctt ctggagggtg agccaaggga gtttgtggag     720
aactctgagt gcatacagtg ccacccagag tgcctgcctc aggccatgaa catcacctgc     780
```

| | |
|---|---|
| acaggacggg gaccagacaa ctgtatccag tgtgcccact acattgacgg cccccactgc | 840 |
| gtcaagacct gcccggcagg agtcatggga gaaaacaaca ccctggtctg aagtacgca | 900 |
| gacgccggcc atgtgtgcca cctgtgccat ccaaactgca cctacggatg cactgggcca | 960 |
| ggtcttgaag gctgtccaac gaatgggcct aagatcccgt ccatcgccac tgggatggtg | 1020 |
| ggggccctcc tcttgctgct ggtggtggcc ctggggatcg gcctcttcat gggcggcgga | 1080 |
| gagggcagag gaagtcttct aacatgcggt gacgtggagg agaatcccgg ccctaggatg | 1140 |
| cagatccctc aggccccttg gctgtcgtg tgggctgtgc tgcagctggg atggcggcct | 1200 |
| ggctggtttc tggacagccc cgacagaccc tggaaccccc ctacatttc ccctgccctg | 1260 |
| ctggtcgtga ccgagggcga caatgccacc ttcacctgta gcttcagcaa caccagcgag | 1320 |
| agcttccatg ttatttggca tagagaaagc cccagcggtc agaccgacac tctggccgcc | 1380 |
| ttccccgagg atagatctca gcccggccag gactgccggt tcagagtgac ccagctgccc | 1440 |
| aacggccggg acttccacat gtctgtcgtg cgggccagac ggaacgacag cggcacatat | 1500 |
| gtttgcggcg ttatcagcct ggcccccaag attcagatca agagagcct gagagccgag | 1560 |
| ctgagagtga ccgagagaag ggccgaagtg cctaccgccc accctagccc atctccaaga | 1620 |
| cctgccggcc agttccagac actcgtgggc ggaggatgcg acctgcctca gacacacagc | 1680 |
| ctgggcagca gacggaccct gatgctgctg gcccagatgc ggaagatcag cctgttcagc | 1740 |
| tgcctgaagg accggcacga cttcggcttc cctcaggaag agttcggcaa ccagtttcag | 1800 |
| aaggccgaga caatccccgt gctgcacgag atgatccagc agatcttcaa cctgttctcc | 1860 |
| accaaggaca gcagcgccgc ctgggacgag acactgctgg acaagttcta caccgagctg | 1920 |
| taccagcagc tgaatgacct ggaagcctgc gtgatccagg gcgtgggcgt gacagagaca | 1980 |
| cccctgatga ggaagatag catcctggcc gtgcgcaagt acttccagcg gatcaccctg | 2040 |
| tacctgaaag agaagaagta cagcccctgc gcctgggagg tcgtgcgcgc cgagatcatg | 2100 |
| agaagcttca gcctgagcac caacctgcag gaaagcctgc ggagcaaaga ataa | 2154 |

<210> SEQ ID NO 17
<211> LENGTH: 2154
<212> TYPE: DNA
<213> ORGANISM: Artificial Sequence
<220> FEATURE:
<223> OTHER INFORMATION: EGFRt-T2A-PD1(G14-1):IFNa2a

<400> SEQUENCE: 17

| | |
|---|---|
| atgcttctcc tggtgacaag ccttctgctc tgtgagttac cacacccagc attcctcctg | 60 |
| atcccacgca aagtgtgtaa cggaataggt attggtgaat taaagactc actctccata | 120 |
| aatgctacga atattaaaca cttcaaaaac tgcacctcca tcagtggcga tctccacatc | 180 |
| ctgccggtgg catttagggg tgactccttc acacatactc ctcctctgga tccacaggaa | 240 |
| ctggatattc tgaaaccgt aaaggaaatc acagggtttt tgctgattca ggcttggcct | 300 |
| gaaaacagga cggacctcca tgcctttgag aacctagaaa tcatacgcgg caggaccaag | 360 |
| caacatggtc agttttctct tgcagtcgtc agcctgaaca taacatcctt gggattacgc | 420 |
| tccctcaagg agataagtga tggagatgtg ataatttcag gaaacaaaaa tttgtgctat | 480 |
| gcaaatacaa taaactggaa aaaactgttt ggacctccg gtcagaaaac caaaattata | 540 |
| agcaacagag gtgaaaacag ctgcaaggcc acaggccagg tctgccatgc cttgtgctcc | 600 |
| cccgagggct gctggggccc ggagcccagg gactgcgtct cttgccggaa tgtcagccga | 660 |
| ggcagggaat gcgtggacaa gtgcaacctt ctggagggtg agccaaggga gtttgtggag | 720 |

```
aactctgagt gcatacagtg ccacccagag tgcctgcctc aggccatgaa catcacctgc    780
acaggacggg gaccagacaa ctgtatccag tgtgcccact acattgacgg cccccactgc    840
gtcaagacct gcccggcagg agtcatggga gaaaacaaca ccctggtctg gaagtacgca    900
gacgccggcc atgtgtgcca cctgtgccat ccaaactgca cctacggatg cactgggcca    960
ggtcttgaag gctgtccaac gaatgggcct aagatcccgt ccatcgccac tgggatggtg   1020
ggggccctcc tcttgctgct ggtggtggcc ctggggatcg gcctcttcat gggcggcgga   1080
gagggcagag gaagtcttct aacatgcggt gacgtggagg agaatcccgg ccctaggatg   1140
cagatccctc aggccccttg gcctgtcgtg tgggctgtgc tgcagctggg atggcggcct   1200
ggctggtttc tggacagccc cgacagaccc tggaaccccc ctacattttc ccctgccctg   1260
ctggtcgtga ccgagggcga caatgccacc ttcacctgta gcttcagcaa caccagcgag   1320
agcttcagac tggtgtggca tagagaaagc cccggctacg agaccgacac tctggccagc   1380
ttccccgagg atagatctac cccccctgcct gactgccggt tcagagtgac ccagctgccc   1440
aacggccggg acttccacat gtctgtcgtg cgggccagac ggaacgacag cggcacatat   1500
gtttgcggcg ccatcgcctt ccaccccgtg attcagatca aagagagcct gagagccgag   1560
ctgagagtga ccgagagaag ggccgaagtg cctaccgccc accctagccc atctccaaga   1620
cctgccggcc agttccagac actcgtgggc ggaggatgcg acctgcctca gacacacagc   1680
ctgggcagca gacggaccct gatgctgctg gcccagatgc ggaagatcag cctgttcagc   1740
tgcctgaagg accggcacga cttcggcttc cctcaggaag agttcggcaa ccagtttcag   1800
aaggccgaga caatccccgt gctgcacgag atgatccagc agatcttcaa cctgttctcc   1860
accaaggaca gcagcgccgc ctgggacgag acactgctgg acaagttcta caccgagctg   1920
taccagcagc tgaatgacct ggaagcctgc gtgatccagg gcgtgggcgt gacagagaca   1980
cccctgatga aggaagatag catcctggcc gtgcgcaagt acttccagcg gatcaccctg   2040
tacctgaaag agaagaagta cagcccctgc gcctgggagg tcgtgcgcgc cgagatcatg   2100
agaagcttca gcctgagcac caacctgcag gaaagcctgc ggagcaaaga ataa         2154
```